United States Patent
Wuest

(10) Patent No.: US 9,688,715 B2
(45) Date of Patent: Jun. 27, 2017

(54) SYNTHETIC PGPG ANALOGS, METHODS OF PREPARATION AND METHODS OF USE

(71) Applicant: TEMPLE UNIVERSITY—OF THE COMMONWEALTH SYSTEM OF HIGHER EDUCATION, Philadelphia, PA (US)

(72) Inventor: William Martin Wuest, Wallingford, PA (US)

(73) Assignee: TEMPLE UNIVERSITY—Of The Commonwealth System of Higher Education, Philadelphia, PA (US)

( * ) Notice: Subject to any disclaimer, the term of this patent is extended or adjusted under 35 U.S.C. 154(b) by 230 days.

(21) Appl. No.: 14/405,511

(22) PCT Filed: Jun. 17, 2013

(86) PCT No.: PCT/US2013/046093
§ 371 (c)(1),
(2) Date: Dec. 4, 2014

(87) PCT Pub. No.: WO2013/192078
PCT Pub. Date: Dec. 27, 2013

(65) Prior Publication Data
US 2015/0175649 A1  Jun. 25, 2015

Related U.S. Application Data

(60) Provisional application No. 61/663,000, filed on Jun. 22, 2012.

(51) Int. Cl.
| | | |
|---|---|---|
| *A01N 43/04* | (2006.01) | |
| *A61K 31/70* | (2006.01) | |
| *C07H 19/20* | (2006.01) | |
| *C07H 19/167* | (2006.01) | |
| *C07H 19/173* | (2006.01) | |
| *G01N 33/53* | (2006.01) | |
| *C07H 23/00* | (2006.01) | |
| *C07H 19/16* | (2006.01) | |
| *G01N 33/569* | (2006.01) | |
| *C07D 473/18* | (2006.01) | |
| *C07D 519/00* | (2006.01) | |

(52) U.S. Cl.
CPC .......... *C07H 23/00* (2013.01); *C07D 473/18* (2013.01); *C07D 519/00* (2013.01); *C07H 19/16* (2013.01); *C07H 19/20* (2013.01); *G01N 33/56911* (2013.01)

(58) Field of Classification Search
CPC ........ C07H 19/16; C07H 19/20; C07H 23/00; C07D 519/00; C07D 5473/18; G01N 33/56911
See application file for complete search history.

(56) References Cited

U.S. PATENT DOCUMENTS

| 6,967,196 B1 | 11/2005 | Smith et al. |
| 2009/0012038 A1 | 1/2009 | Spormann et al. |

FOREIGN PATENT DOCUMENTS

| WO | 2009/156421 A1 | 12/2009 |
| WO | 2010/132665 A1 | 11/2010 |

OTHER PUBLICATIONS ( R ) Bare et al., Synthesis of a Single G-Quartet Platform in Water, Journal of the American Chemical Society, 135 (32), 11985-11989 (Jul. 16, 2013).*
(S) Nikan et al., "Synthesis of a Water-Soluble Triazole-linked Cavitand-Guanosine COnjugate," Tetrahedron Letters, 52 (15), 1791-1793 (Feb. 13, 2011).*
Sato, et al., "Synthesis and Properties of a New Oligonucleotide Analogue Containing an Internucleotide Squaryl Amide Linkage," Nucleic Acids Research Suppl. No. 1, pp. 121-122 (2001).
Meanwell, "Synopsis of Some Recent Tactical Application of Bioisosteres in Drug Design," J. Med. Chem. 54, pp. 2529-2591 (2011).
Sato, et al., "Squaryl Group as a New Mimic of Phosphate Group in Modified Oligodeoxynucleotides: Synthesis and Properties of New Oligodeoxynucleotide Analogues Containing an Internucleotidic," J. Am. Chem. Soc.,124 (43), pp. 12715-12724 (2002).
Seio, et al., "Synthesis and Properties of New Nucleotide Analogues Possessing Squaramide Moieties as New Phosphate Isosters," Eur. J. Org. Chem., pp. 5163-5170 (2005).
Furukawa et al., "Identification of Ligand Analogues that Control c-di-GMP Riboswitches," ACS Chemical Biology, Publication Date (Web): vol. 7, pp. 1436-1443 [Downloaded from: http://www.ncbi.nlm.nih.gov/pubmed/22646696].

(Continued)

*Primary Examiner* — Lawrence E Crane
(74) *Attorney, Agent, or Firm* — Drinker Biddle & Reath LLP

(57) ABSTRACT

The present invention relates to compounds according to Formula I: and salts thereof, wherein $R_1$, $R_2$, $R_3$, $R_4$, and L are as defined herein. Methods for preparing compounds of Formula I are also provided. The present invention further includes methods of treating and preventing bacterial infections, and methods of identifying pGpG-binding domains in bacteria, using the compounds of Formula I.

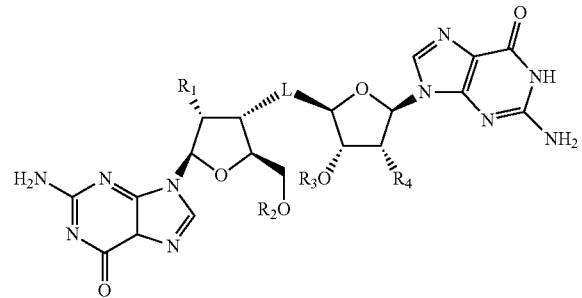

7 Claims, No Drawings

(56) References Cited

OTHER PUBLICATIONS

Chow et al. "Novel Synthesis of 2'-O-methylguanosine," Bioorganic & Medicinal Chemistry Letters, vol. 13, pp. 1631-1634 [Downloaded from www.sciencedirect.com].
Daher et al. "Rational Design, Synthesis, and Evaluation of New Selective Inhibitors of Microbial Class II (Zinc Dependent) Fructose Bis-phosphate Aldolases," J. Med. Chem. 53, pp. 7836-7842 (2010).
Izdebski et al. "A New Convenient Method for the Synthesis of Symmetrical and Unsymmetrical N,N'-Disubstitued Ureas," Synthesis-Stuttgart(6), pp. 423-425 (Jun. 1989).
Storer, et al. "Squaramides: Physical Properties, Synthesis and Applications," Chem Soc Rev., 40, pp. 2330-2346 (2011).
Matteucci, et al. "Hybridization Properties of Oligonucleotides Bearing a Tricyclic 2'-Deoxycytidine Analog Based on a Carbazole Ring System," Tetrahedron Letters, vol. 37, No. 29, pp. 5057-5060 (1996).
Paredes, et al. "Click Chemistry for Rapid Labeling and Ligation of RNA," ChemBioChem 12, pp. 125-131 (2011).
Wannagat, et al. "Cyclodisilazane mit verschiedenen Substituenten an alien vier Ringgliedern," Monatshefte fur Chemie 110, pp. 1089-1097 (1979).
Kline, et al. "Design and Synthesis of bis-carbamate Analogs of Cyclic bis-(3'-5')-Diguanylic Acid (c-di-GMP) and the Acyclic Dimer PGPG," Nucleosides, Nucleotides and Nucleic Acids, 27:12, pp. 1282-1300 [Downloaded from http://dx.doi.org/10.1080/15257770802554150] (2008).

\* cited by examiner

SYNTHETIC PGPG ANALOGS, METHODS OF PREPARATION AND METHODS OF USE

CROSS-REFERENCE TO RELATED APPLICATION

This application is a national stage application (under 35 U.S.C. §371) of PCT/US2013/046093, filed Jun. 17, 2013, which claims the benefit of the filing date of U.S. Provisional Patent Application No. 61/663,000, filed Jun. 22, 2012. The entire disclosure of Provisional Patent Application No. 61/663,000 is incorporated herein by reference.

FIELD OF THE INVENTION

The invention relates to compounds, methods for their preparation, methods for their use, and compositions including them. The invention further provides methods for the treatment and prevention of bacterial infections.

BACKGROUND OF THE INVENTION

Bacterial infections are among the most common causes of medical complications and illness in developed countries. That said, many bacterial infections develop resistance to conventional antibiotics. There is a need to develop new antibacterial compound to address the problem of drug-resistant strains of bacteria. Thus, identifying new effective drugs for bacterial infections is a continuing focus of medical research.

pGpG is a secondary messenger molecule which is vital for many pathogenic bacteria. pGpG plays an important role in chemical signaling and is vital in numerous enzymatic processes. To date, little is known about the specific targets that recognize pGpG and the method by which pGpG signaling occurs. Accordingly, the development of a chemical probe which can be used to identify pGpG-binding domains would be a significant advance.

SUMMARY OF THE INVENTION

It is believed that that certain compounds and compositions are useful for the treatment of bacterial infections. The compounds of the invention are pGpG mimics and related derivatives thereof.

Provided is a compound of Formula I or a salt thereof:

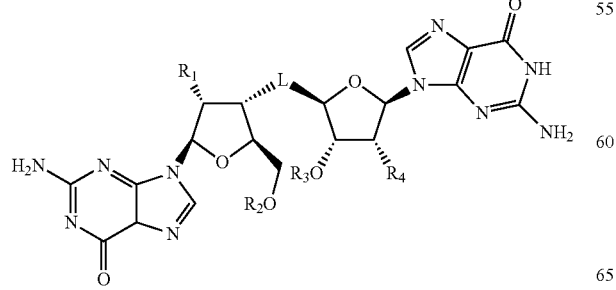

wherein,

L is selected from the group consisting of:

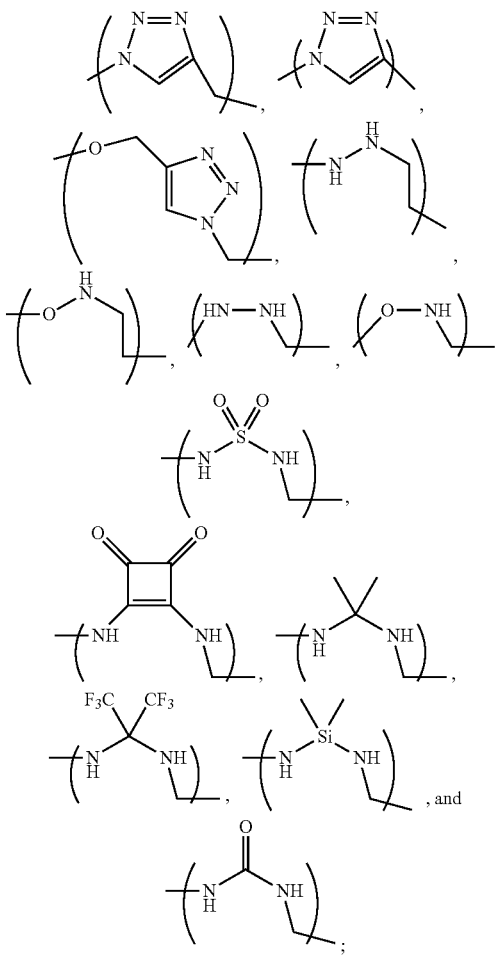

$R_1$ is selected from the group consisting of hydrogen, hydroxyl, $(C_1-C_6)$alkyl, $(C_1-C_6)$alkyloxy, and $-OPO_3H_2$; and $R_2$ is selected from the group consisting of:
hydrogen,
$-PO_3H_2$,

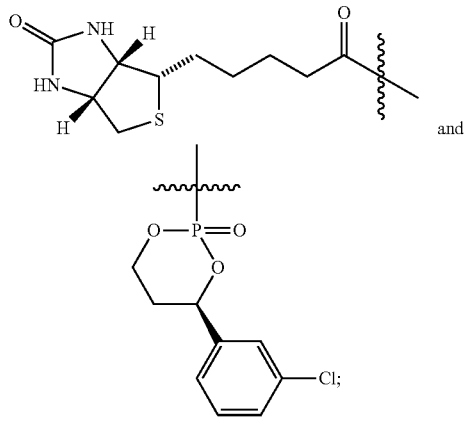

R₃ is selected from the group consisting of:
hydrogen,
—PO₃H₂,

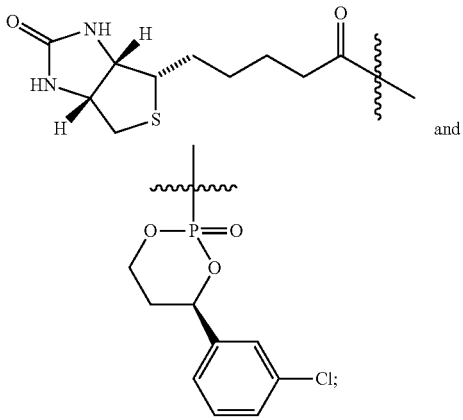

and

R₄ is selected from the group consisting of hydrogen, hydroxyl, (C₁-C₆)alkyl, (C₁-C₆)alkyloxy and —OPO₃H₂.

Further provided is a pharmaceutical composition comprising a pharmaceutically acceptable carrier and a compound of Formula I, or a pharmaceutically acceptable salt thereof.

Further provided is a method of treating an individual suffering from a bacterial infection, comprising administering to the individual an effective amount of at least one compound of Formula I, or a pharmaceutically acceptable salt thereof.

Further provided is a method for preventing and/or reducing the risk of bacterial infection in individuals comprising administering to the individual an effective amount of at least one compound of Formula I, or a pharmaceutically acceptable salt thereof.

In particular embodiments, the bacterial infection is caused by at least one bacteria selected from the group consisting of *Pseudomonas aeruginosa; Pseudomonas fluorescens; Yersinas pestis; Vibrio cholerae; Salmonella enterica; Salmonella Typhimurium; Legionella pneumophia; Brucella melitensis; Bordetella pertussis; Streptococcus mutans; Acinetobacter baumannii; Staphylococcus aureus; Escherichia coli*; and *Bacillus anthracis*.

Further provided is a method of identifying pGpG-binding domains in bacteria by contacting bacteria with at least one compound of Formula I, or a salt thereof. The compound or salt thereof is contacted with the bacteria, or a fraction thereof, to identify pGpG-binding domains in the bacteria.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

DETAILED DESCRIPTION OF THE INVENTION

The compounds and compositions of the invention are believed to inhibit proliferation of bacterial cells, and kill various bacterial cells in or on an individual suffering from bacterial infection. The compounds of the invention are believed to interfere with pGpG pathways in bacterial cells, which causes the death of the bacterial cells and/or inhibition of the formation of bacterial biofilms. The compounds are believed effective against a broad range of bacteria, including but not limited to the following: *Pseudomonas aeruginosa; Pseudomonas fluorescens; Yersinas pestis; Vibrio cholerae; Salmonella enterica; Salmonella Typhimurium; Legionella pneumophia; Brucella melitensis; Bordetella pertussis; Streptococcus mutans; Acinetobacter baumannii; Staphylococcus aureus; Escherichia coli*; and *Bacillus anthracis*.

The compounds are also believed to be useful as probes for analysis of pGpG bacterial pathways. In one embodiment, compound bearing a detectable label, e.g., a label conjugated to a biotin linker, are applied as chemical probes for the identification of pGpG-binding domains. Previous methods have successfully utilized biotin-conjugate entities to identify signaling molecules in bacteria. Generally speaking, biotin-conjugated pGpG analogs may be applied either directly to bacteria or a fraction or component thereof, e.g., a bacterial lysate.

After suitable incubation time, the bacteria are lysed (if not lysed previously), pelleted by centrifugation, applied to a streptavidin column, and eluted. All pGpG-binding entities are sequenced by mass spectrometry to confirm their identity.

Apart from inhibiting bacterial cell proliferation, the bacterial inhibitory activity of the compound can provide further antibacterial utility by blocking the pGpG pathway in bacterial cells and causing inhibition of formation of biofilms.

I. DEFINITIONS

1. General

As used in the specification and the appended claims, the singular forms "a," "an" and "the" include plural referents unless the context clearly dictates otherwise.

As used herein, the terms "treat" and "treatment" are used interchangeably and are meant to indicate a postponement of development of a disorder and/or a reduction in the severity of symptoms that will or are expected to develop. The terms further include ameliorating existing symptoms, preventing additional symptoms, and ameliorating or preventing the underlying metabolic causes of symptoms.

As used herein, "individual" (as in the subject of the treatment) means both mammals and non-mammals. Mammals include, for example, humans; nonhuman primates, e.g. apes and monkeys; cattle; horses; sheep; and goats. Non-mammals include, for example, fish and birds.

The expression "effective amount", when used to describe therapy to an individual suffering from a bacterial infection, refers to the amount of a compound according to Formula I that inhibits the growth or proliferation, resulting in a therapeutically useful and killing of bacterial cells.

The term "bacterial infection" means a disorder wherein unwanted bacteria or unwanted amounts of bacteria cause infection or illness in an individual.

The term "chemical probe" means a compound or composition capable of identifying bacterial proteins, receptors and other biological components with the appropriate procedure.

The term "anti-bacterial" means capable of killing bacterial cells or inhibiting the proliferation thereof, or inhibitions the formation of biofilms.

2. Chemical

In the following paragraphs some of the definitions include examples. The examples are intended to be illustrative, and not limiting.

The term "alkyl", by itself or as part of another substituent means, unless otherwise stated, a straight, or branched chain hydrocarbon having the number of carbon atoms designated (i.e. $C_1$-$C_6$ means one to six carbons) and includes straight, branched chain or cyclic groups. Examples include methyl, ethyl, propyl, isopropyl, butyl, isobutyl, tert-butyl, pentyl, neopentyl, and hexyl. Most preferred is ($C_1$-$C_3$)alkyl, particularly ethyl, methyl and isopropyl.

The term "alkoxy", employed alone or in combination with other terms, means, unless otherwise stated, an alkyl group, as defined above, connected to the rest of the molecule via an oxygen atom. The terms alkoxy includes, for example, methoxy, ethoxy, 1-propoxy, 2-propoxy (isopropoxy) and their higher homologs and isomers. The alkyl portion of the alkoxy group can have a designated number of carbon atoms as defined for alkyl groups above. Preferred are ($C_1$-$C_3$)alkoxy, particularly ethoxy and methoxy.

A "coupling agent" is a compound that is capable of reacting with two or more functional groups to form a linking group. The nature of the coupling agent depends on the type of linking group sought. A coupling agent can include, but is not limited to the following: Copper Tris-(hydroxypropyltriazolylmethyl)amine, 3,4-dihydroxycyclobut-3-ene-1,2-dione, propan-2-one, 1,1,1,3,3,3-hexafluoropropan-2-one, dichlorodimethylsilane, and bis(4-nitrophenyl) carbonate. For example, in a preferred embodiment, diethyl squarate can act as a coupling agent for coupling with (i.e. reacting and tethering together) a compound having a primary amine with another compound having a —$CH_2$—$NH_2$ group, to form linking group depicted by the following structure:

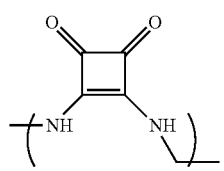

The terms "halo" or "halogen" by themselves or as part of another substituent mean, unless otherwise stated, a fluorine, chlorine, bromine, or iodine atom. Preferably, a halogen includes iodine, chlorine, or bromine, more preferably, iodine.

The inclusion of a parenthetical or a wavy line, ⌇, indicates a point of connection to a chemical structure to another chemical structure. For example, a molecule of the structure:

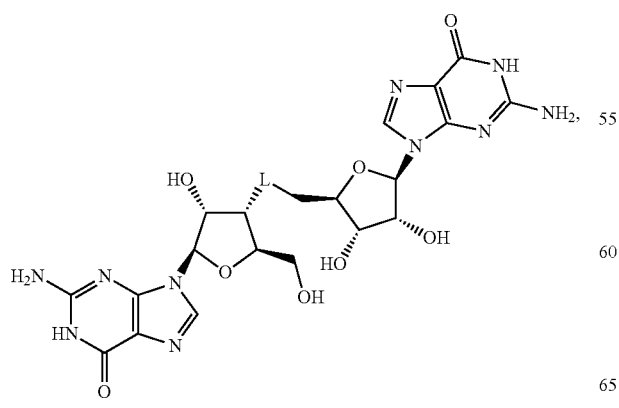

where L is:

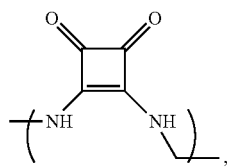

would be understood to represent the compound:

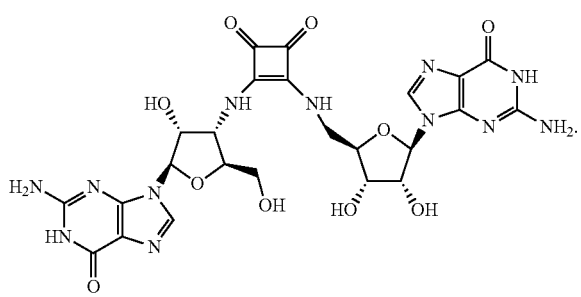 [SMILES: Nc1nc2c(ncn2[C@@H]2O[C@H](CNc3c(N[C@H]4[C@@H](O)[C@H](n5cnc6c(=O)[nH]c(N)nc65)O[C@@H]4CO)c(=O)c3=O)[C@@H](O)[C@H]2O)c(=O)[nH]1]

II. COMPOUNDS OF THE INVENTION

In one aspect, the invention is a compound of Formula I, or a salt thereof,

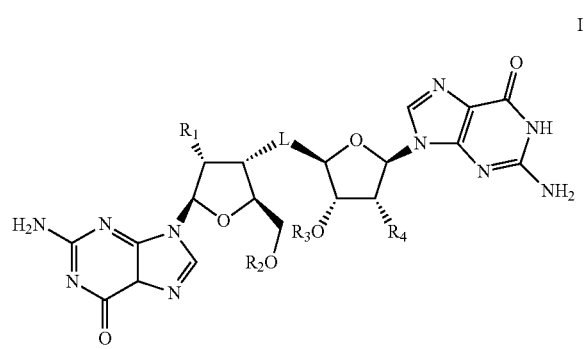

I wherein:

L is selected from the group consisting of:

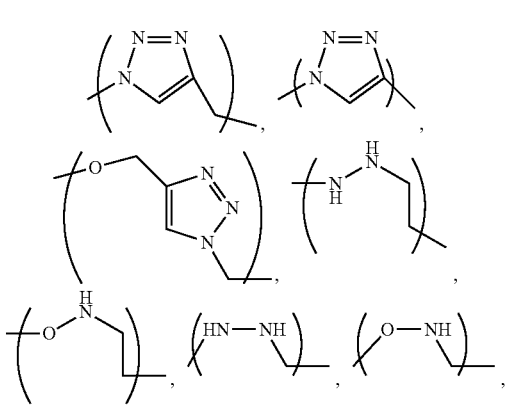

7

-continued

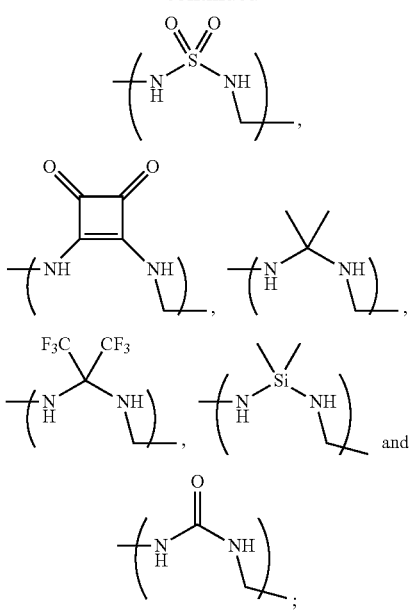

$R_1$ is selected from the group consisting of hydrogen, hydroxyl, $(C_1-C_6)$alkyl, $(C_1-C_6)$alkyloxy and —OPO$_3$H$_2$;

$R_2$ is selected from the group consisting of:
hydrogen,
—PO$_3$H$_2$,

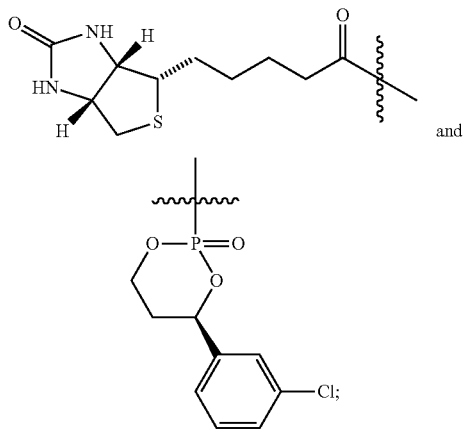

$R_3$ is selected from the group consisting of:
hydrogen,
—PO$_3$H$_2$,

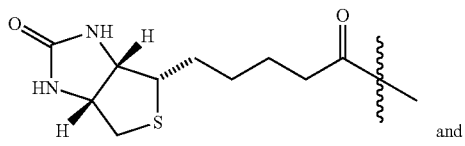

8

-continued

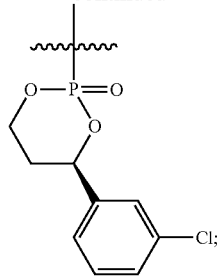

$R_4$ is selected from the group consisting of hydrogen, hydroxyl, $(C_1-C_6)$alkyl, $(C_1-C_6)$alkyloxy and —OPO$_3$H$_2$.

In certain embodiments, the salt of a compound of Formula I is a pharmaceutically acceptable salt.

Another particular embodiment of the invention comprises a compound of Formula I, or a salt thereof, wherein at least one of $R_1$, $R_2$, $R_3$ and $R_4$ is hydrogen.

Another particular embodiment of the invention comprises a compound of Formula I, or a salt thereof, wherein at least one of $R_1$ and $R_4$ is hydrogen.

Another particular embodiment of the invention comprises a compound of Formula I, or a salt thereof, wherein L is:

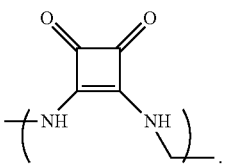

In certain embodiments, a compound of Formula I, or a salt thereof, is selected from the group consisting of:

(1) 2-amino-9-((2R,3R,4S,5S)-4-(4-(((2R,3S,5R)-5-(2-amino-6-oxo-1H-purin-9(6H)-yl)-3-hydroxytetrahydrofuran-2-yl)methyl)-1H-1,2,3-triazol-1-yl)-3-hydroxy-5-(hydroxymethyl)tetrahydrofuran-2-yl)-1H-purin-6(9H)-one;

(2) 2-amino-9-((2R,3R,4S,5S)-4-(4-((2R,3S,5R)-5-(2-amino-6-oxo-1H-purin-9(6H)-yl)-3-hydroxytetrahydrofuran-2-yl)-1H-1,2,3-triazol-1-yl)-3-hydroxy-5-(hydroxymethyl)tetrahydrofuran-2-yl)-1H-purin-6(9H)-one;

(3) 2-amino-9-((2R,3R,4S,5R)-4-((1-((2S,3S,5R)-5-(2-amino-6-oxo-1H-purin-9(6H)-yl)-3-hydroxytetrahydrofuran-2-yl)-1H-1,2,3-triazol-4-yl)methoxy)-3-hydroxy-5-(hydroxymethyl)tetrahydrofuran-2-yl)-1H-purin-6(9H)-one;

(4) 2-amino-9-((2R,3R,4S,5S)-4-(2-(2-((2R,3S,5R)-5-(2-amino-6-oxo-1H-purin-9(6H)-yl)-3-hydroxytetrahydrofuran-2-yl)ethyl)hydrazinyl)-3-hydroxy-5-(hydroxymethyl)tetrahydrofuran-2-yl)-1H-purin-6(9H)-one;

(5) 2-amino-9-((2R,3R,4S,5R)-4-(((2-((2R,3S,5R)-5-(2-amino-6-oxo-1H-purin-9(6H)-yl)-3-hydroxytetrahydrofuran-2-yl)ethyl)amino)oxy)-3-hydroxy-5-(hydroxymethyl)tetrahydrofuran-2-yl)-1H-purin-6(9H)-one;

(6) 2-amino-9-((2R,3R,4S,5S)-4-(2-(((2R,3S,5R)-5-(2-amino-6-oxo-1H-purin-9(6H)-yl)-3-hydroxytetrahydrofuran-2-yl)methyl)hydrazinyl)-3-hydroxy-5-(hydroxymethyl)tetrahydrofuran-2-yl)-1H-purin-6(9H)-one;

(7) 2-amino-9-((2R,3R,4S,5R)-4-(((((2R,3S,5R)-5-(2-amino-6-oxo-1H-purin-9(6H)-yl)-3-hydroxytetrahydrofuran-2-yl)methyl)amino)oxy)-3-hydroxy-5-(hydroxymethyl)tetrahydrofuran-2-yl)-1H-purin-6(9H)-one;

(8) 3-((((2R,3S,5R)-5-(2-amino-6-oxo-1H-purin-9(6H)-yl)-3-hydroxytetrahydrofuran-2-yl)methyl)amino)-4-(((2S,3S,4R,5R)-5-(2-amino-6-oxo-1H-purin-9(6H)-yl)-4-hydroxy-2-(hydroxymethyl)tetrahydrofuran-3-yl)amino)cyclobut-3-ene-1,2-dione;

(9) 2-amino-9-((2R,3R,4S,5S)-4-((2-((((2R,3S,5R)-5-(2-amino-6-oxo-1H-purin-9(6H)-yl)-3-hydroxytetrahydrofuran-2-yl)methyl)amino)propan-2-yl)amino)-3-hydroxy-5-(hydroxymethyl)tetrahydrofuran-2-yl)-1H-purin-6(9H)-one;

(10) 2-amino-9-((2R,3R,4S,5S)-4-((2-((((2R,3S,5R)-5-(2-amino-6-oxo-1H-purin-9(6H)-yl)-3-hydroxytetrahydrofuran-2-yl)methyl)amino)-1,1,1,3,3,3-hexafluoropropan-2-yl)amino)-3-hydroxy-5-(hydroxymethyl)tetrahydrofuran-2-yl)-1H-purin-6(9H)-one;

(11) 2-amino-9-((2R,3R,4S,5S)-4-(((((2R,3S,5R)-5-(2-amino-6-oxo-1H-purin-9(6H)-yl)-3-hydroxytetrahydrofuran-2-yl)methyl)amino)dimethylsilyl)amino)-3-hydroxy-5-(hydroxymethyl)tetrahydrofuran-2-yl)-1H-purin-6(9H)-one;

(12) 1-(((2R,3S,5R)-5-(2-amino-6-oxo-1H-purin-9(6H)-yl)-3-hydroxytetrahydrofuran-2-yl)methyl)-3-((2S,3S,4R,5R)-5-(2-amino-6-oxo-1H-purin-9(6H)-yl)-4-hydroxy-2-(hydroxymethyl)tetrahydrofuran-3-yl)urea;

(13) 2-amino-9-((2R,3R,4S,5R)-5-((1-((2S,3S,5R)-5-(2-amino-6-oxo-1H-purin-9(6H)-yl)-2-(hydroxymethyl)tetrahydrofuran-3-yl)-1H-1,2,3-triazol-4-yl)methyl)-3,4-dihydroxytetrahydrofuran-2-yl)-1H-purin-6(9H)-one;

(14) 2-amino-9-((2R,3R,4S,5R)-5-(1-((2S,3S,5R)-5-(2-amino-6-oxo-1H-purin-9(6H)-yl)-2-(hydroxymethyl)tetrahydrofuran-3-yl)-1H-1,2,3-triazol-4-yl)-3,4-dihydroxytetrahydrofuran-2-yl)-1H-purin-6(9H)-one;

(15) 2-amino-9-((2R,3R,4S,5S)-5-(4-((((2R,3S,5R)-5-(2-amino-6-oxo-1H-purin-9(6H)-yl)-2-(hydroxymethyl)tetrahydrofuran-3-yl)oxy)methyl)-1H-1,2,3-triazol-1-yl)-3,4-dihydroxytetrahydrofuran-2-yl)-1H-purin-6(9H)-one;

(16) 2-amino-9-((2R,3R,4S,5R)-5-(2-(2-((2S,3S,5R)-5-(2-amino-6-oxo-1H-purin-9(6H)-yl)-2-(hydroxymethyl)tetrahydrofuran-3-yl)hydrazinyl)ethyl)-3,4-dihydroxytetrahydrofuran-2-yl)-1H-purin-6(9H)-one;

(17) 2-amino-9-((2R,3R,4S,5R)-5-(2-((((2R,3S,5R)-5-(2-amino-6-oxo-1H-purin-9(6H)-yl)-2-(hydroxymethyl)tetrahydrofuran-3-yl)oxy)amino)ethyl)-3,4-dihydroxytetrahydrofuran-2-yl)-1H-purin-6(9H)-one;

(18) 2-amino-9-((2R,3R,4S,5R)-5-(2-((2S,3S,5R)-5-(2-amino-6-oxo-1H-purin-9(6H)-yl)-2-(hydroxymethyl)tetrahydrofuran-3-yl)hydrazinyl)methyl)-3,4-dihydroxytetrahydrofuran-2-yl)-1H-purin-6(9H)-one;

(19) 2-amino-9-((2R,3R,4S,5R)-5-(((((2R,3S,5R)-5-(2-amino-6-oxo-1H-purin-9(6H)-yl)-2-(hydroxymethyl)tetrahydrofuran-3-yl)oxy)amino)methyl)-3,4-dihydroxytetrahydrofuran-2-yl)-1H-purin-6(9H)-one;

(20) 3-(((2S,3S,5R)-5-(2-amino-6-oxo-1H-purin-9(6H)-yl)-2-(hydroxymethyl)tetrahydrofuran-3-yl)amino)-4-(((2R,3S,4R,5R)-5-(2-amino-6-oxo-1H-purin-9(6H)-yl)-3,4-dihydroxytetrahydrofuran-2-yl)methyl)amino)cyclobut-3-ene-1,2-dione;

(21) 2-amino-9-((2R,3R,4S,5R)-5-(((2-(((2S,3S,5R)-5-(2-amino-6-oxo-1H-purin-9(6H)-yl)-2-(hydroxymethyl)tetrahydrofuran-3-yl)amino)propan-2-yl)amino)methyl)-3,4-dihydroxytetrahydrofuran-2-yl)-1H-purin-6(9H)-one;

(22) 2-amino-9-((2R,3R,4S,5R)-5-(((2-(((2S,3S,5R)-5-(2-amino-6-oxo-1H-purin-9(6H)-yl)-2-(hydroxymethyl)tetrahydrofuran-3-yl)amino)-1,1,1,3,3,3-hexafluoropropan-2-yl)amino)methyl)-3,4-dihydroxytetrahydrofuran-2-yl)-1H-purin-6(9H)-one;

(23) 2-amino-9-((2R,3R,4S,5R)-5-(((((2S,3S,5R)-5-(2-amino-6-oxo-1H-purin-9(6H)-yl)-2-(hydroxymethyl)tetrahydrofuran-3-yl)amino)dimethylsilyl)amino)methyl)-3,4-dihydroxytetrahydrofuran-2-yl)-1H-purin-6(9H)-one;

(24) 1-((2S,3S,5R)-5-(2-amino-6-oxo-1H-purin-9(6H)-yl)-2-(hydroxymethyl)tetrahydrofuran-3-yl)-3-(((2R,3S,4R,5R)-5-(2-amino-6-oxo-1H-purin-9(6H)-yl)-3,4-dihydroxytetrahydrofuran-2-yl)methyl)urea;

(25) 2-amino-9-((2R,4S,5R)-5-((1-((2S,3S,5R)-5-(2-amino-6-oxo-1H-purin-9(6H)-yl)-2-(hydroxymethyl)tetrahydrofuran-3-yl)-1H-1,2,3-triazol-4-yl)methyl)-4-hydroxytetrahydrofuran-2-yl)-1H-purin-6(9H)-one;

(26) 2-amino-9-((2R,4S,5R)-5-(1-((2S,3S,5R)-5-(2-amino-6-oxo-1H-purin-9(6H)-yl)-2-(hydroxymethyl)tetrahydrofuran-3-yl)-1H-1,2,3-triazol-4-yl)-4-hydroxytetrahydrofuran-2-yl)-1H-purin-6(9H)-one;

(27) 2-amino-9-((2R,4S,5R)-5-((4-((((2R,3S,5R)-5-(2-amino-6-oxo-1H-purin-9(6H)-yl)-2-(hydroxymethyl)tetrahydrofuran-3-yl)oxy)methyl)-1H-1,2,3-triazol-1-yl)methyl)-4-hydroxytetrahydrofuran-2-yl)-1H-purin-6(9H)-one;

(28) 2-amino-9-((2R,4S,5R)-5-(2-(2-((2S,3S,5R)-5-(2-amino-6-oxo-1H-purin-9(6H)-yl)-2-(hydroxymethyl)tetrahydrofuran-3-yl)hydrazinyl)ethyl)-4-hydroxytetrahydrofuran-2-yl)-1H-purin-6(9H)-one;

(29) 2-amino-9-((2R,4S,5R)-5-(2-((((2R,3S,5R)-5-(2-amino-6-oxo-1H-purin-9(6H)-yl)-2-(hydroxymethyl)tetrahydrofuran-3-yl)oxy)amino)ethyl)-4-hydroxytetrahydrofuran-2-yl)-1H-purin-6(9H)-one;

(30) 3-(((2S,3S,5R)-5-(2-amino-6-oxo-1H-purin-9(6H)-yl)-2-(hydroxymethyl)tetrahydrofuran-3-yl)amino)-4-((((2R,3S,5R)-5-(2-amino-6-oxo-1H-purin-9(6H)-yl)-3-hydroxytetrahydrofuran-2-yl)methyl)amino)cyclobut-3-ene-1,2-dione;

(31) 2-amino-9-((2R,4S,5R)-5-(((((2R,3S,5R)-5-(2-amino-6-oxo-1H-purin-9(6H)-yl)-2-(hydroxymethyl)tetrahydrofuran-3-yl)oxy)amino)methyl)-4-hydroxytetrahydrofuran-2-yl)-1H-purin-6(9H)-one;

(32) 2-amino-9-((2R,4S,5R)-5-(((2-(((2S,3S,5R)-5-(2-amino-6-oxo-1H-purin-9(6H)-yl)-2-(hydroxymethyl)tetrahydrofuran-3-yl)amino)propan-2-yl)amino)methyl)-4-hydroxytetrahydrofuran-2-yl)-1H-purin-6(9H)-one;

(33) 2-amino-9-((2R,4S,5R)-5-(((2-(((2S,3S,5R)-5-(2-amino-6-oxo-1H-purin-9(6H)-yl)-2-(hydroxymethyl)tetrahydrofuran-3-yl)amino)-1,1,1,3,3,3-hexafluoropropan-2-yl)amino)methyl)-4-hydroxytetrahydrofuran-2-yl)-1H-purin-6(9H)-one;

(34) 2-amino-9-((2R,4S,5R)-5-(((((2S,3S,5R)-5-(2-amino-6-oxo-1H-purin-9(6H)-yl)-2-(hydroxymethyl)tetrahydrofuran-3-yl)amino)dimethylsilyl)amino)methyl)-4-hydroxytetrahydrofuran-2-yl)-1H-purin-6(9H)-one;

(35) 1-((2S,3S,5R)-5-(2-amino-6-oxo-1H-purin-9(6H)-yl)-2-(hydroxymethyl)tetrahydrofuran-3-yl)-3-(((2R,3S,5R)-5-(2-amino-6-oxo-1H-purin-9(6H)-yl)-3-hydroxytetrahydrofuran-2-yl)methyl)urea;

(36) 2-amino-9-((2R,3R,4S,5S)-4-(4-(((2R,3S,4R,5R)-5-(2-amino-6-oxo-1H-purin-9(6H)-yl)-3,4-dihydroxytetrahydrofuran-2-yl)methyl)-1H-1,2,3-triazol-1-yl)-3-hydroxy-5-(hydroxymethyl)tetrahydrofuran-2-yl)-1H-purin-6(9H)-one;

(37) 2-amino-9-((2R,3R,4S,5S)-4-(4-((2R,3S,4R,5R)-5-(2-amino-6-oxo-1H-purin-9(6H)-yl)-3,4-dihydroxytetrahydrofuran-2-yl)-1H-1,2,3-triazol-1-yl)-3-hydroxy-5-(hydroxymethyl)tetrahydrofuran-2-yl)-1H-purin-6(9H)-one;

(38) 2-amino-9-((2R,3R,4S,5R)-5-((4-((((2R,3S,5R)-5-(2-amino-6-oxo-1H-purin-9(6H)-yl)-2-(hydroxymethyl)tetrahydrofuran-3-yl)oxy)methyl)-1H-1,2,3-triazol-1-yl)methyl)-3,4-dihydroxytetrahydrofuran-2-yl)-1H-purin-6(9H)-one;

(39) 2-amino-9-((2R,3R,4S,5S)-4-(2-(2-((2R,3S,4R,5R)-5-(2-amino-6-oxo-1H-purin-9(6H)-yl)-3,4-dihydroxytetrahydrofuran-2-yl)ethyl)hydrazinyl)-3-hydroxy-5-(hydroxymethyl)tetrahydrofuran-2-yl)-1H-purin-6(9H)-one;

(40) 2-amino-9-((2R,3R,4S,5R)-4-(((2-((2R,3S,4R,5R)-5-(2-amino-6-oxo-1H-purin-9(6H)-yl)-3,4-dihydroxytetrahydrofuran-2-yl)ethyl)amino)oxy)-3-hydroxy-5-(hydroxymethyl)tetrahydrofuran-2-yl)-1H-purin-6(9H)-one;

(41) 2-amino-9-((2R,3R,4S,5S)-4-(2-(((2R,3S,4R,5R)-5-(2-amino-6-oxo-1H-purin-9(6H)-yl)-3,4-dihydroxytetrahydrofuran-2-yl)methyl)hydrazinyl)-3-hydroxy-5-(hydroxymethyl)tetrahydrofuran-2-yl)-1H-purin-6(9H)-one;

(42) 3-(((((2R,3S,4R,5R)-5-(2-amino-6-oxo-1H-purin-9(6H)-yl)-3,4-dihydroxytetrahydrofuran-2-yl)methyl)amino)-4-(((2S,3S,4R,5R)-5-(2-amino-6-oxo-1H-purin-9(6H)-yl)-4-hydroxy-2-(hydroxymethyl)tetrahydrofuran-3-yl)amino)cyclobut-3-ene-1,2-dione;

(43) 2-amino-9-((2R,3R,4S,5S)-4-((2-((((2R,3S,4R,5R)-5-(2-amino-6-oxo-1H-purin-9(6H)-yl)-3,4-dihydroxytetrahydrofuran-2-yl)methyl)amino)propan-2-yl)amino)-3-hydroxy-5-(hydroxymethyl)tetrahydrofuran-2-yl)-1H-purin-6(9H)-one;

(44) 2-amino-9-((2R,3R,4S,5S)-4-((2-((((2R,3S,4R,5R)-5-(2-amino-6-oxo-1H-purin-9(6H)-yl)-3,4-dihydroxytetrahydrofuran-2-yl)methyl)amino)-1,1,1,3,3,3-hexafluoropropan-2-yl)amino)-3-hydroxy-5-(hydroxymethyl)tetrahydrofuran-2-yl)-1H-purin-6(9H)-one;

(45) 2-amino-9-((2R,3R,4S,5S)-4-((((((2R,3S,4R,5R)-5-(2-amino-6-oxo-1H-purin-9(6H)-yl)-3,4-dihydroxytetrahydrofuran-2-yl)methyl)amino)dimethylsilyl)amino)-3-hydroxy-5-(hydroxymethyl)tetrahydrofuran-2-yl)-1H-purin-6(9H)-one;

(46) 1-(((2R,3S,4R,5R)-5-(2-amino-6-oxo-1H-purin-9(6H)-yl)-3,4-dihydroxytetrahydrofuran-2-yl)methyl)-3-((2S,3S,4R,5R)-5-(2-amino-6-oxo-1H-purin-9(6H)-yl)-4-hydroxy-2-(hydroxymethyl)tetrahydrofuran-3-yl)urea;

(47) 2-amino-9-((2R,3R,4S,5S)-4-((((((2R,3S,5R)-5-(2-amino-6-oxo-1H-purin-9(6H)-yl)-3-hydroxytetrahydrofuran-2-yl)methyl)sulfamide)-3-hydroxy-5-(hydroxymethyl)tetrahydrofuran-2-yl)-1H-purin-6(9H)-one:

(48) 2-amino-9-((2R,3R,4S,5R)-5-((((((2S,3S,5R)-5-(2-amino-6-oxo-1H-purin-9(6H)-yl)-2-(hydroxymethyl)tetrahydrofuran-3-yl)sulfamide)methyl)-3,4-dihydroxytetrahydrofuran-2-yl)-1H-purin-6(9H)-one:

(49) 2-amino-9-((2R,4S,5R)-5-((((((2S,3S,5R)-5-(2-amino-6-oxo-1H-purin-9(6H)-yl)-2-(hydroxymethyl)tetrahydrofuran-3-yl)sulfamide)methyl)-4-hydroxytetrahydrofuran-2-yl)-1H-purin-6(9H)-one:

(50) 2-amino-9-((2R,3R,4S,5S)-4-((((((2R,3S,4R,5R)-5-(2-amino-6-oxo-1H-purin-9(6H)-yl)-3,4-dihydroxytetrahydrofuran-2-yl)methyl)sulfamide)-3-hydroxy-5-(hydroxymethyl)tetrahydrofuran-2-yl)-1H-purin-6(9H)-one:

(51) ((2S,3S,4R,5R)-5-(2-amino-6-oxo-1H-purin-9(6H)-yl)-3-(4-(((2R,3S,4R,5R)-5-(2-amino-6-oxo-1H-purin-9(6H)-yl)-3,4-dihydroxytetrahydrofuran-2-yl)methyl)-1H-1,2,3-triazol-1-yl)-4-hydroxytetrahydrofuran-2-yl)methyl 5-((3aS,4S,6aR)-2-oxohexahydro-1H-thieno[3,4-d]imidazol-4-yl)pentanoate;

(52) (2R,3S,4R,5R)-5-(2-amino-6-oxo-1H-purin-9(6H)-yl)-2-((1-((2S,3S,4R,5R)-5-(2-amino-6-oxo-1H-purin-9(6H)-yl)-4-hydroxy-2-(hydroxymethyl)tetrahydrofuran-3-yl)-1H-1,2,3-triazol-4-yl)methyl)-4-hydroxytetrahydrofuran-3-yl 5-((3aS,4S,6aR)-2-oxohexahydro-1H-thieno[3,4-d]imidazol-4-yl)pentanoate;

(53) 2-amino-9-((2R,3R,4S,5R)-5-((1-((2S,3S,4R,5R)-5-(2-amino-6-oxo-1H-purin-9(6H)-yl)-2-((((4R)-4-(3-chlorophenyl)-2-oxido-1,3,2-dioxaphosphinan-2-yl)oxy)

methyl)-4-hydroxytetrahydrofuran-3-yl)-1H-1,2,3-triazol-4-yl)methyl)-3,4-dihydroxytetrahydrofuran-2-yl)-1H-purin-6(9H)-one; and

(54) ((2S,3S,4R,5R)-5-(2-amino-6-oxo-1H-purin-9(6H)-yl)-3-(4-(((2R,3S,4R,5R)-5-(2-amino-6-oxo-1H-purin-9(6H)-yl)-3,4-dihydroxytetrahydrofuran-2-yl)methyl)-1H-1,2,3-triazol-1-yl)-4-hydroxytetrahydrofuran-2-yl)methyl dihydrogen phosphate.

In another particular embodiment of the invention, a compound of Formula I, or a salt thereof, is selected from the group consisting of:

(8) 3-((((2R,3S,5R)-5-(2-amino-6-oxo-1H-purin-9(6H)-yl)-3-hydroxytetrahydrofuran-2-yl)methyl)amino)-4-(((2S,3S,4R,5R)-5-(2-amino-6-oxo-1H-purin-9(6H)-yl)-4-hydroxy-2-(hydroxymethyl)tetrahydrofuran-3-yl)amino)cyclobut-3-ene-1,2-dione;

(42) 3-((((2R,3S,4R,5R)-5-(2-amino-6-oxo-1H-purin-9(6H)-yl)-3,4-dihydroxytetrahydrofuran-2-yl)methyl)amino)-4-(((2S,3S,4R,5R)-5-(2-amino-6-oxo-1H-purin-9(6H)-yl)-4-hydroxy-2-(hydroxymethyl)tetrahydrofuran-3-yl)amino)cyclobut-3-ene-1,2-dione;

and salts thereof.

In another particular embodiment of the invention comprises a compound of Formula I, wherein the compound is:

(42) 3-((((2R,3S,4R,5R)-5-(2-amino-6-oxo-1H-purin-9(6H)-yl)-3,4-dihydroxytetrahydrofuran-2-yl)methyl)amino)-4-(((2S,3S,4R,5R)-5-(2-amino-6-oxo-1H-purin-9(6H)-yl)-4-hydroxy-2-(hydroxymethyl)tetrahydrofuran-3-yl)amino)cyclobut-3-ene-1,2-dione, or salt thereof In another aspect, the invention is directed to a compound of Formula II, or a salt thereof,

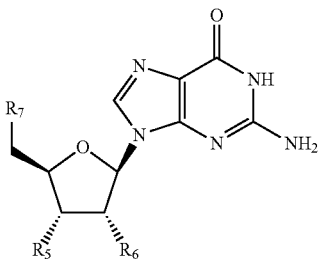

II wherein:

$R_5$ is selected from the group consisting of —O—$NH_2$; —$NH_2$, —NH—S(=O)$_2$—$NH_2$, —$N_3^-$, —NH—$NH_2$, trifluoromethylsulfonyl, —(C=O)—H, —C≡CH and —O—$CH_2$—C≡CH;

$R_6$ is selected from the group consisting of hydrogen, hydroxyl and —O—Si($CH_3$)$_3$; and $R_7$ is selected from the group consisting of hydroxyl, —O—$CH_2$—C≡CH and —O$PO_3H_2$.

The compounds of Formula II are intermediates in the preparation of compounds of Formula Ia, described below.

Another particular embodiment of the invention comprises a compound of Formula II, or a salt thereof, wherein $R_6$ is selected from the group consisting of hydrogen and hydroxyl; and $R_7$ is selected from the group consisting of hydroxyl and —O—Si($CH_3$)$_3$.

In one aspect, the invention is a compound of Formula III, or a salt thereof,

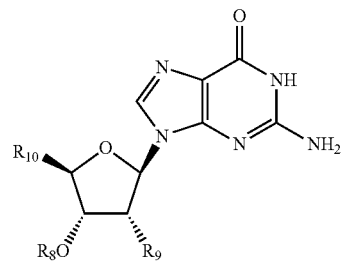

III wherein $R_8$ is selected from the group consisting of hydrogen and —$PO_3H_2$;

$R_9$ is selected form the group consisting of hydrogen, hydroxyl and —O$PO_3H_2$;

$R_{10}$ is selected form the group consisting of —$CH_2$—C(=O)H, —$CH_2$—C≡CH, —C(=O)H, —C≡CH, —O$NH_2$, —($CH_2$)—$N_3^-$, —($CH_2$)-halide; —($CH_2$)—NH—$NH_2$ and —($CH_2$)—$NH_2$.

The compounds of Formula III are intermediates in the preparation of compounds of Formula Ia.

Another particular embodiment of the invention comprises a compound of Formula III, or a salt thereof, wherein $R_8$ is hydrogen; $R_9$ selected from the group of hydrogen and hydroxyl; and $R_{10}$ is selected from the group consisting of —($CH_2$)-halide; —($CH_2$)—$N_3^-$; —($CH_2$)—NH—$NH_2$; —O$NH_2$; and —($CH_2$)—$NH_2$.

III. METHODS FOR PREPARING COMPOUNDS OF THE INVENTION AND INTERMEDIATES USEFUL IN THE SYNTHESIS OF COMPOUNDS OF THE INVENTION

There are provided processes for preparing compounds according to Formula I, intermediates that are useful in the preparation of such compounds, and processes for preparing such intermediates.

In one embodiment, a process for preparing a compound of Formula Ia is provided. The compounds of Formula Ia are intermediates in the preparation of Formula I compounds, in the case where $R_6$ is —O—Si($CH_3$)$_3$ in Formula Ia. The —O—Si($CH_3$)$_3$ may then be converted to hydrogen, hydroxyl, ($C_1$-$C_6$)alkyl, ($C_1$-$C_6$)alkyloxy, or —O$PO_3H_2$ to generate a compound according to Formula I. The compounds of Formula Ia when $R_6$ is hydrogen or hydroxyl comprise a subgenus of Formula I.

The process for preparing a compound of Formula Ia comprises:

reacting a compound of Formula II and compound of Formula III with a coupling agent to form a compound of Formula Ia:

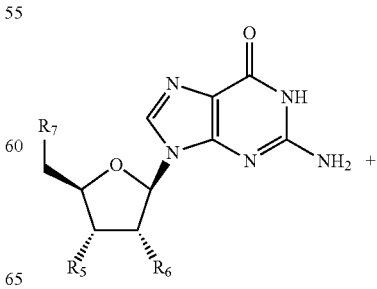

Formula II

15
-continued

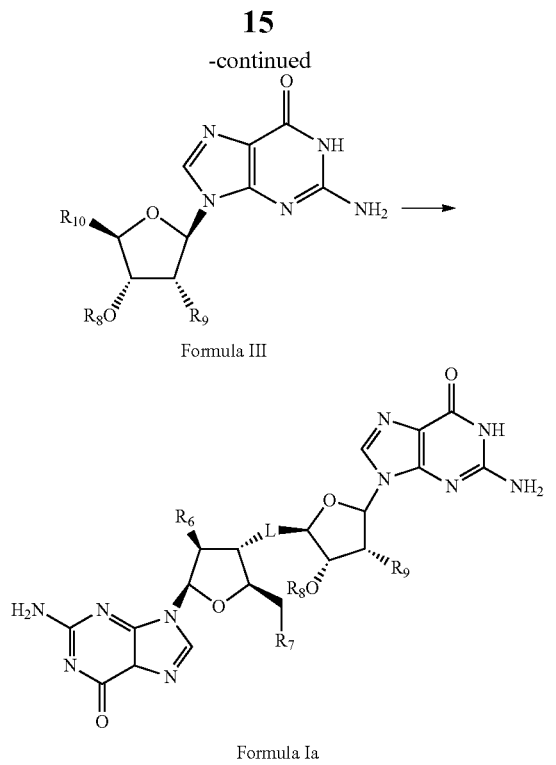

Formula III

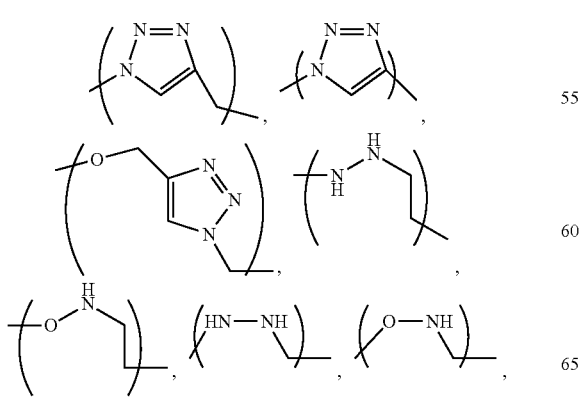

Formula Ia wherein:

$R_5$ is selected from the group consisting of —O—NH$_2$; —NH$_2$, —NH—S(=O)$_2$—NH$_2$, —N$_3^-$, —NH—NH$_2$, trifluoromethylsulfonyl, —(C=O)—H; —C≡CH and —O—CH$_2$—C≡CH;

$R_6$ is selected from the group consisting of hydrogen, hydroxyl and —O—Si(CH$_3$)$_3$;

$R_7$ is selected from the group consisting of hydroxyl and —OPO$_3$H$_2$;

$R_8$ is selected from the group consisting of hydrogen and —PO$_3$H$_2$;

$R_9$ is selected form the group consisting of hydrogen, hydroxyl and —OPO$_3$H$_2$;

$R_{10}$ is selected form the group consisting of —CH$_2$—C(=O)H, —CH$_2$—C≡CH; —C(=O)H, —C≡CH, —(CH$_2$)-halide, —(CH$_2$)—N$_3^-$, —(CH$_2$)—NH—NH$_2$, —ONH$_2$ and —(CH$_2$)—NH$_2$;

L is selected from the group consisting of:

16
-continued

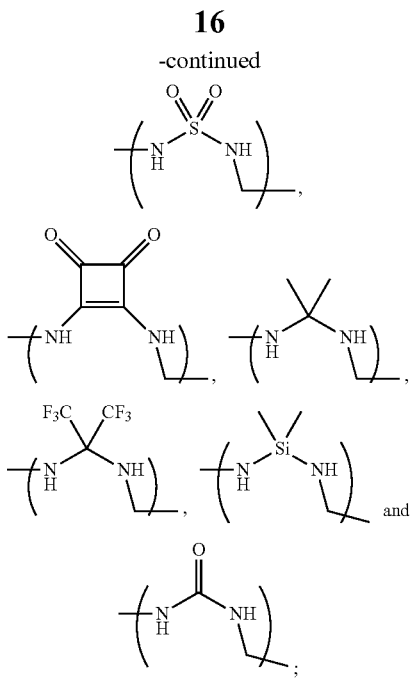

In another embodiment, a process for preparing a compound of Formula I is provided. The process comprises:

reacting a compound of Formula Ib with the appropriate ester or phosphoester to from a compound of Formula I,

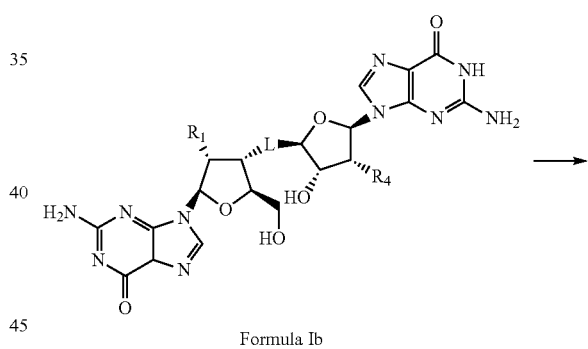

Formula Ib

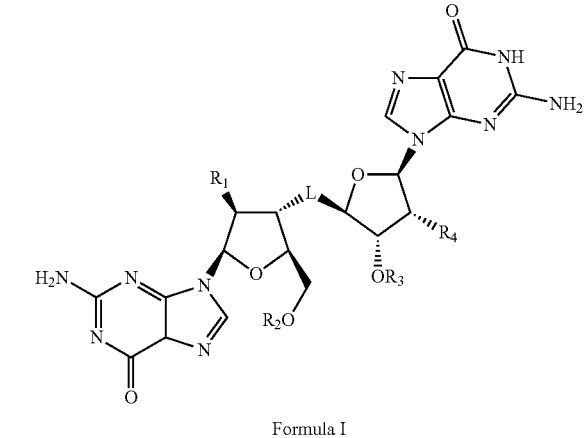

Formula I wherein:

L is selected from the group consisting of:

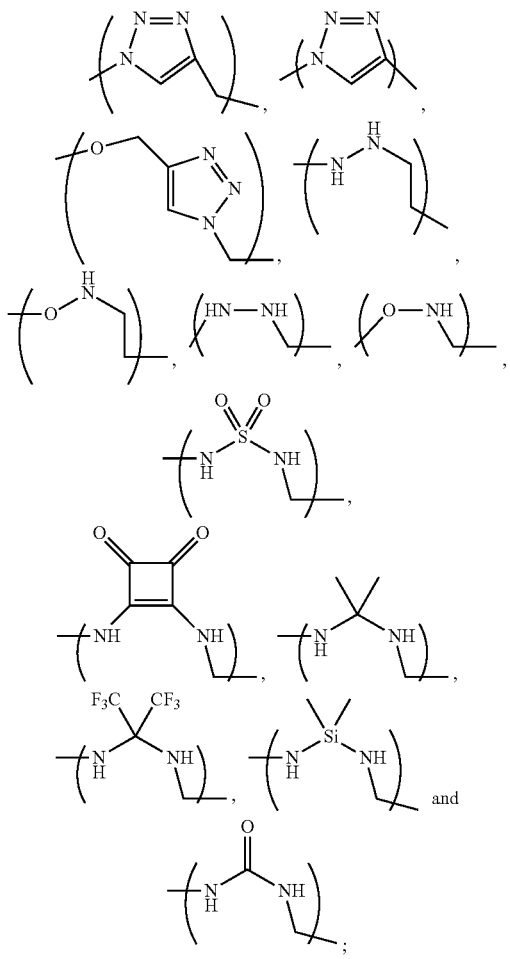

$R_1$ is selected from the group consisting of hydrogen, hydroxyl, $(C_1\text{-}C_6)$alkyl, $(C_1\text{-}C_6)$alkyloxy and $-OPO_3H_2$;

$R_2$ is selected from the group consisting of:
hydrogen,
$-PO_3H_2$,

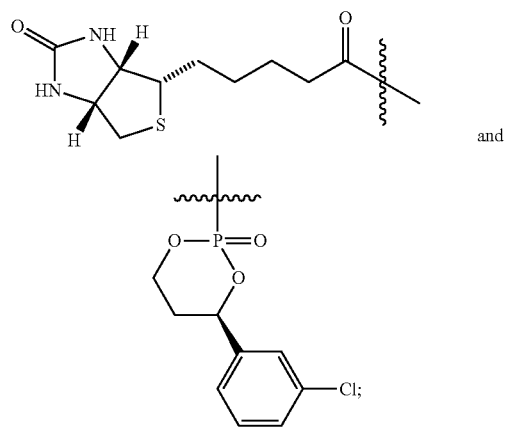

$R_3$ is selected from the group consisting of:
hydrogen,
$-PO_3H_2$,

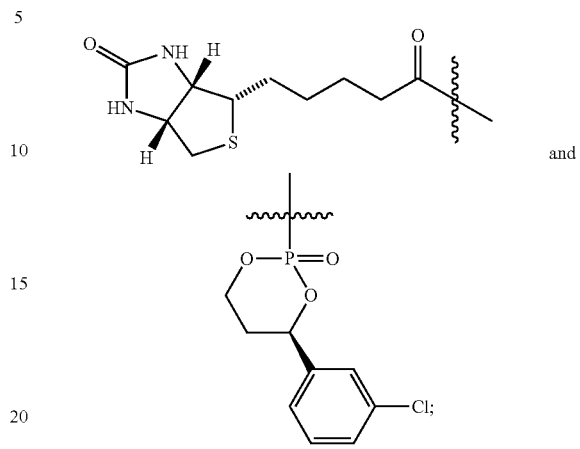

and $R_4$ is selected from the group consisting of hydrogen, hydroxyl, $(C_1\text{-}C_6)$alkyl, $(C_1\text{-}C_6)$alkyloxy and $-OPO_3H_2$.

IV. TREATMENT OF BACTERIAL INFECTIONS USING COMPOUNDS OF THE INVENTION AND USING THE COMPOUNDS OF THE INVENTIONS AS PROBES

According to another embodiment of the invention, a method of treating an individual suffering from a bacterial infection is provided, comprising administering to said individual an effective amount of at least one compound according to Formula I, or a pharmaceutically acceptable salt thereof, either alone, or in combination with a pharmaceutically acceptable carrier.

The compounds according to the invention may be administered to individuals (mammals, including animals and humans) afflicted with a bacterial infection. In a particular embodiment of the invention, the individual treated is a human.

The compounds are believed effective against a broad range of bacteria, including but not limited to the following: *Pseudomonas aeruginosa; Pseudomonas fluorescens; Yersinas pestis; Vibrio cholerae; Salmonella enterica; Salmonella Typhimurium; Legionella pneumophia; Brucella melitensis; Bordetella pertussis; Streptococcus mutans; Acinetobacter baumannii; Staphylococcus aureus; Escherichia coli;* and *Bacillus anthracis*.

In embodiments, the method comprises administering to the individual an effective amount of at least one compound or a pharmaceutically acceptable salt thereof, selected from the group consisting of:

(8) 3-((((2R,3S,5R)-5-(2-amino-6-oxo-1H-purin-9(6H)-yl)-3-hydroxytetrahydrofuran-2-yl)methyl)amino)-4-(((2S,3S,4R,5R)-5-(2-amino-6-oxo-1H-purin-9(6H)-yl)-4-hydroxy-2-(hydroxymethyl)tetrahydrofuran-3-yl)amino)cyclobut-3-ene-1,2-dione;

(42) 3-((((2R,3S,4R,5R)-5-(2-amino-6-oxo-1H-purin-9(6H)-yl)-3,4-dihydroxytetrahydrofuran-2-yl)methyl)amino)-4-(((2S,3S,4R,5R)-5-(2-amino-6-oxo-1H-purin-9(6H)-yl)-4-hydroxy-2-(hydroxymethyl)tetrahydrofuran-3-yl)amino)cyclobut-3-ene-1,2-dione.

In an aspect of the method, a method is provided for preventing and/or reducing the risk of bacterial infection in individuals, comprising administering to the individual an effective amount of a compound, or a pharmaceutically acceptable salt thereof, according to Formula I.

In a further aspect of the method of bacterial infection prevention/reduction, the compound of Formula I is 3-((((2R,3S,4R,5R)-5-(2-amino-6-oxo-1H-purin-9(6H)-yl)-3,4-dihydroxytetrahydrofuran-2-yl)methyl)amino)-4-(((2S,3S,4R,5R)-5-(2-amino-6-oxo-1H-purin-9(6H)-yl)-4-hydroxy-2-(hydroxymethyl)tetrahydrofuran-3-yl)amino) cyclobut-3-ene-1,2-dione, or a pharmaceutically acceptable salt thereof.

According to another embodiment of the invention, the compounds of the invention are utilized as probes to identifying pGpG-binding domains in bacteria. The method comprises the steps of contacting a compound of claim 1 or salt thereof with a bacteria or fraction thereof and detecting the binding of said compound or salt with a pGpG-binding domain in the bacteria or fraction thereof.

In certain embodiments, the probe compound is:
((2S,3S,4R,5R)-5-(2-amino-6-oxo-1H-purin-9(6H)-yl)-3-(4-(((2R,3S,4R,5R)-5-(2-amino-6-oxo-1H-purin-9(6H)-yl)-3,4-dihydroxytetrahydrofuran-2-yl)methyl)-1H-1,2,3-triazol-1-yl)-4-hydroxytetrahydrofuran-2-yl)methyl 5-((3aS,4S,6aR)-2-oxohexahydro-1H-thieno[3,4-d]imidazol-4-yl)pentanoate, or
(2R,3S,4R,5R)-5-(2-amino-6-oxo-1H-purin-9(6H)-yl)-2-((1-((2S,3S,4R,5R)-5-(2-amino-6-oxo-1H-purin-9(6H)-yl)-4-hydroxy-2-(hydroxymethyl)tetrahydrofuran-3-yl)-1H-1,2,3-triazol-4-yl)methyl)-4-hydroxytetrahydrofuran-3-yl 5-((3aS,4S,6aR)-2-oxohexahydro-1H-thieno[3,4-d] imidazol-4-yl)pentanoate.

In certain embodiments, the bacteria so probed is selected from the group consisting of: *Pseudomonas aeruginosa; Pseudomonas fluorescens; Yersinas pestis; Vibrio cholerae; Salmonella enterica; Salmonella typhimurium; Legionella pneumophia; Brucella melitensis; Bordetella pertussis; Streptococcus mutans; Acinetobacter baumannii; Staphylococcus aureus; Escherichia coli*; and *Bacillus anthracis*. The probe compound may be detectably labeled to indicate its binding with pGpG-binding domains in the bacteria.

V. SALTS OF COMPOUNDS ACCORDING TO THE INVENTION

The compounds of the present invention may take the form of salts when appropriately substituted with groups or atoms capable of forming salts. Such groups and atoms are well known to those of ordinary skill in the art of organic chemistry. The term "salts" embraces addition salts of free acids or free bases which are compounds of the invention. The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts.

All of these salts may be prepared by conventional means from the corresponding compound according to Formula I by reacting, for example, the appropriate acid or base with the compound according to Formula I. Preferably the salts are in crystalline form, and preferably prepared by crystallization of the salt from a suitable solvent. The person skilled in the art will know how to prepare and select suitable salt forms for example, as described in *Handbook of Pharmaceutical Salts: Properties, Selection, and Use* By P. H. Stahl and C. G. Wermuth (Wiley-VCH 2002).

VI. PHARMACEUTICAL COMPOSITIONS

The compounds of the invention may be administered in the form of a pharmaceutical composition, in combination with a pharmaceutically acceptable carrier. The active ingredient or agent in such formulations (i.e., a compound of Formula I) may comprise from 0.1 to 99.99 weight percent of the formulation. "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18th Edition (1990), Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propylparaben, and chlorobutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of a compound according to the invention to obtain therapeutic benefit for treatment of a bacterial infection will, of course, be determined by the particular circumstances of the individual patient including the size, weight, age and sex of the patient, the nature and stage of the bacterial infection, the aggressiveness of the bacterial infection, and the route of administration of the compound.

For example, a daily dosage from about 0.05 to about 50 mg/kg/day may be utilized, more preferably from about 0.1 to about 10 mg/kg/day. Higher or lower doses are also contemplated as it may be necessary to use dosages outside these ranges in some cases. The daily dosage may be divided, such as being divided equally into two to four times per day daily dosing. The compositions are preferably formulated in a unit dosage form, each dosage containing from about 1 to about 500 mg, more typically, about 10 to about 100 mg of active agent per unit dosage. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The pharmaceutical compositions of the present invention may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

The pharmaceutical compositions can also be formulated to provide for topical compositions and treatments using suitable carriers and controlled-release preparations.

The following discusses controlled release systems that may be utilized in the practice of the invention. U.S. Pat. No. 5,674,533 discloses controlled-release pharmaceutical compositions in liquid dosage forms for the administration of moguisteine, a potent peripheral antiitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,733,566 describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

VII. ROUTES OF ADMINISTRATION OF COMPOUNDS AND COMPOSITIONS OF THE INVENTION

The compounds of Formula I may be administered by any route, including oral, topical, rectal, sublingual, and parenteral administration. Parenteral administration includes, for example, intravenous, intramuscular, intraarterial, intraperitoneal, intranasal, intravaginal, intravesical (e.g., to the bladder), intradermal, transdermal, topical or subcutaneous administration. Also contemplated within the scope of the invention is the instillation of a drug in the body of the patient in a controlled formulation, with systemic or local release of the drug to occur at a later time. For example, the drug may be localized in a depot for controlled release to the circulation, or for release to a local site of an infection or wound.

One or more compounds useful in the practice of the present inventions may be administered simultaneously, by the same or different routes, or at different times during treatment. The compounds may be administered before, along with, or after other medications, including other antiproliferative compounds.

The treatment may be carried out for as long a period as necessary, either in a single, uninterrupted session, or in discrete sessions. The treating physician will know how to increase, decrease, or interrupt treatment based on patient response. According to one embodiment, treatment is carried out for from about four to about sixteen weeks. The treatment schedule may be repeated as required.

EXAMPLES

The following non-limiting examples are provided to illustrate the invention. The synthetic procedures described as "general methods" describe what it is believed will be typically effective to perform the synthesis indicated. However, the person skilled in the art will appreciate that it may be necessary to vary the procedures for any given embodiment of the invention. For example, reaction monitoring, such as by using thin layer chromatography, or HPLC may be used to determine the optimum reaction time. Products may be purified by conventional techniques that will vary, for example, according to the amount of side products produced and the physical properties of the compounds. On a laboratory scale, recrystallisation from a suitable solvent, column chromatography, normal or reverse phase HPLC, or distillation are all techniques which may be useful. The person skilled in the art will appreciate how to vary the reaction conditions to synthesize any given compound within the scope of the invention without undue experimentation. See, e.g., *Vogel's Textbook of Practical Organic Chemistry*, by A. I. Vogel, et al, *Experimental Organic Chemistry: Standard and Microscale*, by L. M. Harwood et al. ($2^{nd}$ Ed., Blackwell Scientific Publications, 1998), and Advanced Practical Organic Chemistry, by J. Leonard, et al. ($2^{nd}$ Edition, CRC Press 1994).

Preparation of Starting Materials

The compounds prepared according to Table 1 may be utilized as starting materials in the General Procedures that follow, to prepare compounds of Formula I. The following abbreviations are used in Table 1: BuLi: butyllithium; DMF: dimethylformamide; PPh$_3$: triphenylphosphine; TEMPO: (2,2,6,6-tetramethylpiperidin-1-yl)oxyl, PCC: pyridium chlorochromate; DCM: dichloromethane; THF: tetrahydrofuran

TABLE 1

Starting materials for preparation of compounds of Formula I.

| Prep. No. | Starting material compound name and synthetic method for producing same. |
|---|---|
| 1 | 2-amino-9-((2R,3R,4S,5S)-3,4-dihydroxy-5-(iodomethyl)tetrahydrofuran-2-yl)-1H-purin-6(9H)-one. Related procedures can be found in Niewidomski, S. et al., *Org, Biomol. Chem.* 2010, 8, 3488. |

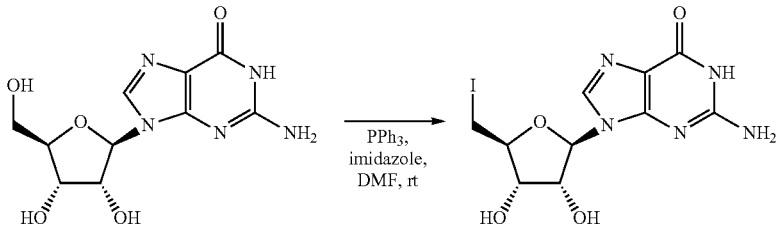 [SMILES: Nc1nc2c(ncn2[C@@H]2O[C@H](CO)[C@@H](O)[C@H]2O)c(=O)[nH]1 ; Nc1nc2c(ncn2[C@@H]2O[C@H](CI)[C@@H](O)[C@H]2O)c(=O)[nH]1]

| 2 | 2-amino-9-((2R,3R,4S,5R)-5-(hydrazinylmethyl)-3,4-dihydroxytetrahydrofuran-2-yl)-1H-purin-6(9H)-one. See, Brear, P. et al., *Chem. Comm.* 2009, 33, 4980. |

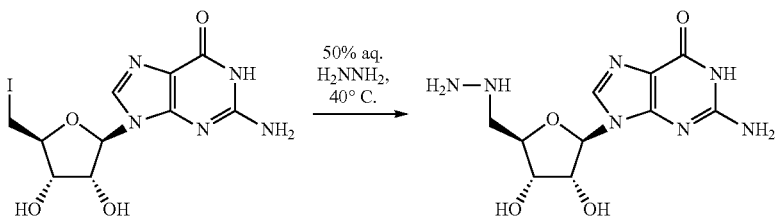 [SMILES: Nc1nc2c(ncn2[C@@H]2O[C@H](CI)[C@@H](O)[C@H]2O)c(=O)[nH]1 ; NNC[C@H]1O[C@@H](n2cnc3c(=O)[nH]c(N)nc32)[C@H](O)[C@@H]1O]

| 3 | 2-amino-9-((2R,3R,4S,5R)-5-((aminooxy)methyl)-3,4-dihydroxytetrahydrofuran-2-yl)-1H-purin-6(9H)-one. See, Ozinskas, A. et al., *J. Org. Chem.* 1986, 51, 5047. |

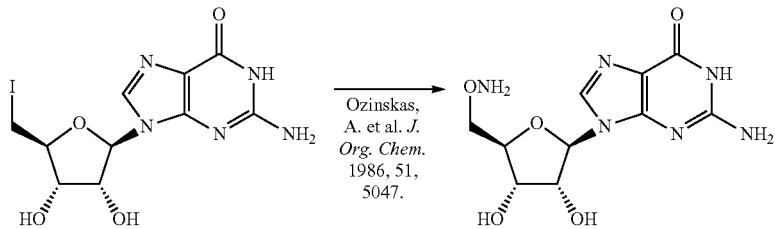

TABLE 1-continued

Starting materials for preparation of compounds of Formula I.

Prep.
No.   Starting material compound name and synthetic method for producing same.

4     2-amino-9-((2R,3R,4S,5R)-5-(azidomethyl)-3,4-dihydroxytetrahydrofuran-2-yl)-1H-purin-6(9H)-
      one. Niewidomski, S. et al., *Org. Biomol. Chem.* 2010, 8, 3488.

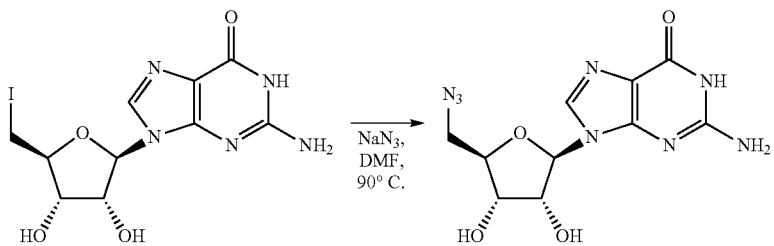 [SMILES: Nc1nc2c(ncn2[C@@H]2O[C@H](CI)[C@@H](O)[C@H]2O)c(=O)[nH]1 ; [N-]=[N+]=NC[C@H]1O[C@@H](n2cnc3c(=O)[nH]c(N)nc32)[C@H](O)[C@@H]1O]

5     2-amino-9-((2R,3R,4S,5R)-5-(aminomethyl)-3,4-dihydroxytetrahydrofuran-2-yl)-1H-purin-6(9H)-
      one. See, Niewidomski, S. et al., *Org. Biomol. Chem.* 2010, 8, 3488.

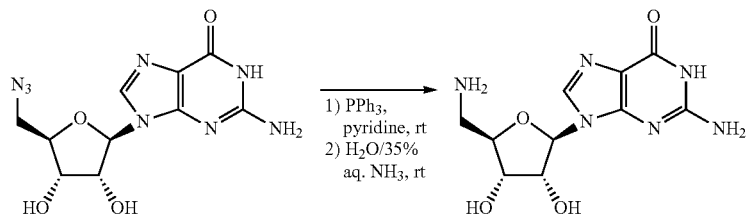 [SMILES: [N-]=[N+]=NC[C@H]1O[C@@H](n2cnc3c(=O)[nH]c(N)nc32)[C@H](O)[C@@H]1O ; NC[C@H]1O[C@@H](n2cnc3c(=O)[nH]c(N)nc32)[C@H](O)[C@@H]1O]

6     (2S,3S,4R,5R)-5-(2-amino-6-oxo-1H-purin-9(6H)-yl)-3,4-dihydroxytetrahydrofuran-2-
      carbaldehyde. See, Angelin, M. et al., *Eur. J. Org. Chem.* 2006, 4323.

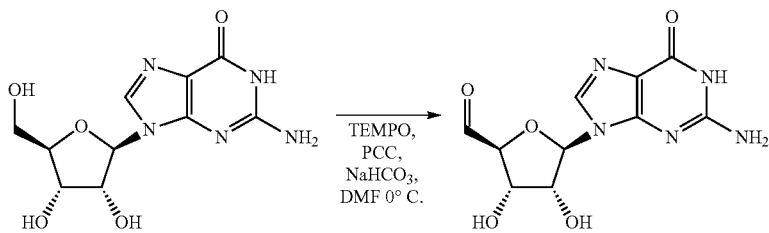 [SMILES: Nc1nc2c(ncn2[C@@H]2O[C@H](CO)[C@@H](O)[C@H]2O)c(=O)[nH]1 ; Nc1nc2c(ncn2[C@@H]2O[C@H](C=O)[C@@H](O)[C@H]2O)c(=O)[nH]1]

7     2-amino-9-((2R,3R,4S,5R)-5-ethynyl-3,4-dihydroxytetrahydrofuran-2-yl)-1H-purin-6(9H)-one.
      See, Pal, A. et al., *J. Org. Chem.* 2001, 66, 9071.

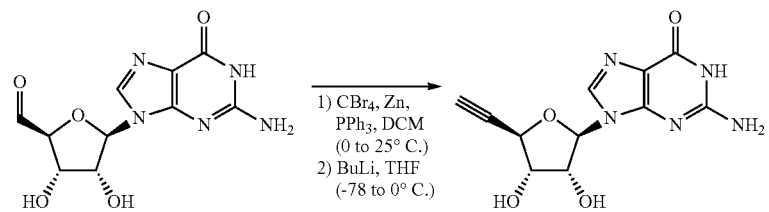 [SMILES: Nc1nc2c(ncn2[C@@H]2O[C@H](C=O)[C@@H](O)[C@H]2O)c(=O)[nH]1 ; C#C[C@H]1O[C@@H](n2cnc3c(=O)[nH]c(N)nc32)[C@H](O)[C@@H]1O]

8     2-((2R,3S,4R,5R)-5-(2-amino-6-oxo-1H-purin-9(6H)-yl)-3,4-dihydroxytetrahydrofuran-2-
      yl)acetaldehyde. See, Douglass, J. et al., *Bioorg. Med. Chem. Lett.* 2008, 18, 2167.

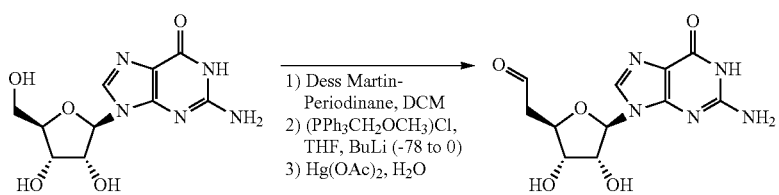 [SMILES: Nc1nc2c(ncn2[C@@H]2O[C@H](CO)[C@@H](O)[C@H]2O)c(=O)[nH]1 ; Nc1nc2c(ncn2[C@@H]2O[C@H](CC=O)[C@@H](O)[C@H]2O)c(=O)[nH]1]

TABLE 1-continued

Starting materials for preparation of compounds of Formula I.

Prep. No. Starting material compound name and synthetic method for producing same.

9  2-((2R,3S,4R,5R)-5-(2-amino-6-oxo-1H-purin-9(6H)-yl)-3,4-dihydroxytetrahydrofuran-2-yl)acetaldehyde. See, Pal, A. et al., *J. Org. Chem.* 2001, 66, 9071.

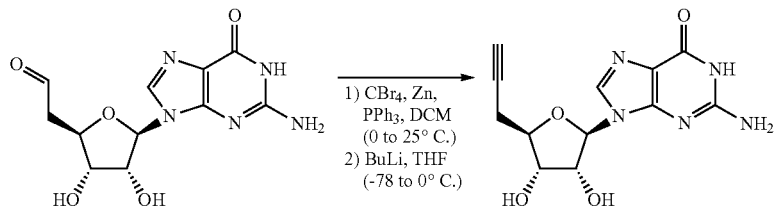 [SMILES: Nc1nc2c(ncn2[C@@H]2O[C@H](CC=O)[C@@H](O)[C@H]2O)c(=O)[nH]1 ; C#CC[C@H]1O[C@@H](n2cnc3c(=O)[nH]c(N)nc32)[C@H](O)[C@@H]1O]

10  2-amino-9-((2R,4S,5S)-4-hydroxy-5-(iodomethyl)tetrahydrofuran-2-yl)-1H-purin-6(9H)-one

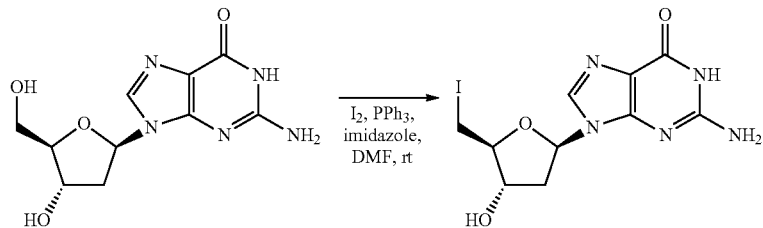 [SMILES: Nc1nc2c(ncn2[C@H]2C[C@H](O)[C@@H](CO)O2)c(=O)[nH]1 ; Nc1nc2c(ncn2[C@H]2C[C@H](O)[C@@H](CI)O2)c(=O)[nH]1]

11  2-amino-9-((2R,4S,5R)-5-(hydrazinylmethyl)-4-hydroxytetrahydrofuran-2-yl)-1H-purin-6(9H)-one

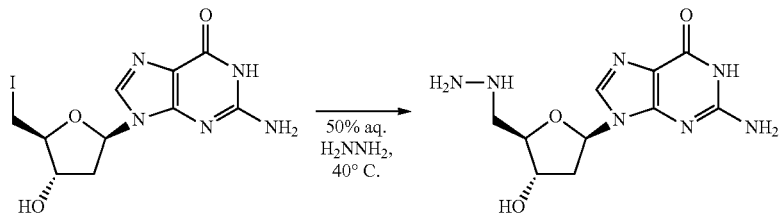 [SMILES: Nc1nc2c(ncn2[C@H]2C[C@H](O)[C@@H](CI)O2)c(=O)[nH]1 ; NNC[C@H]1O[C@@H](n2cnc3c(=O)[nH]c(N)nc32)C[C@@H]1O]

12  2-amino-9-((2R,4S,5R)-5-((aminooxy)methyl)-4-hydroxytetrahydrofuran-2-yl)-1H-purin-6(9H)-one

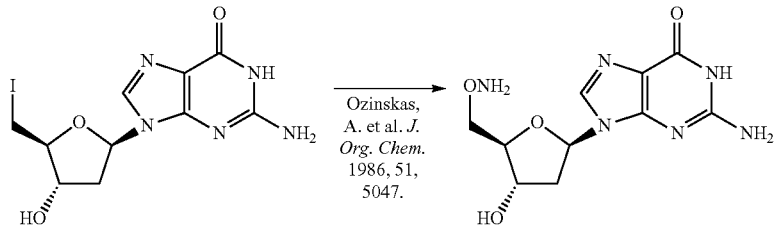

13  2-amino-9-((2R,4S,5R)-5-(azidomethyl)-4-hydroxytetrahydrofuran-2-yl)-1H-purin-6(9H)-one

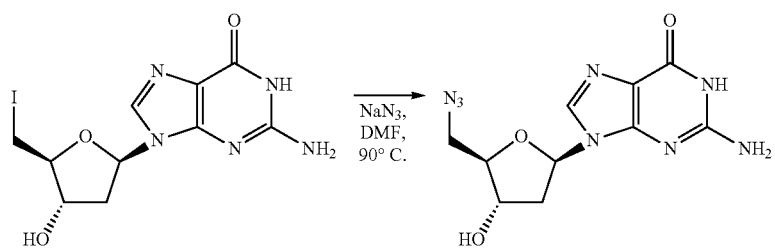 [SMILES: Nc1nc2c(ncn2[C@H]2C[C@H](O)[C@@H](CI)O2)c(=O)[nH]1 ; [N-]=[N+]=NC[C@H]1O[C@@H](n2cnc3c(=O)[nH]c(N)nc32)C[C@@H]1O]

TABLE 1-continued

Starting materials for preparation of compounds of Formula I.

Prep.
No.   Starting material compound name and synthetic method for producing same.

14   2-amino-9-((2R,4S,5R)-5-(aminomethyl)-4-hydroxytetrahydrofuran-2-yl)-1H-purin-6(9H)-one

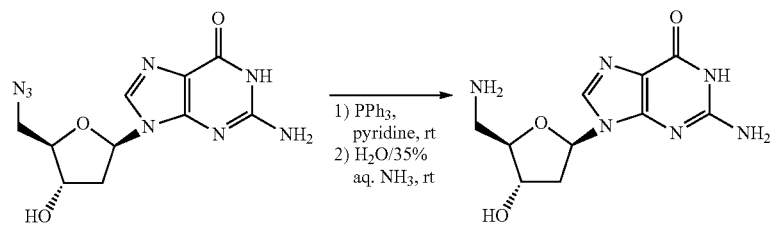 [SMILES: [N-]=[N+]=NC[C@H]1O[C@@H](n2cnc3c(=O)[nH]c(N)nc32)C[C@@H]1O ; NC[C@H]1O[C@@H](n2cnc3c(=O)[nH]c(N)nc32)C[C@@H]1O]

15   (2S,3S,5R)-5-(2-amino-6-oxo-1H-purin-9(6H)-yl)-3-hydroxytetrahydrofuran-2-carbaldehyde

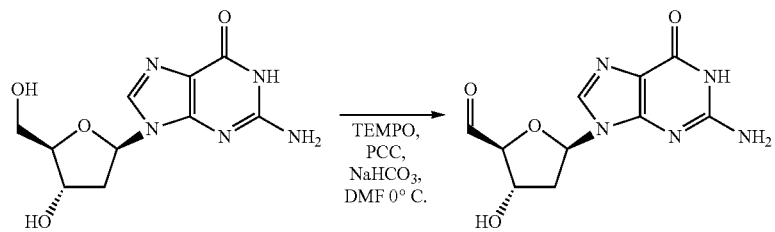 [SMILES: Nc1nc2c(ncn2[C@H]2C[C@H](O)[C@@H](CO)O2)c(=O)[nH]1 ; Nc1nc2c(ncn2[C@H]2C[C@H](O)[C@@H](C=O)O2)c(=O)[nH]1]

16   2-amino-9-((2R,4S,5R)-5-ethynyl-4-hydroxytetrahydrofuran-2-yl)-1H-purin-6(9H)-one

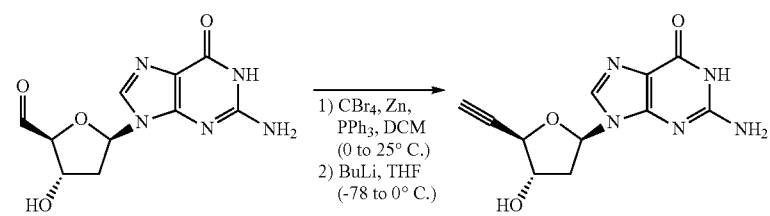 [SMILES: Nc1nc2c(ncn2[C@H]2C[C@H](O)[C@@H](C=O)O2)c(=O)[nH]1 ; C#C[C@H]1O[C@@H](n2cnc3c(=O)[nH]c(N)nc32)C[C@@H]1O]

17   2-((2R,3S,5R)-5-(2-amino-6-oxo-1H-purin-9(6H)-yl)-3-hydroxytetrahydrofuran-2-yl)acetaldehyde

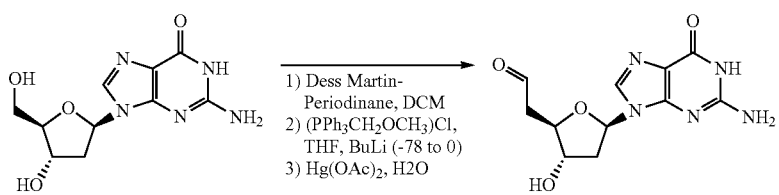 [SMILES: Nc1nc2c(ncn2[C@H]2C[C@H](O)[C@@H](CO)O2)c(=O)[nH]1 ; Nc1nc2c(ncn2[C@H]2C[C@H](O)[C@@H](CC=O)O2)c(=O)[nH]1]

18   2-amino-9-((2R,4S,5R)-4-hydroxy-5-(prop-2-yn-1-yl)tetrahydrofuran-2-yl)-1H-purin-6(9H)-one

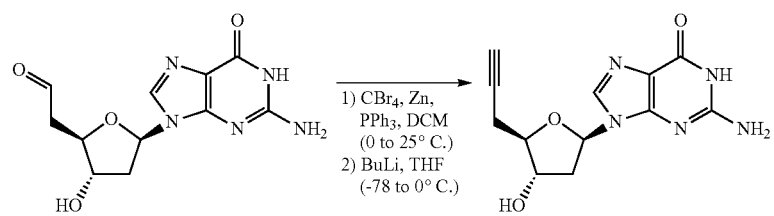 [SMILES: Nc1nc2c(ncn2[C@H]2C[C@H](O)[C@@H](CC=O)O2)c(=O)[nH]1 ; C#CC[C@H]1O[C@@H](n2cnc3c(=O)[nH]c(N)nc32)C[C@@H]1O]

General Procedures

General Procedure 1

Scheme 1 is utilized in preparing the following compounds.

Scheme 1

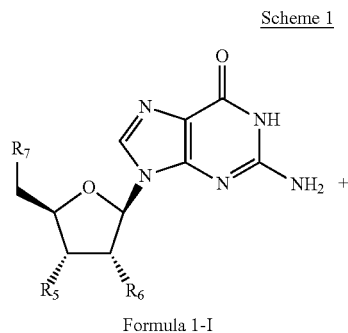

Formula 1-1

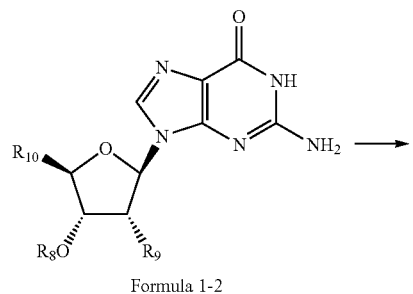

Formula 1-2

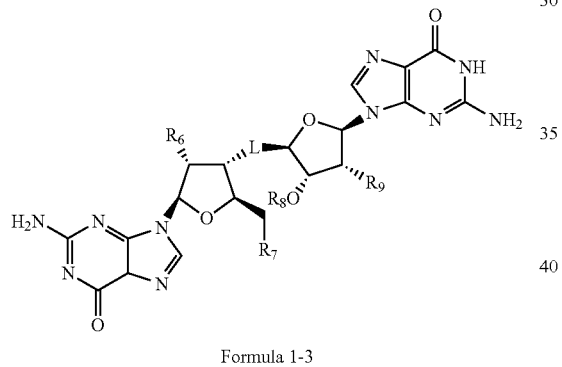

Formula 1-3

In Scheme 1, $R_7$ is selected from the group consisting of hydroxyl and —$OPO_3H_2$; $R_8$ is selected from the group consisting of hydrogen and —$PO_3H_2$; and $R_9$ is selected form the group consisting of hydrogen, hydroxyl and —$OPO_3H_2$. When $R_5$ is —$N_3^-$ and $R_{10}$ is —$CH_2$—$C\equiv CH$, L is:

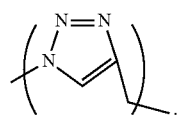

When $R_5$ is —$N_3^-$ and $R_{10}$ is —$C\equiv CH$, L is:

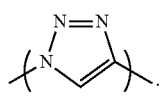

When $R_5$ is —O—$CH_2$-alkyne and $R_{10}$ is —$CH_2$—$N_3^-$, L is:

The reaction of Scheme 1 is performed as described in Paredes, E.; Das, S. *ChemBioChem,* 2011, 12, 125 in the presence of copper tris-(hydroxypropyltriazolylmethyl) amine ("CuPHPTA").

General Procedure 2

Scheme 2 is utilized in performing the following compounds.

Scheme 2

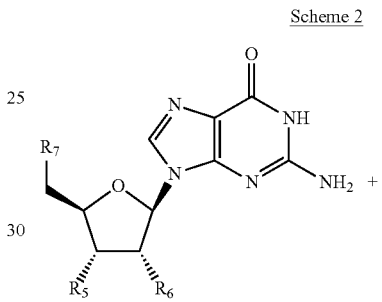

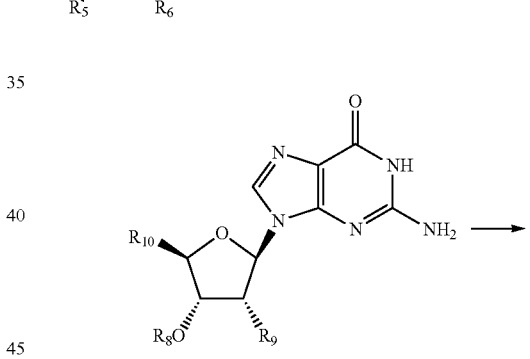

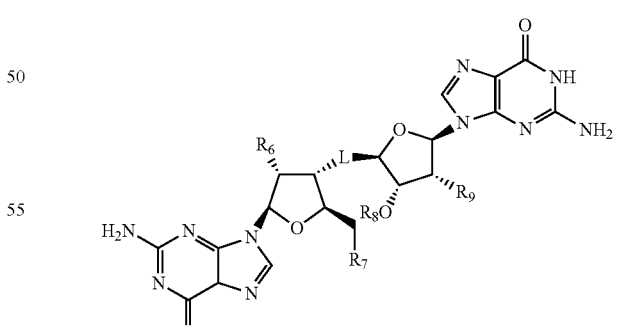

The reaction of Scheme 2 is performed as follows: 1) EtOH, Drierite; 2) $H_2$, Pd/C; 3) $Et_4NF$. See, Daher, R. et al., *J. Med. Chem.* 2010, 53, 7836.

$R_7$, $R_8$, and $R_9$ are as defined for Scheme 1. When $R_5$ is —NH—$NH_2$ and $R_{10}$ is —$CH_2$—C(=O)H, L is:

When $R_5$ is —NH—$NH_2$ and $R_{10}$ is —C(=O)H, L is:

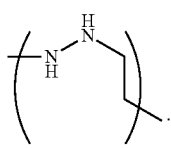

General Procedure 3

Scheme 3

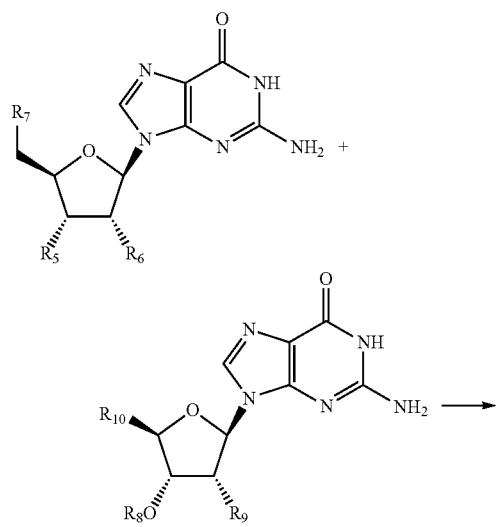

The reaction of Scheme 3 is performed as follows: 1) MeOH, pyridine; 2) $NaBH_3CN$, MeOH, AcOH; and 3) $Et_4NF$. See, Daher, R. et al., *J. Med. Chem.* 2010, 53, 7836.

$R_7$, $R_8$, and $R_9$ are as defined for Scheme 1. When $R_5$ is —$ONH_2$ and $R_{10}$ is —$CH_2$—C(=O)H, L is:

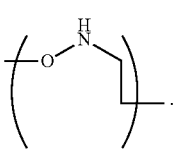

When $R_5$ is —$ONH_2$ and $R_{10}$ is —C(=O)H, L is:

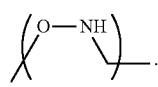

General Procedure 4

Scheme 4

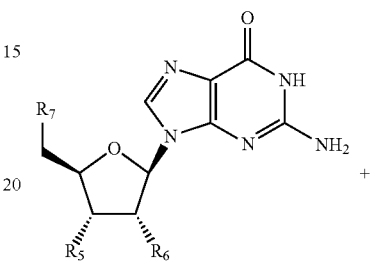

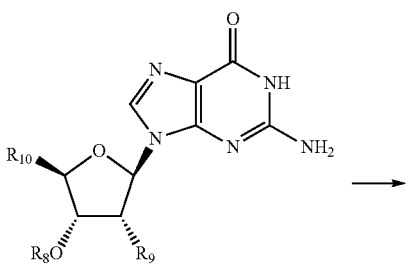

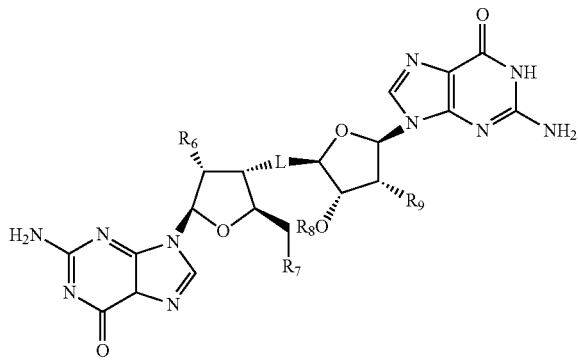

The reaction of Scheme 4 is reacted in the presence of NaH.

$R_7$, $R_8$, and $R_9$ are as defined for Scheme 1. When $R_5$ is —NH—S(=O)$_2$—$NH_2$ and $R_{10}$ is —($CH_2$)-halide, L is:

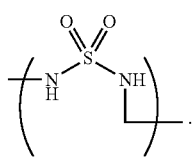

General Procedure 5

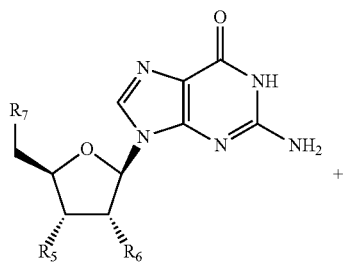

Scheme 5

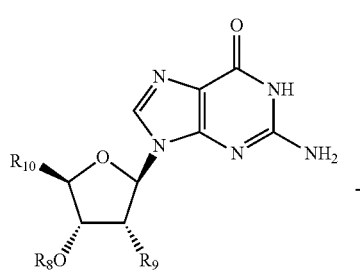

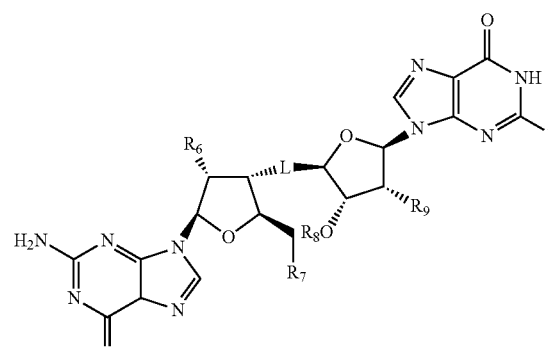

The reaction of Scheme 5 is performed in the presence of 3,4-dihydroxycyclobut-3-ene-1,2-dione, diethyl squarate, and N,N-disopropylethylamine (DIPEA) in DMF at room temperature (ambient conditions).

$R_7$, $R_8$, and $R_9$ are as defined for Scheme 1. When $R_5$ is —$NH_2$ and $R_{10}$ is —$CH_2$—$NH_2$, then L is:

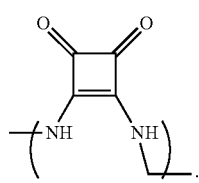

General Procedure 6

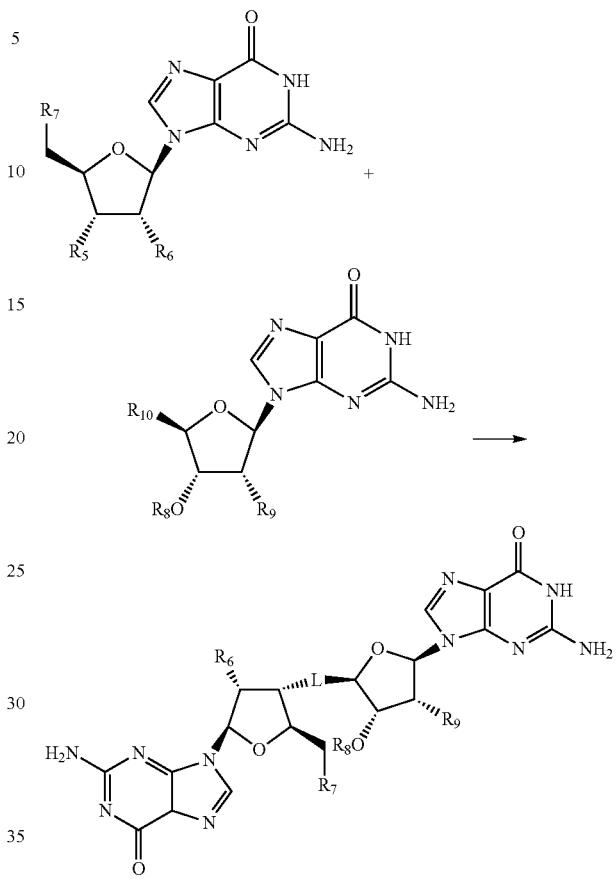

Scheme 6

The reaction of Scheme 6 is performed in the presence of 1) propan-2-one in toluene; 2) triphenylphosphine ($PPh_3$) and diethyl azodicarboxylate (DEAD) in toluene. See, Matteucci, M. et al., Tet. Lett. 1996, 37, 8667.

$R_7$, $R_8$, and $R_9$ are as defined for Scheme 1. When $R_5$ is —$NH_2$ and $R_{10}$ is —$CH_2$—$NH_2$, then L is:

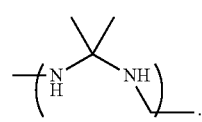

General Procedure 7

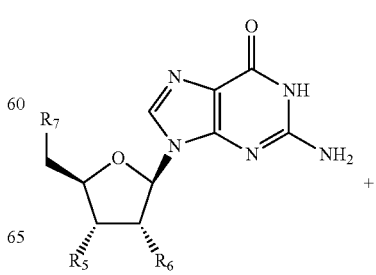

Scheme 7

37
-continued

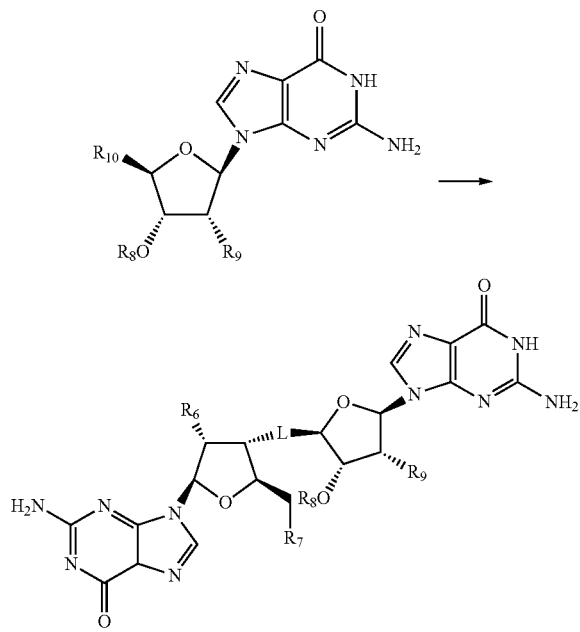

The reaction of Scheme 7 is performed in the presence of 1) 1,1,1,3,3,3-hexafluoropropan-2-one in toluene; 2) PPh₃ and DEAD in toluene. See, Matteucci, M. et al., *Tet. Lett.* 1996, 37, 8667.

R₇, R₈, and R₉ are as defined for Scheme 1. When R₅ is —NH₂, and R₁₀ is —CH₂—NH₂, then L is:

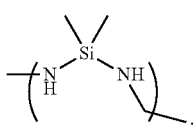

General Procedure 8

Scheme 8

38
-continued

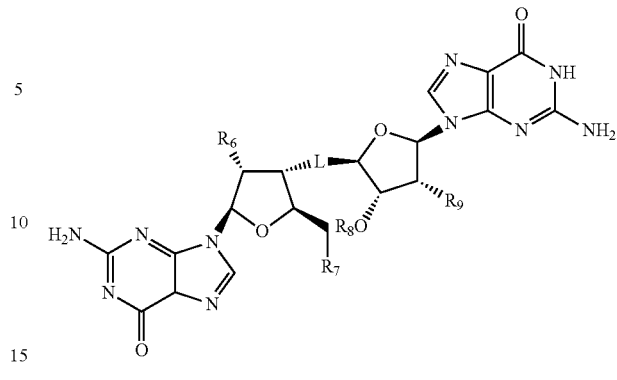

The reaction of Scheme 8 is performed in the presence of dichlorodimethylsilane. See, Wannagat, U.; Klemke, S. *Monatshefte fuer Cherie,* 1979, 110, 1077.

R₇, R₈, and R₉ are as defined for Scheme 1. When R₅ is —NH₂ and R₁₀ is —CH₂—NH₂, L is:

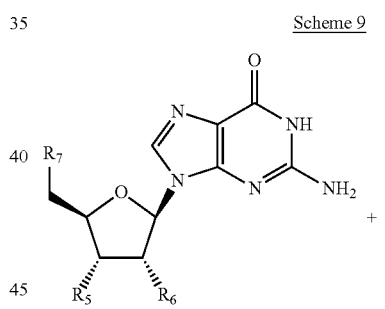

General Procedure 9

Scheme 9

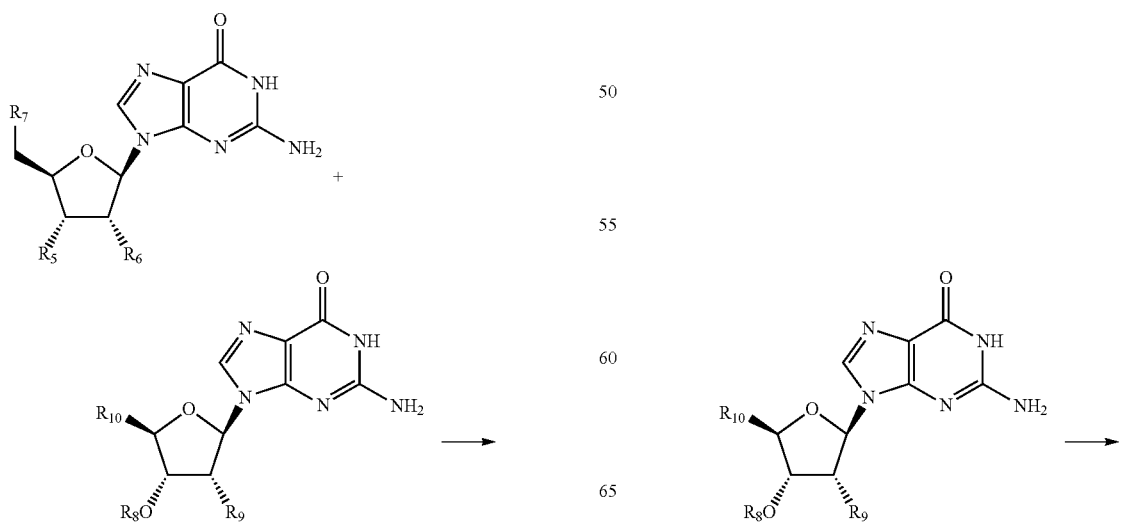

-continued

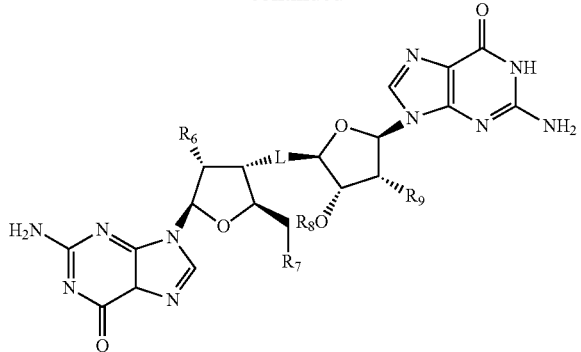

The reaction of Scheme 9 is performed in the presence of bis(4-nitrophenyl) carbonate in methylene chloride. See, Izdebski, J.; Pawlak, D. *Synthesis,* 1989, 6, 423.

$R_7$, $R_8$, and $R_9$ are as defined for Scheme 1. When $R_5$ is —$NH_2$ and $R_{10}$ is —$CH_2$—$NH_2$, L is:

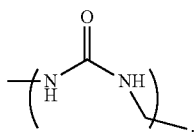

Example 1

3-((((2R,3S,4R,5R)-5-(2-amino-6-oxo-1H-purin-9 (6H)-yl)-3,4-dihydroxytetrahydrofuran-2-yl)methyl) amino)-4-(((2S,3S,4R,5R)-5-(2-amino-6-oxo-1H- purin-9(6H)-yl)-4-hydroxy-2-(hydroxymethyl) tetrahydrofuran-3-yl)amino)cyclobut-3-ene-1,2- dione

A. Preparation of 2-[(dimethylamino)methylidene]guanosine (1)

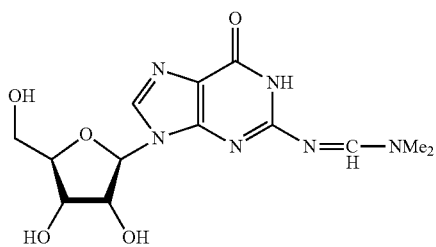

To a suspension of guanosine (6.16 g, 21.76 mmol) in 20 mL of abs. MeOH was added N,N-(dimethylamino)forma- mide dimethyl acetal (10.5 mL, 77.8 mmol). The mixture was stirred at r.t. for 5 days. The solid precipitate was filtered off and washed with cold MeOH and $Et_2O$, and dried to yield the product (1) (6.90 g, 93.7%).

White solid. $^1H$ NMR (400 MHz, DMSO-$d_6$) δ 11.36 (brs, 1H), 8.53 (s, 1H), 8.04 (s, 1H), 5.79 (d, J=6.4 Hz, 1H), 5.43 (s, 1H), 5.20 (s, 1H), 5.04 (dd, J=5.6, 5.2 Hz, 1H), 4.48 (dd, J=5.2, 5.2 Hz, 1H), 4.12 (dd, J=4.0, 3.6 Hz, 1H), 3.90 (ddd, J=4.4, 4.0, 3.2 Hz, 1H), 3.63 (ddd, J=11.6, 4.8, 4.4 Hz, 1H), 3.90 (ddd, J=12, 4.8, 4.4 Hz, 1H), 3.15 (s, 3H), 3.03 (s, 3H); $^{13}C$ NMR (100 MHz, DMSO-$d_6$) δ 158.0, 157.6, 157.3, 150.0, 137.0, 119.8, 86.7, 85.4, 73.8, 70.5, 61.5, 40.7, 34.7.

B. Preparation of 5'-O-[(tert-Butyl)diphenylsilyl]-2- [(dimethylamino)methlyledene]guanosine (2)

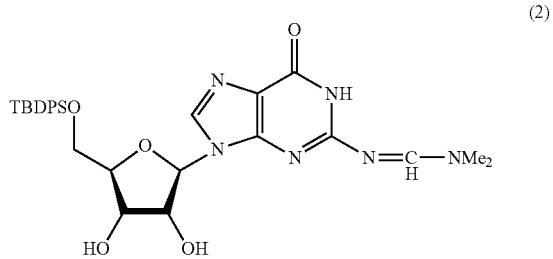

A suspension of 2-[(dimethylamino)methylidene]guanos- ine (1) (6.78 g, 20.0 mmol) in 200 mL of dry pyridine was stirred with (t-Bu)Ph$_2$Cl (5.86 mL, 79.1 mmol) and 4-dim- ethylaminopyridine (DMAP) (138.7 mg, 1.14 mmol) for 3 days to give a clear soln. MeOH (30 mL) was added, and the mixture was stirred for an additional 0.5 h and evaporated under reduced pressure. The residue was washed with cold $H_2O$ and dried under vacuum. The solid was stirred with $Et_2O$, filtered, and washed with $Et_2O$. The solid product was dried in vacuum to give (2) (10.48 g, 90.6%). "TBDPS" in the structure of (2) is the tert-butyl)diphenylsilyl radical:

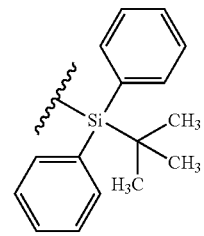 [SMILES: *[Si](c1ccccc1)(c1ccccc1)C(C)(C)C]

White solid. TLC (CHCl$_3$/MeOH 9:1): Rf 0.28; $^1H$ NMR (500 MHz, DMSO-d6) δ 11.4 (s, 1H), 8.51 (s, 1H), 7.97 (s, 1H), 7.63-7.60 (m, 4H), 7.45-7.36 (m, 6H), 5.86 (d, J=5.0 Hz, 1H), 4.49 (t, J=5.0 Hz, 1H), 4.27 (dd, J=5.5, 5.0 Hz, 1H), 4.01 (ddd, J=4.5, 4.5, 4.0 Hz, 1H), 3.88 (dd, J=11.5, 3.5 Hz, 1H), 3.78 (dd, J=11.5, 5.0 Hz, 1H), 3.10 (s, 3H), 3.02 (s, 3H), 0.98 (s, 9H); $^{13}C$ NMR (500 MHz, DMSO-d6) δ 157.8, 157.5, 157.2, 149.9, 147.0, 139.6, 136.4, 135.1, 135.0132.8, 132.6, 129.9, 127.9, 125.1, 119.5, 86.8, 84.2, 73.6, 69.9, 64.1, 40.7, 34.7, 26.6, 18.8.

C. Preparation of 2'-O-Acetyl-3'-bromo-5'-O-[(tert- butyl)diphenylsilyl]-3'-deoxy-2-[(dimethylamino) methylidene]guanosine (3)

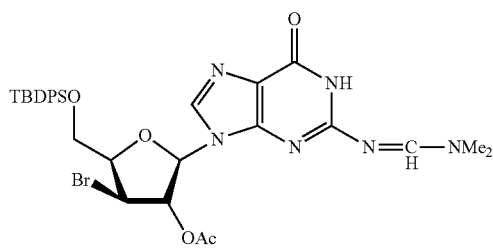

To a suspension of (2) (4.87 g, 8.45 mmol) in 163.9 mL of MeCN was added 140 μL of H$_2$O. The mixture was cooled to 0° C. in an ice-H$_2$O bath, and 1-(bromocarbonyl)-1-methyl acetate (4.9 mL, 32.1 mmol) was added dropwise under Ar. The mixture was stirred at 0° C. for 2 h to give a clear soln. After stirring for an additional 4 h at r.t., the mixture was evaporated to dryness. The residue was dissolved in CHCl$_3$ (300 mL) and washed carefully with cold H$_2$O (40 mL) NaHCO$_3$ soln (3×60 mL), and brine (100 mL). The aq. Layer were re-extracted with CHCl$_3$ (3×60 mL), and the combined org. layers were dried (Na$_2$SO$_4$) and evaporated under reduced pressure. The residue was submitted to FC (silica gel; MeOH/CHCl$_3$ (0-5%)) to afford (3) (5.0 g, 87.7%). White foam.

TLC (CHCl$_3$/MeOH 9:1): Rf 0.52. $^1$H NMR (500 MHz, CDCl$_3$) δ 9.22 (s, 1H), 8.61 (s, 1H), 7.82 (s, 1H), 7.70-7.66 (m, 4H), 7.47-7.37 (m, 6H), 6.08 (s, 1H), 5.93 (d, J=2.0 Hz, 1H), 4.42 (ddd, J=6.5, 6.5, 4.0 Hz, 1H), 4.36 (dd, J=5.0, 1.0 Hz, 1H), 4.05 (dd, J=13.0, 7.0 Hz, 1H), 3.97 (dd, J=13.5, 8.0 Hz, 1H), 3.18 (s, 3H), 3.07 (s, 3H), 2.2 (s, 3H), 1.07 (s, 9H); $^{13}$C NMR (125 MHz, CDCl$_3$) δ 168.8, 158.7, 157.71, 156.99, 149.6, 136.1, 135.54, 135.50, 132.8, 132.7, 130.0, 127.84, 127.82, 120.6, 88.6, 81.9, 81.7, 64.6, 49.9, 41.3, 35.1, 26.8, 20.9, 19.2.

D. Preparation of 3'-Bromo-5'-O-[(tert-butyl)diphenylsilyl]-3'-deoxy-2-[(dimethylamino)methylidene]guanosine (4)

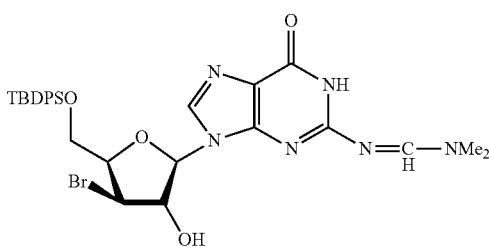

(4)

To a soln of (3) (0.84 g, 1.24 mmol) in 3.0 mL of MeOH was added dropwise a 7.0N soln. of NH3 in MeOH (0.88 mL, 6.2 mmol). The mixture was stirred at r.t. for 1.5 h. AcOH (1 mL) was added, and the solvent was evaporated under reduced pressure. The residue was dissolved in CHCl$_3$ (100 mL) and washed with H$_2$O (20 mL), NaHCO$_3$ soln. (2×20 mL), and brine (2×20 mL). The aq. Layer was extracted with CHCl$_3$ (2×20 mL), and the combined org. layer were dried (Na$_2$SO$_4$). After evaporation, the residue was submitted to FC to yield (4) (0.41 g, 51%).

White solid. TLC (CHCl$_3$/MeOH 9:1): Rf 0.42. $^1$H NMR (500 MHz, CDCl$_3$) δ 9.88 (brs, 1H), 8.49 (s, 1H), 7.79 (s, 1H), 7.69-7.65 (m, 4H), 7.42-7.37 (m, 6H), 6.54 (brs, 1H), 5.91 (d, J=3.0 Hz, 1H), 5.25 (brs, 1H), 4.54 (dd, J=4.5, 2.0 Hz, 1H), 4.46 (ddd, J=5.5, 5.5, 4.5 Hz, 1H), 3.98 (dd, J=11.0, 5.0 Hz, 1H), 3.94 (dd, J=10.5, 6.0 Hz, 1H), 3.04 (s, 3H), 2.96 (s, 3H), 1.04 (s, 9H); $^{13}$C NMR (125 MHz, CDCl$_3$) δ 157.4, 157.2, 155.7, 149.2, 136.3, 134.6, 132.0, 128.83, 128.80, 126.8, 126.7, 118.0, 89.4, 81.5, 79.7, 63.7, 53.0, 40.5, 34.1, 25.8, 18.2.

E. Preparation of 2'-O-[(Benzylamino)carbonyl]-3'-bromo-5'-O-[(tert-butyl)diphenylsilyl]-3'-deoxy-2-[(dimethylamino)methylidene]guanosine (5)

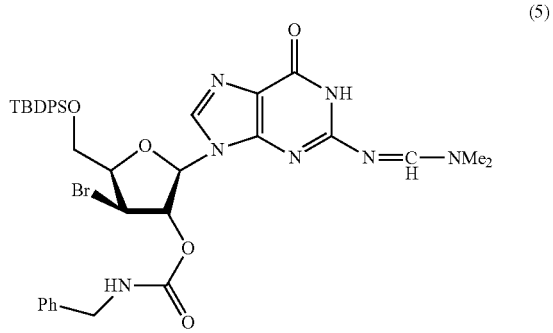

(5)

A soln of (4) (178.9 mg, 0.279 mmol), Et$_3$N (0.12 mL, 0.73 mmol), and PhCH$_2$NCO (0.1 mL, 1.07 mmol) in 2.8 mL of anh. THF was stirred at r.t. for 2.5 d. MeOH (1.8 mL) was added and the mixture was stirred for 2 h. After removal of solvent, the residue was submitted to FC (silica gel; MeOH/CHCl3) (0-5%)) to give (5) (105 mg, 49%).

White solid. TLC (AcOEt/MeOH 9:1) Rf 0.30. $^1$H NMR (500 MHz, CDCl$_3$) δ 9.70 (s, 1H), 8.57 (s, 1H), 7.80 (s, 1H), 7.70-7.65 (m, 4H), 7.44-7.38 (m, 6H), 7.31-7.26 (m, 5H), 6.01 (s, 1H), 5.98 (d, J=1.5 Hz, 1H), 5.94 (t, J=6.0 Hz, 1H), 4.46 (d, J=4.0 Hz, 1H), 4.42-4.39 (m, 3H), 4.03 (dd, J=10.5, 6.0 Hz, 1H), 3.95 (dd, J=10.5, 6.5 Hz, 1H), 2.99 (s, 3H), 2.93 (s, 3H), 1.06 (s, 9H); $^{13}$C NMR (125 MHz, CDCl$_3$) δ 158.7, 158.2, 157.1, 154.4, 149.9, 137.8, 136.1, 135.51, 135.46, 132.8, 132.7, 129.9, 128.7, 127.79, 127.77, 127.66, 127.5, 120.2, 88.5, 83.0, 81.5, 64.6, 50.6, 45.2, 41.1, 34.9, 26.7, 19.2.

F. Preparation of N'-(9-((2R,5S)-4-(benzylamino)-3-hydroxy-5-(hydroxymethyl)tetrahydrofuran-2-yl)-6-oxo-6,9-dihydro-1H-purin-2-yl)-N,N-dimethylformimidamide (6)

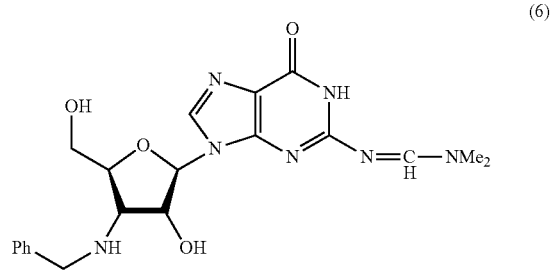

(6)

A solution of (5) (1.51 g, 1.96 mmol) in 65 mL of anh. DMF was cooled to −15° C. in an ice-EtOH bath. NaH (0.25 g, 6.28 mmol) was added under Ar. The suspension was stirred at −15 to 0° C. for 4 h, and then at r.t. for 24 h until disappearance of starting material. The solution was filtered and evaporated to dryness. The residue was dissolved in AcOEt (100 mL) and washed with H$_2$O (20 mL), NaHCO$_3$ solution (2×25 mL), and brine (20 mL). The aqueous layers were extracted with CHCl$_3$ (3×30 mL), and the combined organic layers were dried (Na$_2$SO$_4$). After removal of the solvent, the crude product without further purification was dissolved in 85 mL of MeOH and 85 mL of 3.0 N NaOH solution was added. Then the mixture was stirred at r.t. for 3 days. The mixture was neutralized with AcOH to PH 5. The aqueous solution was concentrated and loaded on a C18 reverse-phase column and eluted with 25% H₂O/MeOH to give the desired product (6) as a white solid (0.618 g, 85% yield).

TLC (i-PrOH/NH₃/H₂O 8:1:1) Rf 0.50. ¹H NMR (500 MHz, CD3OD) δ 7.98 (s, 1H), 7.38-7.23 (m, 5H), 5.89 (d, J=3.0 Hz, 1H), 4.50 (dd, J=5.5, 3.0 Hz, 1H), 4.01 (ddd, J=5.5, 3.0, 2.5 Hz, 1H), 3.89 (dd, J=12.5, 3.0 Hz, 1H), 3.84 (d, J=13.0 Hz, 1H), 3.82 (d, J=13.0 Hz, 1H), 3.72 (dd, J=12.0, 3.5 Hz, 1H), 3.50 (dd, J=6.0, 5.5 Hz, 1H); 13C NMR (125 MHz, CD3OD) 159.4, 155.3, 152.4, 141.2, 138.3, 129.60, 129.55, 128.3, 118.4, 91.9, 85.7, 74.4, 63.2, 60.1, 53.1.

G. Preparation of N'-(9-((2R,5S)-4-amino-3-hydroxy-5-(hydroxymethyl)tetrahydrofuran-2-yl)-6-oxo-6,9-dihydro-1H-purin-2-yl)-N,N-dimethylformimidamide (7)

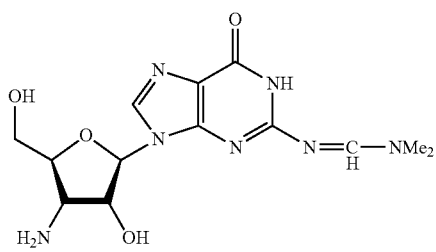

(7)

To a solution of (6) (0.188 mg, 0.50 mmol) in 31.6 mL of EtOH and 6.3 mL of AcOH were added 10% Pd/C (441 mg, 50% wet) and ammonium formate (2.38 g). The suspension was stirred overnight at r.t. The reaction was monitored by TLC. After filtration and removal of solvents by evaporation under reduced pressure, the residue was loaded on a C18 reversed-phase column eluting with H₂O/MeOH to give the desired product (7) as a white solid (0.121 g, 85%).

TLC (i-PrOH/NH₃/H₂O 8:1:1) Rf 0.25. 1H NMR (500 MHz, D₂O) δ 8.36 (s, 2H), 7.82 (s, 1H), 5.84 (d, J=4.0 Hz, 1H), 4.91 (dd, J=6.5, 4.5 Hz, 1H), 4.37 (ddd, J=6.0, 3.0, 2.5 Hz, 1H), 4.12 (dd, J=6.5, 6.0 Hz, 1H), 3.87 (dd, J=13.0, 3.0 Hz, 1H), 3.77 (dd, J=12.5, 3.5 Hz, 1H); 13C NMR (125 MHz, D2O) 160.8, 155.9, 153.2, 139.9, 118.7, 91.4, 83.7, 74.2, 63.0, 53.5.

H. Preparation of 3-(((2S,5R)-5-(2-amino-6-oxo-1H-purin-9(6H)-yl)-4-hydroxy-2-(hydroxymethyl)tetrahydrofuran-3-yl)amino)-4-ethoxycyclobut-3-ene-1,2-dione (8)

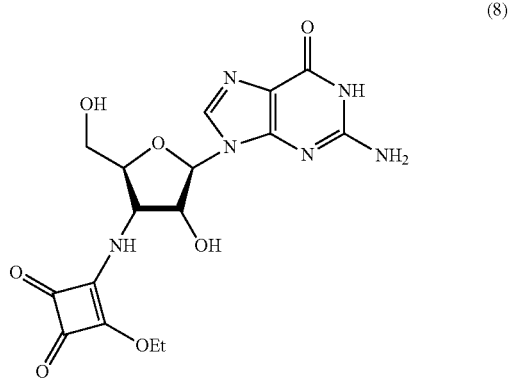

(8)

To a solution of secondary amine 7 (22.3 mg, 0.079 mmol) in anhydrous DMF (1.0 mL), Et₃N (7.0 µL, 0.040 mmol) and 3,4-diethoxycyclobut-3-ene-1,2-dione (12.9 µL, 0.086 mmol) were added. The reaction was stirred for 4 days at room temperature. The solvent was removed in vacuo. The residue was sonicated with H₂O for five minutes, filtered off, washed with H₂O and then dried at 105° C. overnight to give 8 as a light yellow powder (19.8 mg, 62% yield).

¹H NMR (500 MHz, DMSO-d₆) δ 10.67 (s, 1H), 10.66 (s, 1H), 9.03 (d, J=8.0 Hz, 1H), 8.85 (d, J=8.0 Hz, 1H), 7.94 (s, 2H), 6.43 (s, 4H), 5.99 (s, 2H), 5.75 (s, 2H), 5.14 (br, 2H), 4.81 (ddd, J=7.5, 6.5, 6.5 Hz, 1H), 4.68 (q, J=7.0 Hz, 2H), 4.61 (q, J=7.0 Hz, 2H), 4.46 (m, 1H), 4.44 (m, 1H), 4.31 (ddd, J=7.5, 6.5, 6.5 Hz, 1H), 3.68 (m, 1H), 3.55 (m, 1H), 1.38 (t, J=7.0 Hz, 3H), 1.27 (t, J=7.0 Hz, 1H); 13C NMR (125 MHz, DMSO-d6) 189.3, 188.7, 182.9, 182.5, 177.4, 177.2, 173.4, 172.8, 156.6, 153.6, 150.9, 135.3, 135.1, 116.7, 87.3, 82.0, 81.6, 74.4, 74.0, 68.8, 60.8, 60.4, 55.5, 55.4, 15.5, 15.3; HRMS (ESI) calcd. for [C₁₆H₁₈N₆O₇+H]⁺: 407.1315. Found 407.1315.

I. Preparation of 3-((((2R,3S,4R,5R)-5-(2-amino-6-oxo-1H-purin-9(6H)-yl)-3,4-dihydroxytetrahydrofuran-2-yl)methyl)amino)-4-(((2S,3S,4R,5R)-5-(2-amino-6-oxo-1H-purin-9(6H)-yl)-4-hydroxy-2-(hydroxymethyl)tetrahydrofuran-3-yl)amino)cyclobut-3-ene-1,2-dione (9)

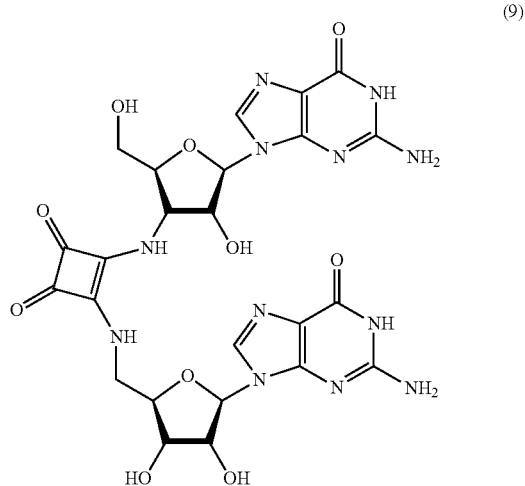

(9)

To a solution of 8 (19.0 mg, 0.047 mmol) in anhydrous DMF (1 mL), Et$_3$N (4.3 μL, 3.1 mg) and primary amine 6 (13.2 mg, 0.047 mmol) were added. The reaction was stirred for 5 days at room temperature. The solvent was removed in vacuo. The residue was sonicated with H$_2$O for five minutes, filtered off, washed with H$_2$O and then dried at 105° C. overnight to give 9 as a light yellow powder (18.6 mg, 62% yield).

$[\alpha]^{25}_D$=−0.025 (c=0.18, DMSO); $^1$H NMR (500 MHz, DMSO-d$_6$) δ 10.68 (brs, 2H), 8.33 (s, 1H), 7.91 (s, 1H), 7.87 (s, 1H), 7.80 (brs, 1H), 6.68 (brs, 2H), 6.54 (brs, 2H), 6.47 (brs, 2H), 6.36 (brs, 2H), 5.76 (m, 1H), 5.69 (m, 1H), 5.13 (m, 1H), 5.04 (m, 1H), 4.55 (m, 1H), 4.46 (m, 1H), 4.20-4.16 (m, 1H), 3.97-3.90 (m, 3H), 3.64-3.58 (m, 2H); 13C NMR (125 MHz, DMSO-d$_6$) 182.4, 168.4, 156.6, 153.59, 153.52, 150.5, 135.69, 135.63, 116.9, 116.7, 89.5, 83.4, 73.9, 61.1, 55.0; HRMS (ESI) calcd. for $[C_{24}H_{26}N_{12}O_{10}+H]^+$: 643.1973. Found 643.1968.

Example 2

2-Amino-9-((2R,3R,4S,5S)-4-(4-(((2R,3S,5R)-5-(2-amino-6-oxo-1H-purin-9(6H)-yl)-3-hydroxytetrahydrofuran-2-yl)methyl)-1H-1,2,3-triazol-1-yl)-3-hydroxy-5-(hydroxymethyl)tetrahydrofuran-2-yl)-1H-purin-6(9H)-one The title compound is prepared according to General Procedure 1 as follows:

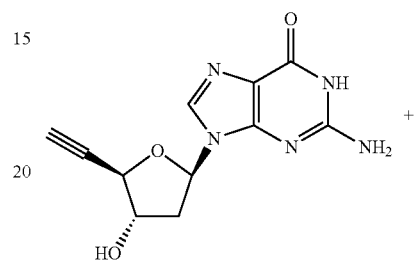

Example 3

2-Amino-9-((2R,3R,4S,5S)-4-(4-((2R,3S,5R)-5-(2-amino-6-oxo-1H-purin-9(6H)-yl)-3-hydroxytetrahydrofuran-2-yl)-1H-1,2,3-triazol-1-yl)-3-hydroxy-5-(hydroxymethyl)tetrahydrofuran-2-yl)-1H-purin-6(9H)-one The title compound is prepared according to General Procedure 1 as follows:

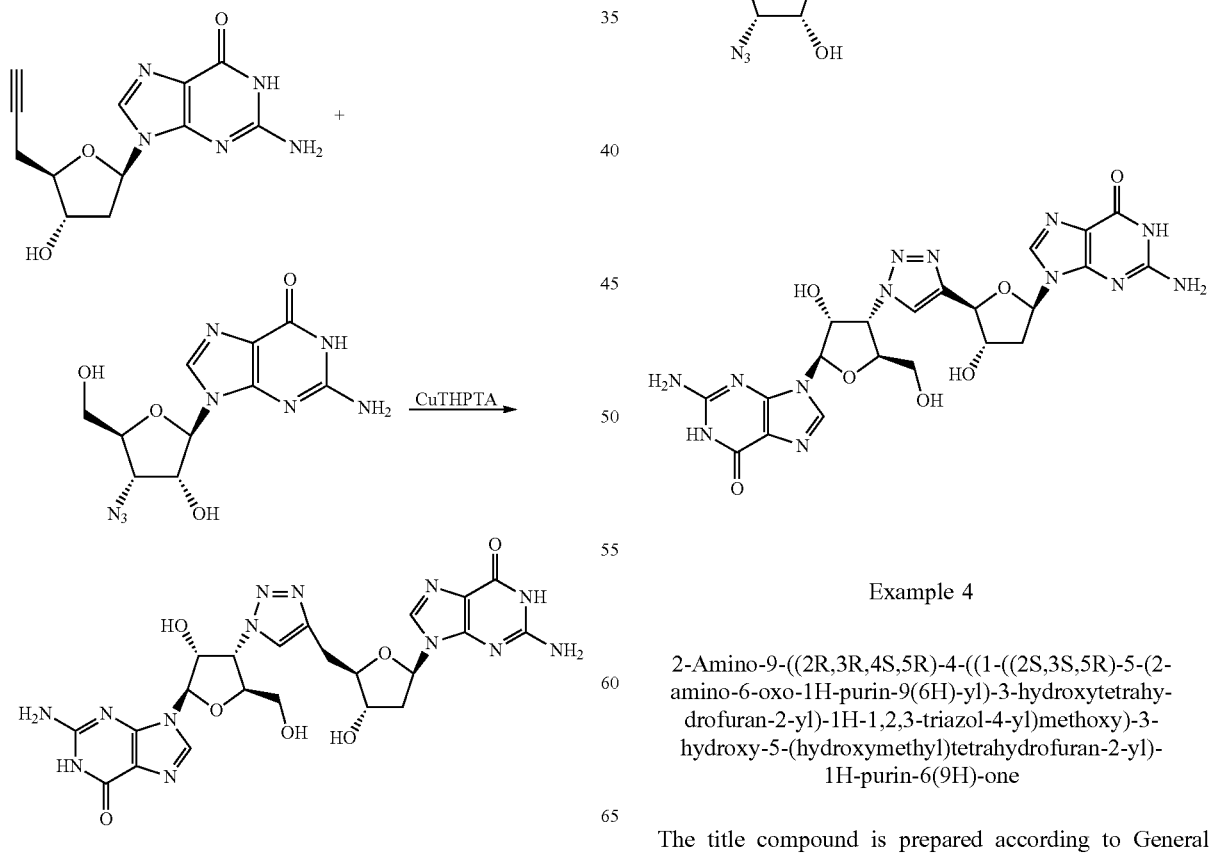

Example 4

2-Amino-9-((2R,3R,4S,5R)-4-((1-((2S,3S,5R)-5-(2-amino-6-oxo-1H-purin-9(6H)-yl)-3-hydroxytetrahydrofuran-2-yl)-1H-1,2,3-triazol-4-yl)methoxy)-3-hydroxy-5-(hydroxymethyl)tetrahydrofuran-2-yl)-1H-purin-6(9H)-one The title compound is prepared according to General Procedure 1 as follows:

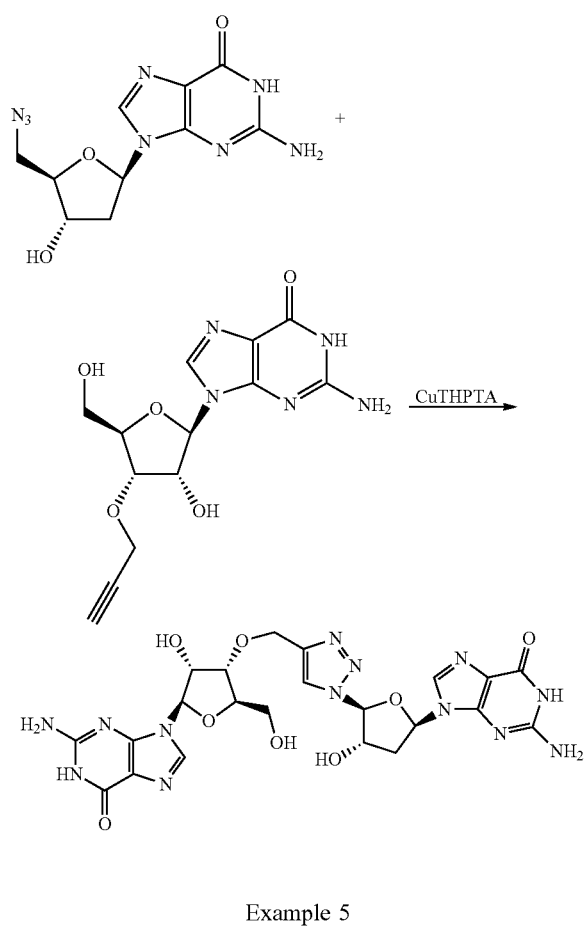

Example 5

2-Amino-9-((2R,3R,4S,5S)-4-(2-(2-((2R,3S,5R)-5-(2-amino-6-oxo-1H-purin-9(6H)-yl)-3-hydroxytetrahydrofuran-2-yl)ethyl)hydrazinyl)-3-hydroxy-5-(hydroxymethyl)tetrahydrofuran-2-yl)-1H-purin-6(9H)-one The title compound is prepared according to General Procedure 2 as follows:

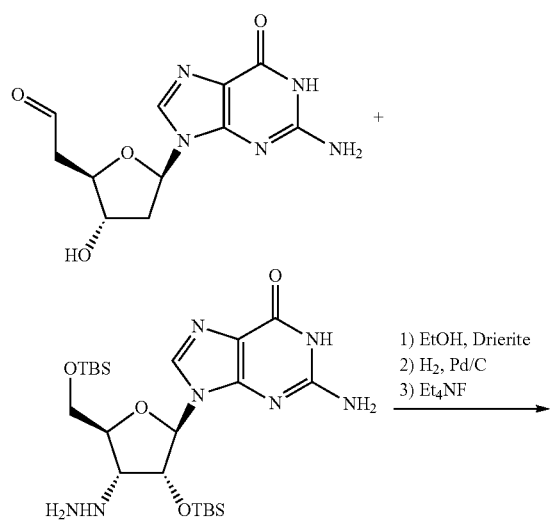

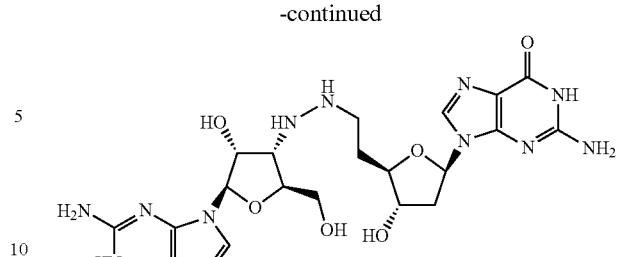

Example 6

2-Amino-9-((2R,3R,4S,5R)-4-(((2-((2R,3S,5R)-5-(2-amino-6-oxo-1H-purin-9(6H)-yl)-3-hydroxytetrahydrofuran-2-yl)ethyl)amino)oxy)-3-hydroxy-5-(hydroxymethyl)tetrahydrofuran-2-yl)-1H-purin-6(9H)-one The title compound is prepared according to General Procedure 3 as follows:

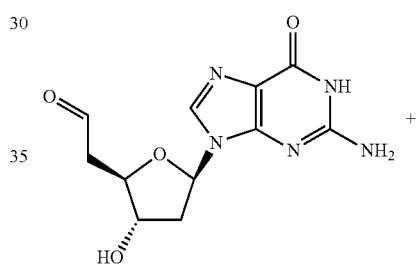

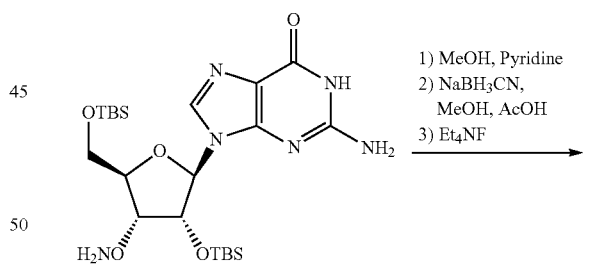

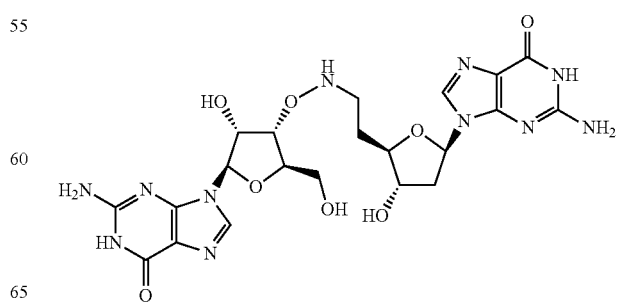

Example 7

2-Amino-9-((2R,3R,4S,5S)-4-(2-(((2R,3S,5R)-5-(2-amino-6-oxo-1H-purin-9(6H)-yl)-3-hydroxytetrahydrofuran-2-yl)methyl)hydrazinyl)-3-hydroxy-5-(hydroxymethyl)tetrahydrofuran-2-yl)-1H-purin-6(9H)-one The title compound is prepared according to General Procedure 2 as follows:

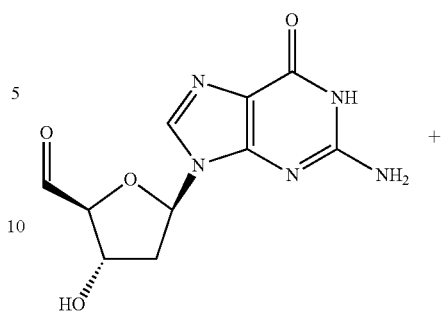

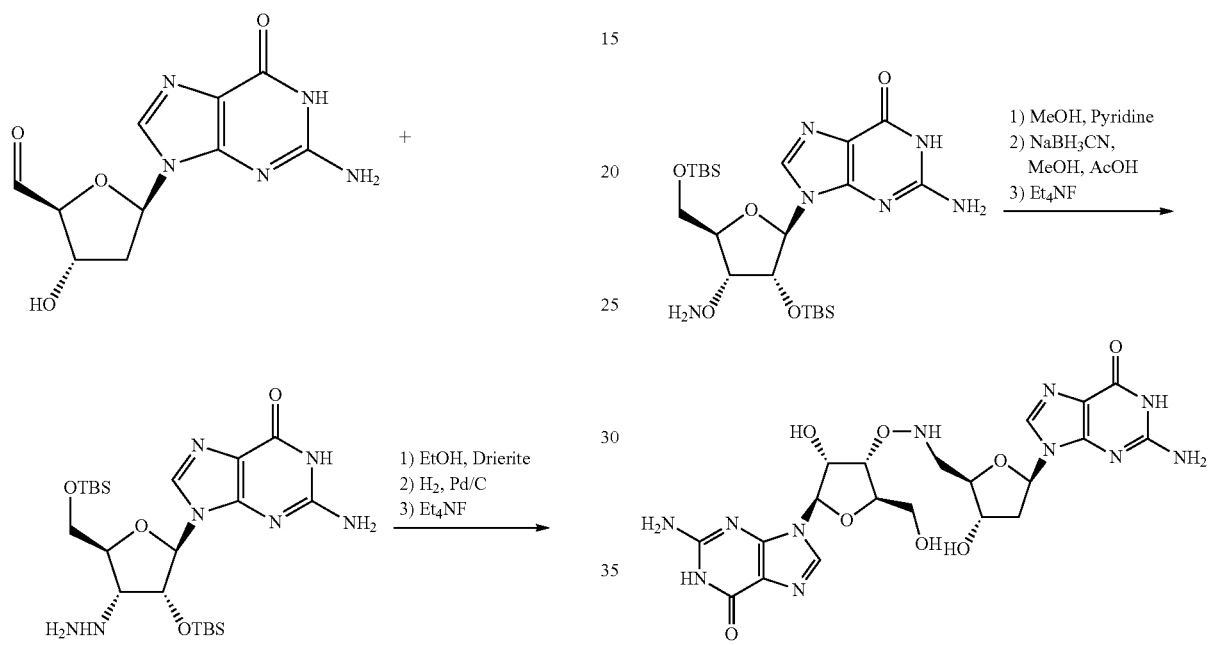

Example 8

2-Amino-9-((2R,3R,4S,5R)-4-(((((2R,3S,5R)-5-(2-amino-6-oxo-1H-purin-9(6H)-yl)-3-hydroxytetrahydrofuran-2-yl)methyl)amino)oxy)-3-hydroxy-5-(hydroxymethyl)tetrahydrofuran-2-yl)-1H-purin-6(9H)-one The title compound is prepared according to General Procedure 3 as follows:

Example 9

3-(((((2R,3S,5R)-5-(2-amino-6-oxo-1H-purin-9(6H)-yl)-3-hydroxytetrahydrofuran-2-yl)methyl)amino)-4-(((2S,3S,4R,5R)-5-(2-amino-6-oxo-1H-purin-9(6H)-yl)-4-hydroxy-2-(hydroxymethyl)tetrahydrofuran-3-yl)amino)cyclobut-3-ene-1,2-dione The title compound is prepared according to General Procedure 5 as follows:

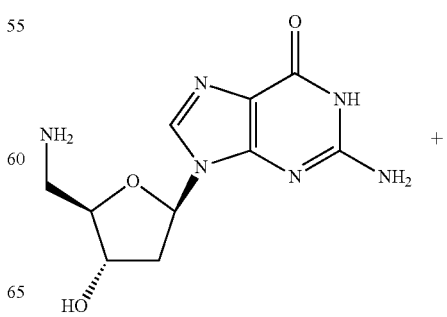

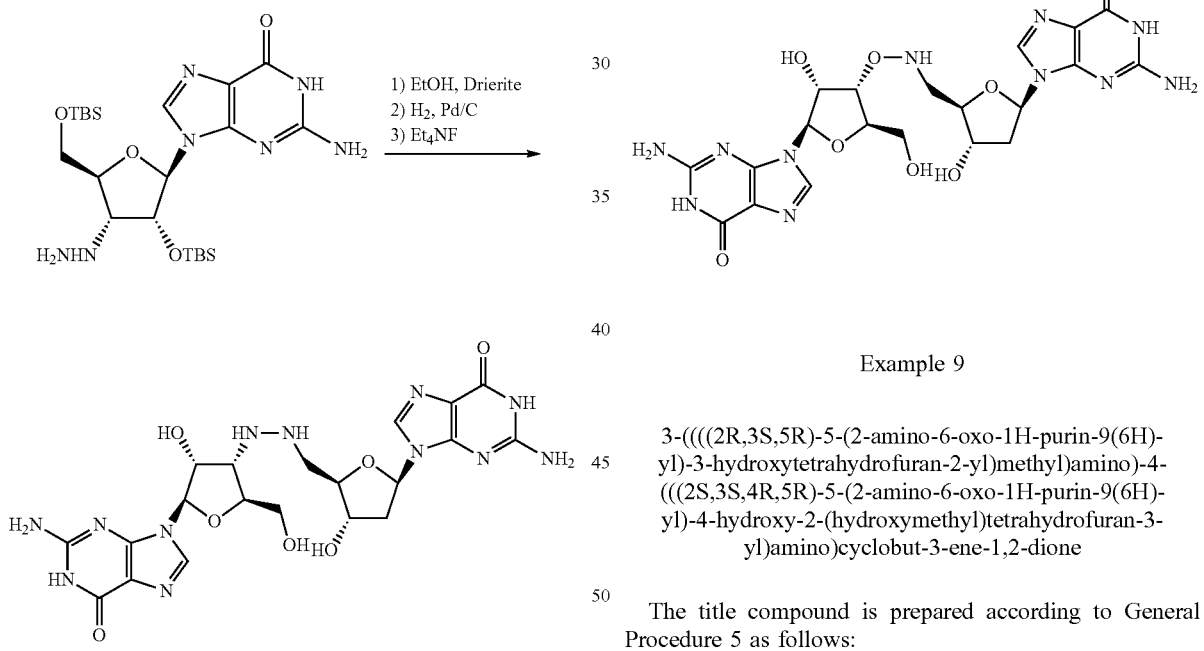

-continued

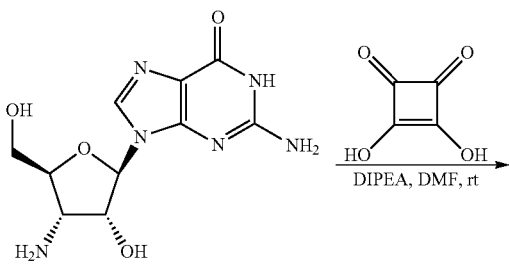

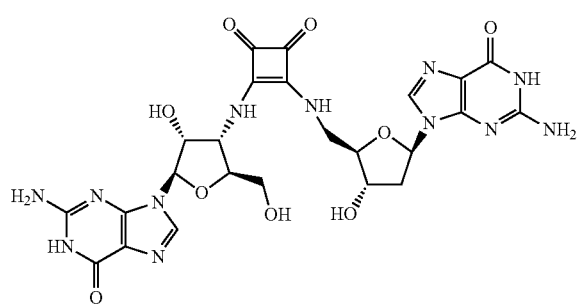

Example 10

2-Amino-9-((2R,3R,4S,5S)-4-((2-((((2R,3S,5R)-5-(2-amino-6-oxo-1H-purin-9(6H)-yl)-3-hydroxytetrahydrofuran-2-yl)methyl)amino)propan-2-yl)amino)-3-hydroxy-5-(hydroxymethyl)tetrahydrofuran-2-yl)-1H-purin-6(9H)-one The title compound is prepared according to General Procedure 6 as follows:

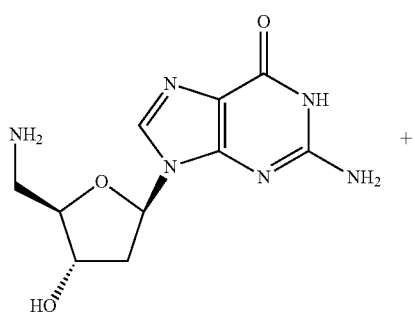

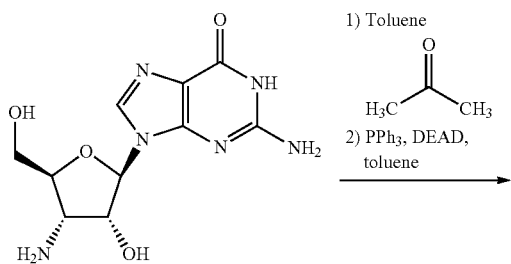

-continued

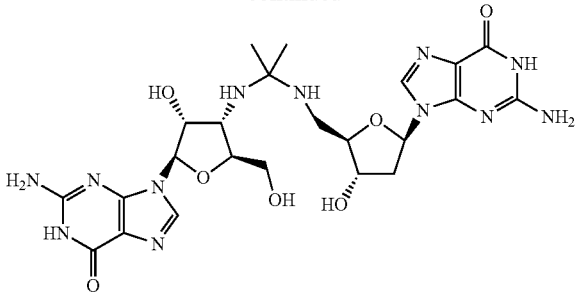

Example 11

2-Amino-9-((2R,3R,4S,5S)-4-((2-((((2R,3S,5R)-5-(2-amino-6-oxo-1H-purin-9(6H)-yl)-3-hydroxytetrahydrofuran-2-yl)methyl)amino)-1,1,1,3,3,3-hexafluoropropan-2-yl)amino)-3-hydroxy-5-(hydroxymethyl)tetrahydrofuran-2-yl)-1H-purin-6(9H)-one The title compound is prepared according to General Procedure 7 as follows:

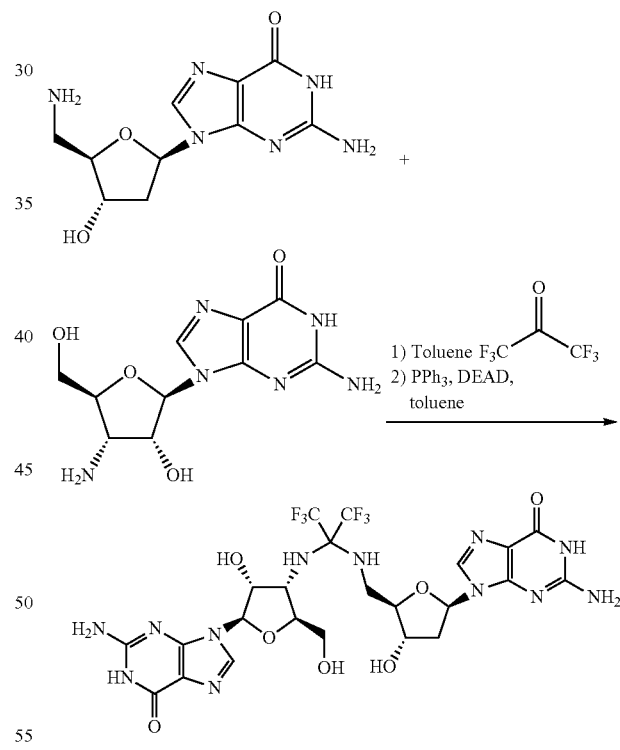

Example 12

2-Amino-9-((2R,3R,4S,5S)-4-(((((2R,3S,5R)-5-(2-amino-6-oxo-1H-purin-9(6H)-yl)-3-hydroxytetrahydrofuran-2-yl)methyl)amino)dimethylsilyl)amino)-3-hydroxy-5-(hydroxymethyl)tetrahydrofuran-2-yl)-1H-purin-6(9H)-one The title compound is prepared according to General Procedure 8 as follows:

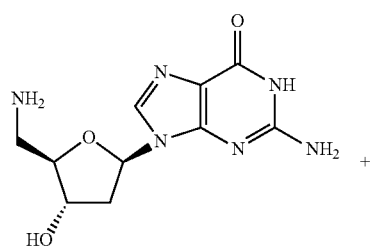
+
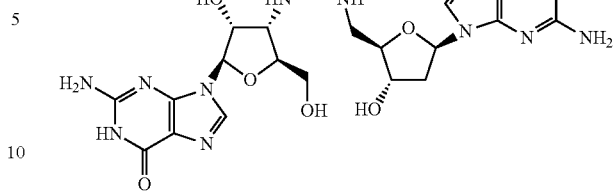
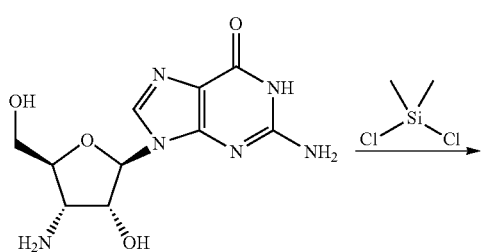
Example 13
1-(((2R,3S,5R)-5-(2-amino-6-oxo-1H-purin-9(6H)-yl)-3-hydroxytetrahydrofuran-2-yl)methyl)-3-((2S,3S,4R,5R)-5-(2-amino-6-oxo-1H-purin-9(6H)-yl)-4-hydroxy-2-(hydroxymethyl)tetrahydrofuran-3-yl) urea
The title compound is prepared according to General Procedure 9 as follows:
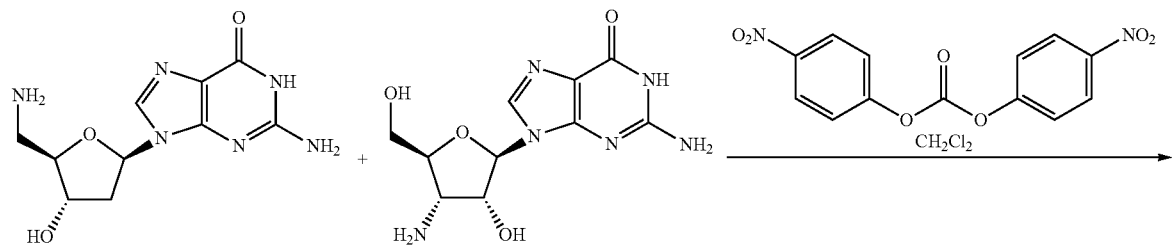
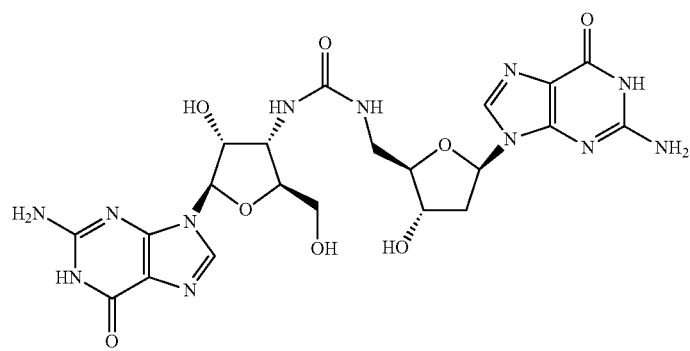

Example 14

2-Amino-9-((2R,3R,4S,5R)-5-((1-((2S,3S,5R)-5-(2-amino-6-oxo-1H-purin-9(6H)-yl)-2-(hydroxymethyl)tetrahydrofuran-3-yl)-1H-1,2,3-triazol-4-yl)methyl)-3,4-dihydroxytetrahydrofuran-2-yl)-1H-purin-6(9H)-one The title compound is prepared according to General Procedure 1 as follows:

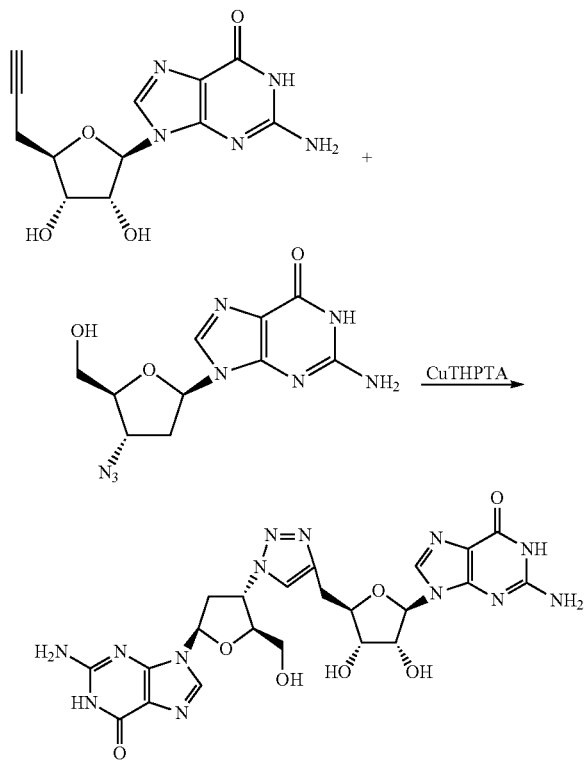

Example 15

2-Amino-9-((2R,3R,4S,5R)-5-(1-((2S,3S,5R)-5-(2-amino-6-oxo-1H-purin-9(6H)-yl)-2-(hydroxymethyl)tetrahydrofuran-3-yl)-1H-1,2,3-triazol-4-yl)-3,4-dihydroxytetrahydrofuran-2-yl)-1H-purin-6(9H)-one The title compound is prepared according to General Procedure 1 as follows:

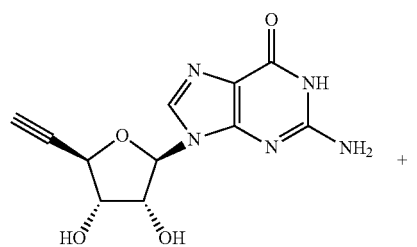

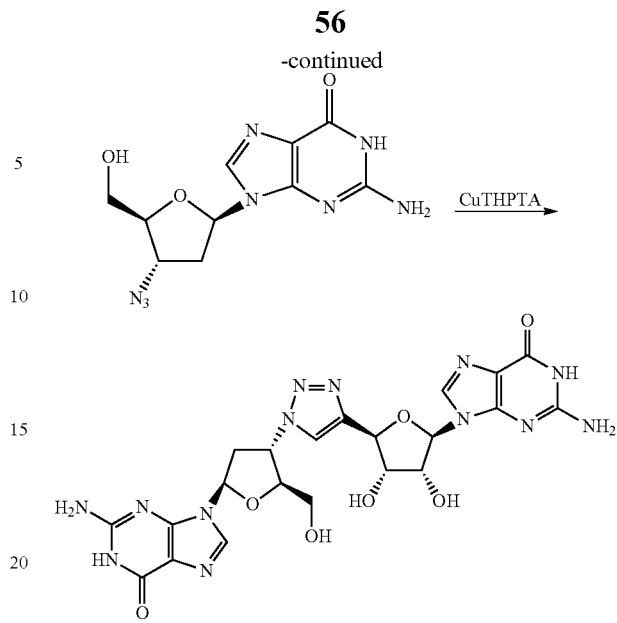

Example 16

2-Amino-9-((2R,3R,4S,5S)-5-(4-((((2R,3S,5R)-5-(2-amino-6-oxo-1H-purin-9(6H)-yl)-2-(hydroxymethyl)tetrahydrofuran-3-yl)oxy)methyl)-1H-1,2,3-triazol-1-yl)-3,4-dihydroxytetrahydrofuran-2-yl)-1H-purin-6(9H)-one The title compound is prepared according to General Procedure 1 as follows:

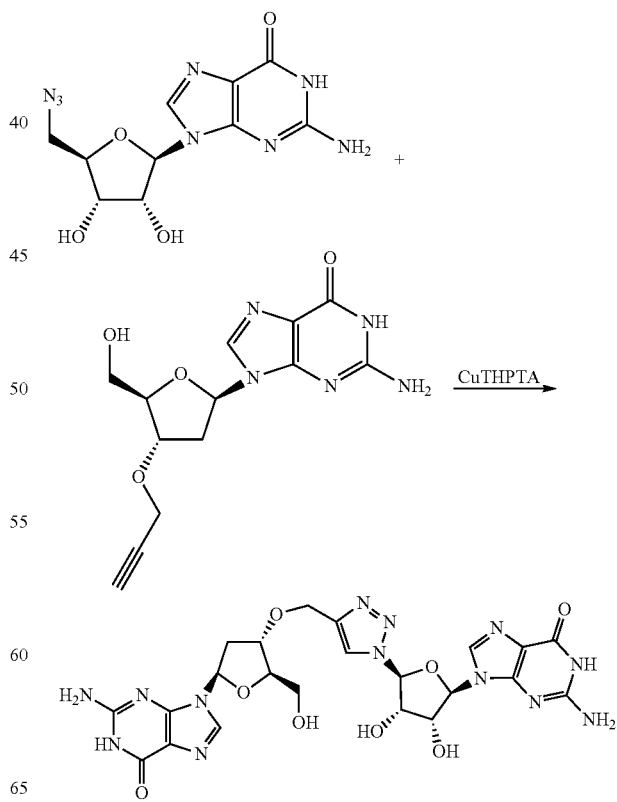

Example 17

2-Amino-9-((2R,3R,4S,5R)-5-(2-(2-((2S,3S,5R)-5-(2-amino-6-oxo-1H-purin-9(6H)-yl)-2-(hydroxymethyl)tetrahydrofuran-3-yl)hydrazinyl)ethyl)-3,4-dihydroxytetrahydrofuran-2-yl)-1H-purin-6(9H)-one The title compound is prepared according to General Procedure 2 as follows:

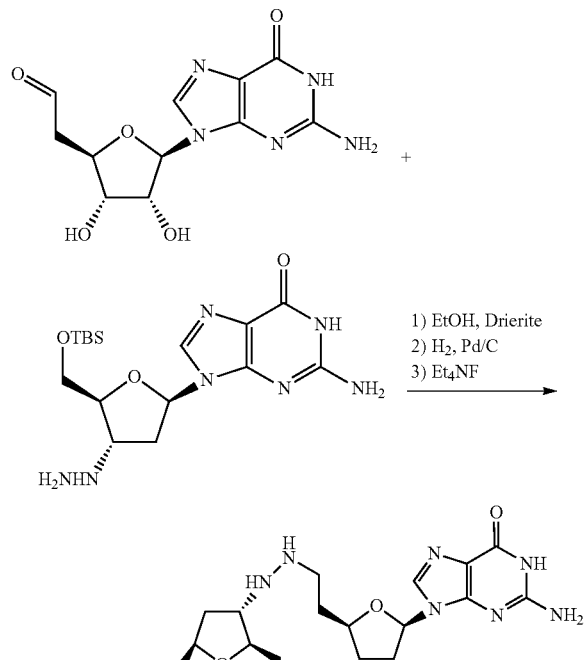

Example 18

2-Amino-9-((2R,3R,4S,5R)-5-(2-((((2R,3S,5R)-5-(2-amino-6-oxo-1H-purin-9(6H)-yl)-2-(hydroxymethyl)tetrahydrofuran-3-yl)oxy)amino)ethyl)-3,4-dihydroxytetrahydrofuran-2-yl)-1H-purin-6(9H)-one The title compound is prepared according to General Procedure 3 as follows:

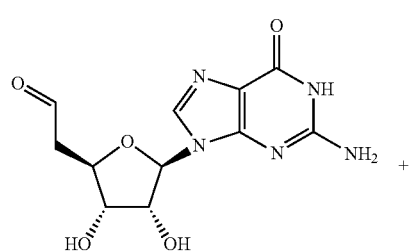

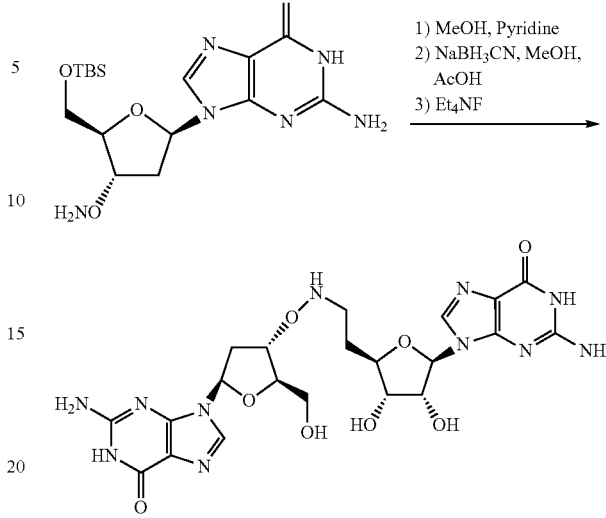

Example 19

2-Amino-9-((2R,3R,4S,5R)-5-((2-((2S,3S,5R)-5-(2-amino-6-oxo-1H-purin-9(6H)-yl)-2-(hydroxymethyl)tetrahydrofuran-3-yl)hydrazinyl)methyl)-3,4-dihydroxytetrahydrofuran-2-yl)-1H-purin-6(9H)-one The title compound is prepared according to General Procedure 2 as follows:

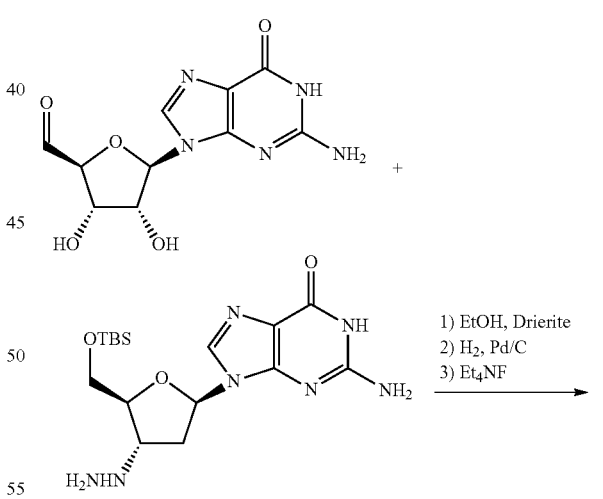

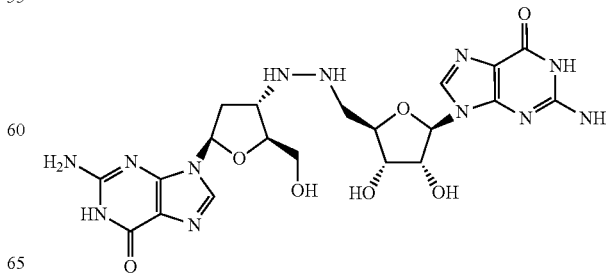

Example 20

2-Amino-9-((2R,3R,4S,5R)-5-(((((2R,3S,5R)-5-(2-amino-6-oxo-1H-purin-9(6H)-yl)-2-(hydroxymethyl)tetrahydrofuran-3-yl)oxy)amino)methyl)-3,4-dihydroxytetrahydrofuran-2-yl)-1H-purin-6(9H)-one The title compound is prepared according to General Procedure 3 as follows:

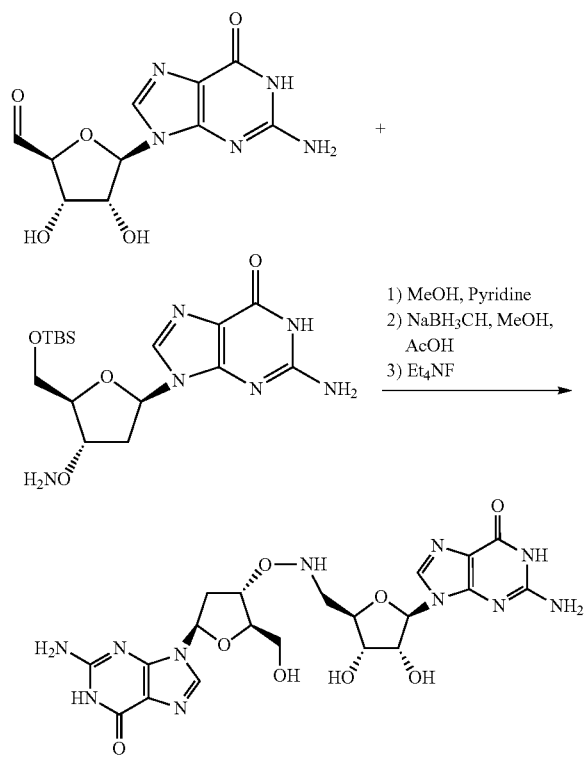

Example 21

3-(((2S,3S,5R)-5-(2-amino-6-oxo-1H-purin-9(6H)-yl)-2-(hydroxymethyl)tetrahydrofuran-3-yl)amino)-4-((((2R,3S,4R,5R)-5-(2-amino-6-oxo-1H-purin-9(6H)-yl)-3,4-dihydroxytetrahydrofuran-2-yl)methyl)amino)cyclobut-3-ene-1,2-dione The title compound is prepared according to General Procedure 5 as follows:

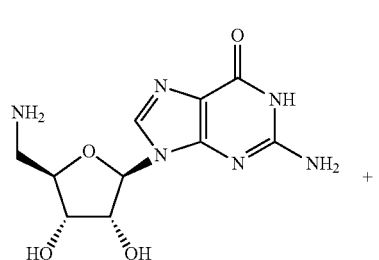

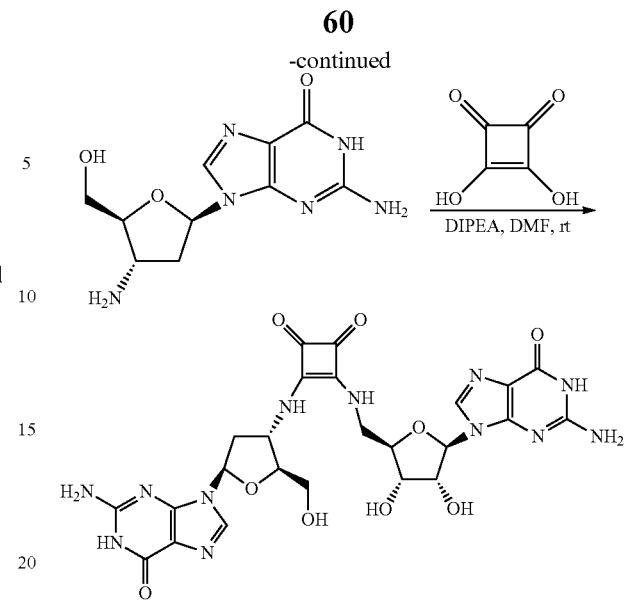

Example 22

2-Amino-9-((2R,3R,4S,5R)-5-(((2-(((2S,3S,5R)-5-(2-amino-6-oxo-1H-purin-9(6H)-yl)-2-(hydroxymethyl)tetrahydrofuran-3-yl)amino)propan-2-yl)amino)methyl)-3,4-dihydroxytetrahydrofuran-2-yl)-1H-purin-6(9H)-one The title compound is prepared according to General Procedure 6 as follows:

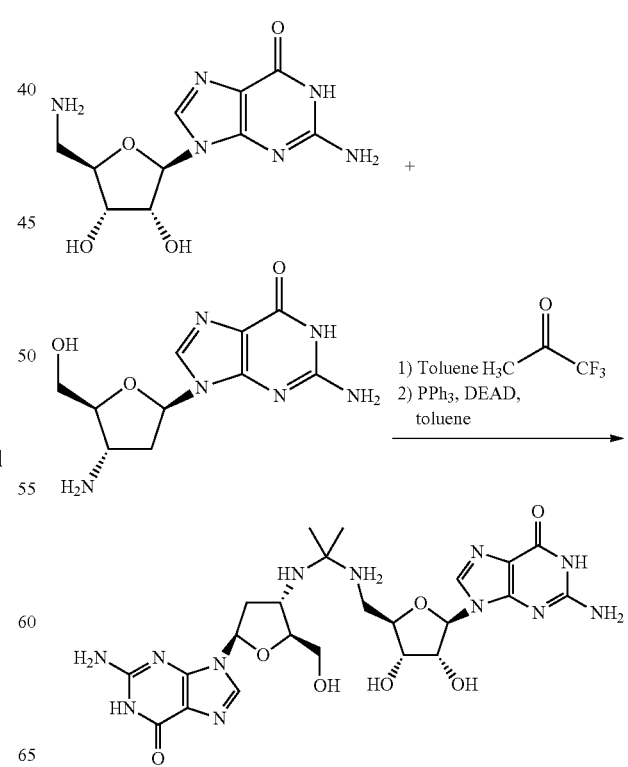

Example 23

2-Amino-9-((2R,3R,4S,5R)-5-(((2-(((2S,3S,5R)-5-(2-amino-6-oxo-1H-purin-9(6H)-yl)-2-(hydroxymethyl)tetrahydrofuran-3-yl)amino)-1,1,1,3,3,3-hexafluoropropan-2-yl)amino)methyl)-3,4-dihydroxytetrahydrofuran-2-yl)-1H-purin-6(9H)-one The title compound is prepared according to General Procedure 7 as follows:

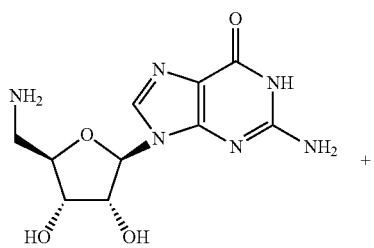

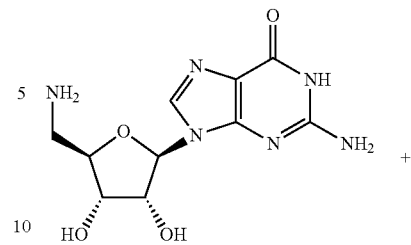

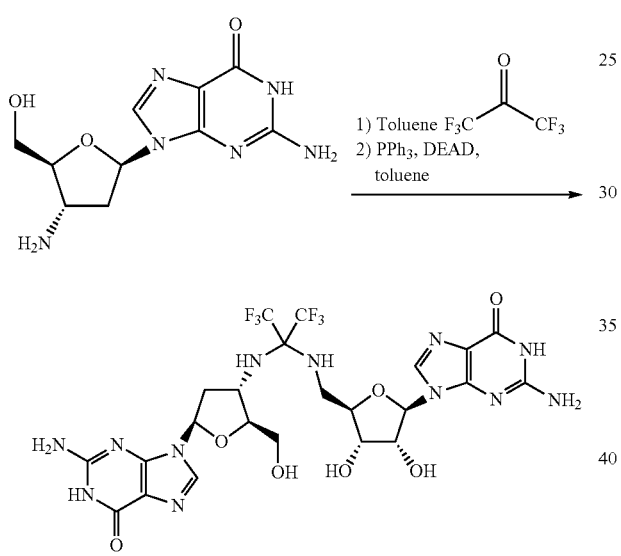

Example 24

2-Amino-9-((2R,3R,4S,5R)-5-((((((2S,3S,5R)-5-(2-amino-6-oxo-1H-purin-9(6H)-yl)-2-(hydroxymethyl)tetrahydrofuran-3-yl)amino)dimethylsilyl)amino)methyl)-3,4-dihydroxytetrahydrofuran-2-yl)-1H-purin-6(9H)-one The title compound is prepared according to General Procedure 8 as follows:

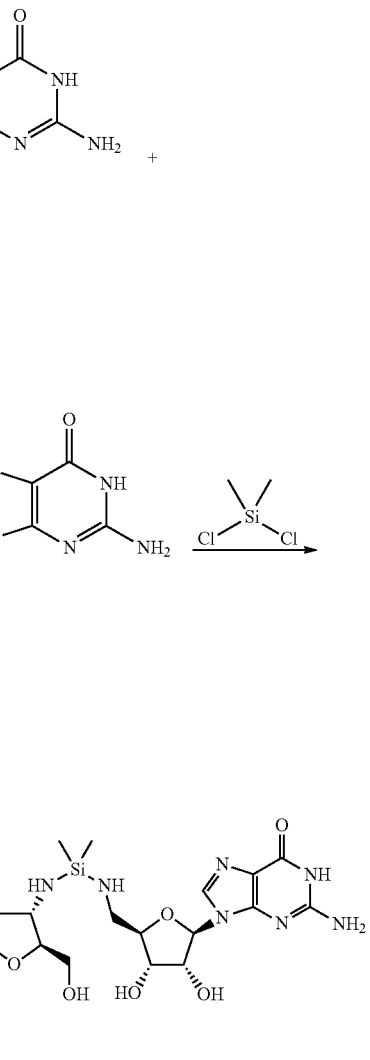

Example 25

1-((2S,3S,5R)-5-(2-amino-6-oxo-1H-purin-9(6H)-yl)-2-(hydroxymethyl)tetrahydrofuran-3-yl)-3-(((2R,3S,4R,5R)-5-(2-amino-6-oxo-1H-purin-9(6H)-yl)-3,4-dihydroxytetrahydrofuran-2-yl)methyl)urea The title compound is prepared according to General Procedure 9 as follows:

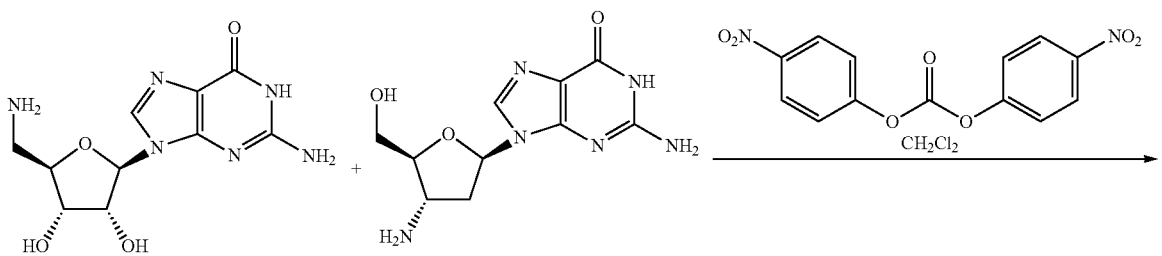

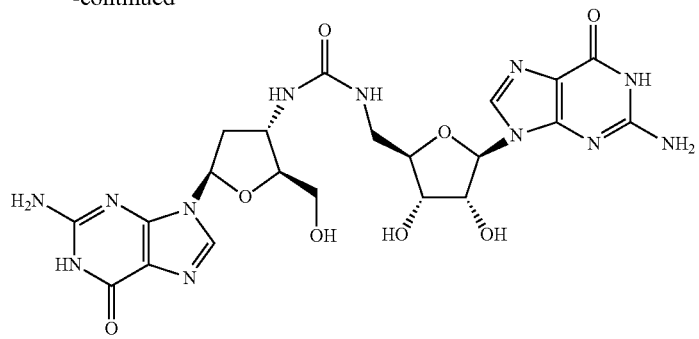

Example 26

2-Amino-9-((2R,4S,5R)-5-((1-((2S,3S,5R)-5-(2-amino-6-oxo-1H-purin-9(6H)-yl)-2-(hydroxymethyl)tetrahydrofuran-3-yl)-1H-1,2,3-triazol-4-yl)methyl)-4-hydroxytetrahydrofuran-2-yl)-1H-purin-6(9H)-one The title compound is prepared according to General Procedure 1 as follows:

Example 27

2-Amino-9-((2R,4S,5R)-5-(1-((2S,3S,5R)-5-(2-amino-6-oxo-1H-purin-9(6H)-yl)-2-(hydroxymethyl)tetrahydrofuran-3-yl)-1H-1,2,3-triazol-4-yl)-4-hydroxytetrahydrofuran-2-yl)-1H-purin-6(9H)-one The title compound is prepared according to General Procedure 1 as follows:

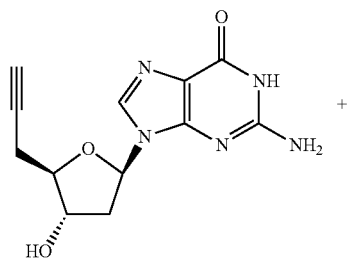

+

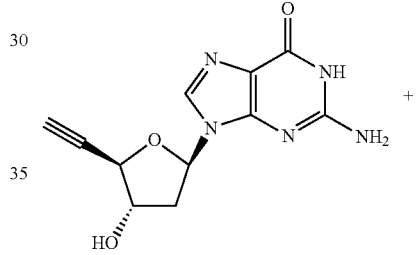

+

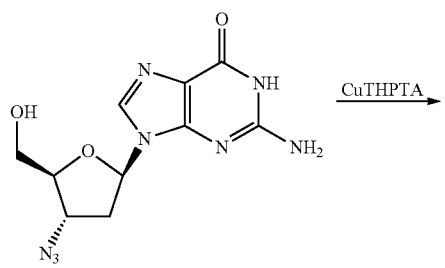

CuTHPTA→

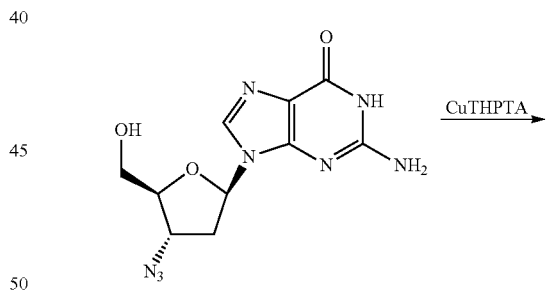

CuTHPTA→

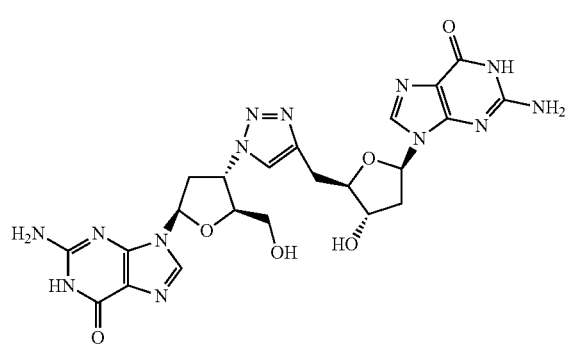

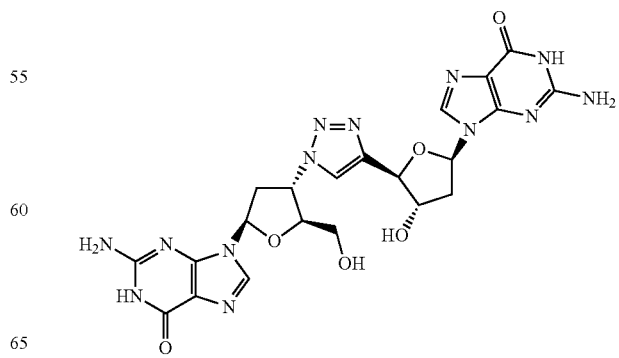

Example 28

2-Amino-9-((2R,4S,5R)-5-((4-((((2R,3S,5R)-5-(2-amino-6-oxo-1H-purin-9(6H)-yl)-2-(hydroxymethyl)tetrahydrofuran-3-yl)oxy)methyl)-1H-1,2,3-triazol-1-yl)methyl)-4-hydroxytetrahydrofuran-2-yl)-1H-purin-6(9H)-one The title compound is prepared according to General Procedure 1 as follows:

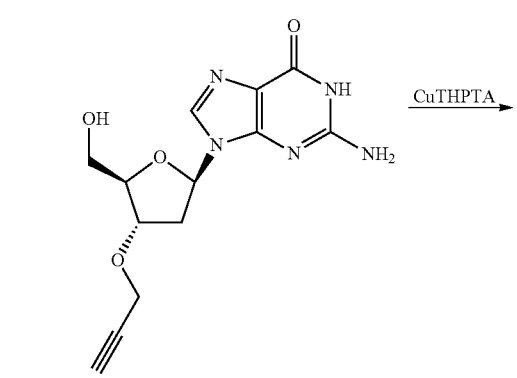

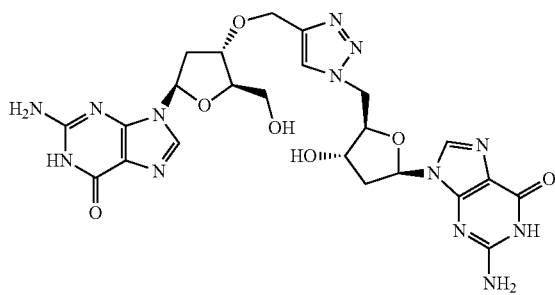

Example 29

2-Amino-9-((2R,4S,5R)-5-(2-(2-((2S,3S,5R)-5-(2-amino-6-oxo-1H-purin-9(6H)-yl)-2-(hydroxymethyl)tetrahydrofuran-3-yl)hydrazinyl)ethyl)-4-hydroxytetrahydrofuran-2-yl)-1H-purin-6(9H)-one The title compound is prepared according to General Procedure 2 as follows:

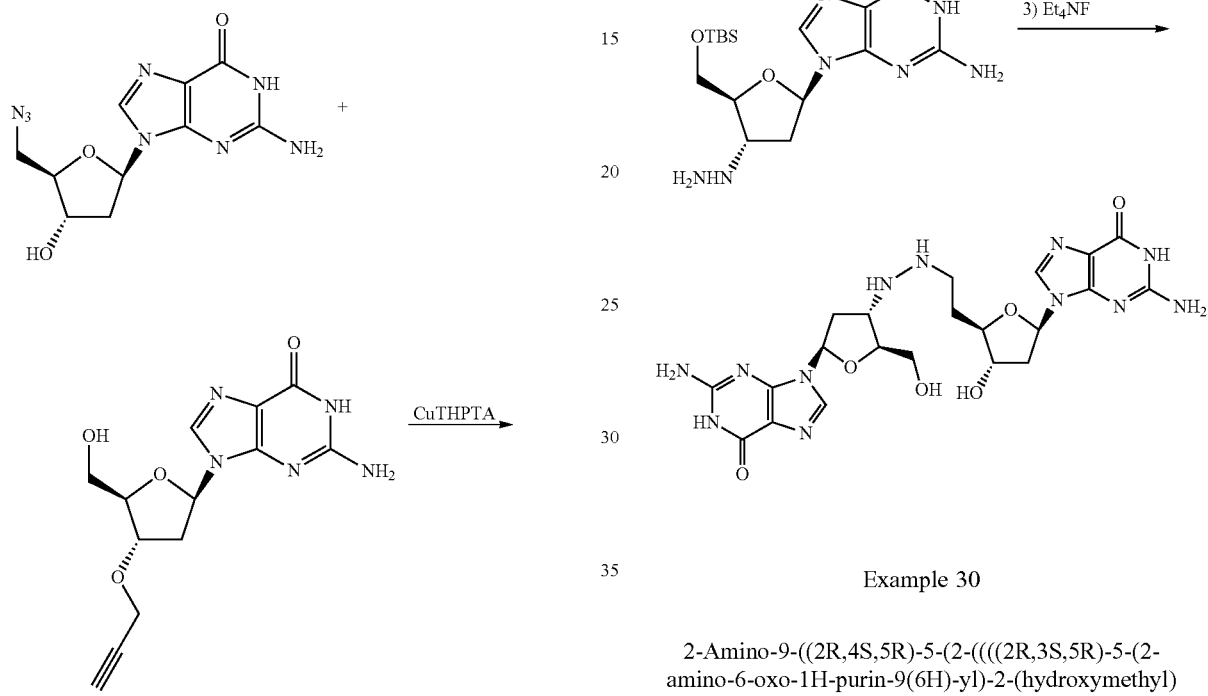

Example 30

2-Amino-9-((2R,4S,5R)-5-(2-((((2R,3S,5R)-5-(2-amino-6-oxo-1H-purin-9(6H)-yl)-2-(hydroxymethyl)tetrahydrofuran-3-yl)oxy)amino)ethyl)-4-hydroxytetrahydrofuran-2-yl)-1H-purin-6(9H)-one The title compound is prepared according to General Procedure 3 as follows:

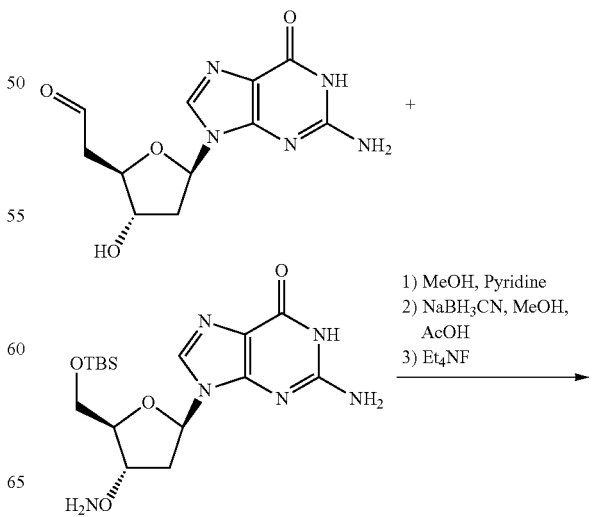

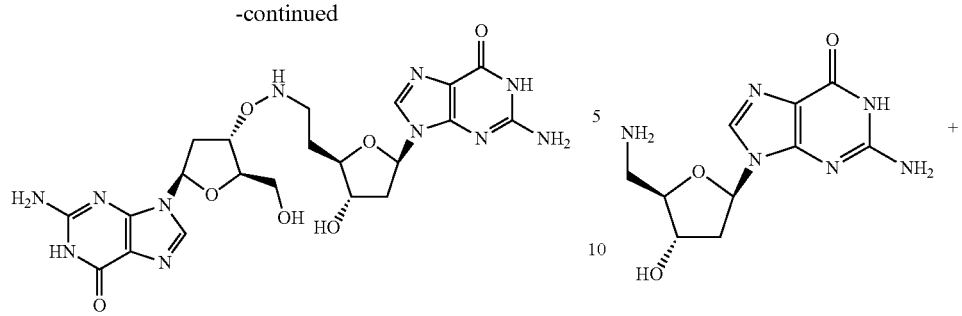

Example 31

2-Amino-9-((2R,4S,5R)-5-((2-((2S,3S,5R)-5-(2-amino-6-oxo-1H-purin-9(6H)-yl)-2-(hydroxymethyl)tetrahydrofuran-3-yl)hydrazinyl)methyl)-4-hydroxytetrahydrofuran-2-yl)-1H-purin-6(9H)-one The title compound is prepared according to General Procedure 2 as follows:

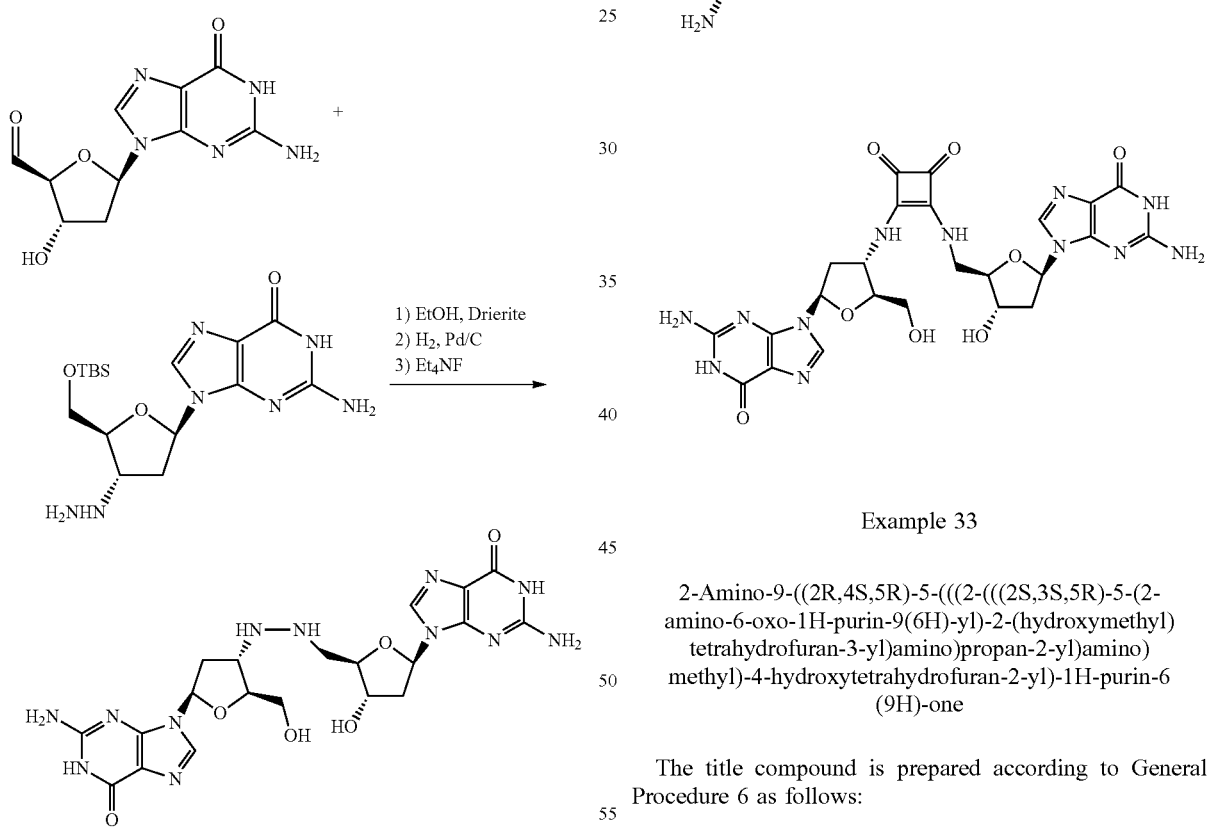

Example 32

3-(((2S,3S,5R)-5-(2-amino-6-oxo-1H-purin-9(6H)-yl)-2-(hydroxymethyl)tetrahydrofuran-3-yl)amino)-4-((((2R,3S,5R)-5-(2-amino-6-oxo-1H-purin-9(6H)-yl)-3-hydroxytetrahydrofuran-2-yl)methyl)amino)cyclobut-3-ene-1,2-dione The title compound is prepared according to General Procedure 5 as follows:

Example 33

2-Amino-9-((2R,4S,5R)-5-(((2-(((2S,3S,5R)-5-(2-amino-6-oxo-1H-purin-9(6H)-yl)-2-(hydroxymethyl)tetrahydrofuran-3-yl)amino)propan-2-yl)amino)methyl)-4-hydroxytetrahydrofuran-2-yl)-1H-purin-6(9H)-one The title compound is prepared according to General Procedure 6 as follows:

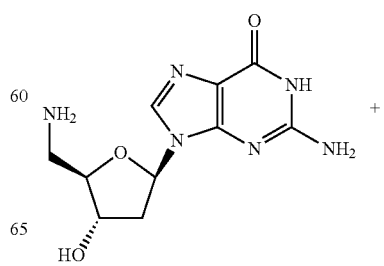

-continued

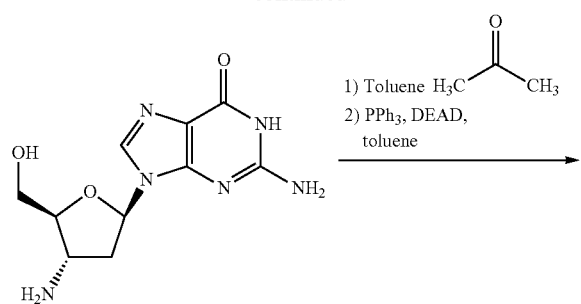

Example 34

2-Amino-9-((2R,4S,5R)-5-(((2-(((2S,3S,5R)-5-(2-amino-6-oxo-1H-purin-9(6H)-yl)-2-(hydroxymethyl)tetrahydrofuran-3-yl)amino)-1,1,1,3,3,3-hexafluoropropan-2-yl)amino)methyl)-4-hydroxytetrahydrofuran-2-yl)-1H-purin-6(9H)-one The title compound is prepared according to General Procedure 7 as follows:

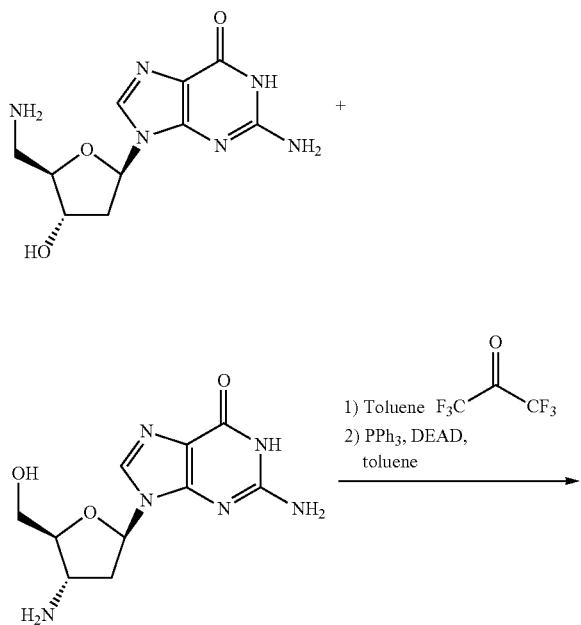

-continued

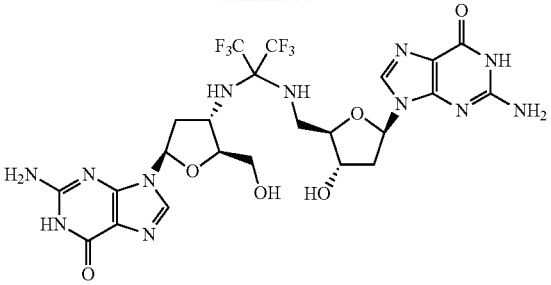

Example 35

2-Amino-9-((2R,4S,5R)-5-((((((2S,3S,5R)-5-(2-amino-6-oxo-1H-purin-9(6H)-yl)-2-(hydroxymethyl)tetrahydrofuran-3-yl)amino)dimethylsilyl)amino)methyl)-4-hydroxytetrahydrofuran-2-yl)-1H-purin-6(9H)-one The title compound is prepared according to General Procedure 8 as follows:

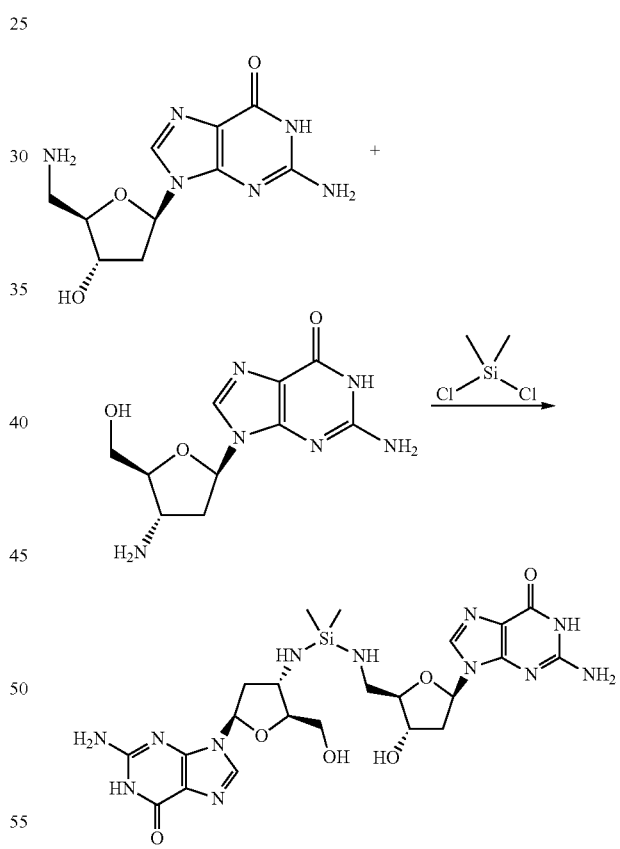

Example 36

1-((2S,3S,5R)-5-(2-amino-6-oxo-1H-purin-9(6H)-yl)-2-(hydroxymethyl)tetrahydrofuran-3-yl)-3-(((2R,3S,5R)-5-(2-amino-6-oxo-1H-purin-9(6H)-yl)-3-hydroxytetrahydrofuran-2-yl)methyl)urea The title compound is prepared according to General Procedure 9 as follows:

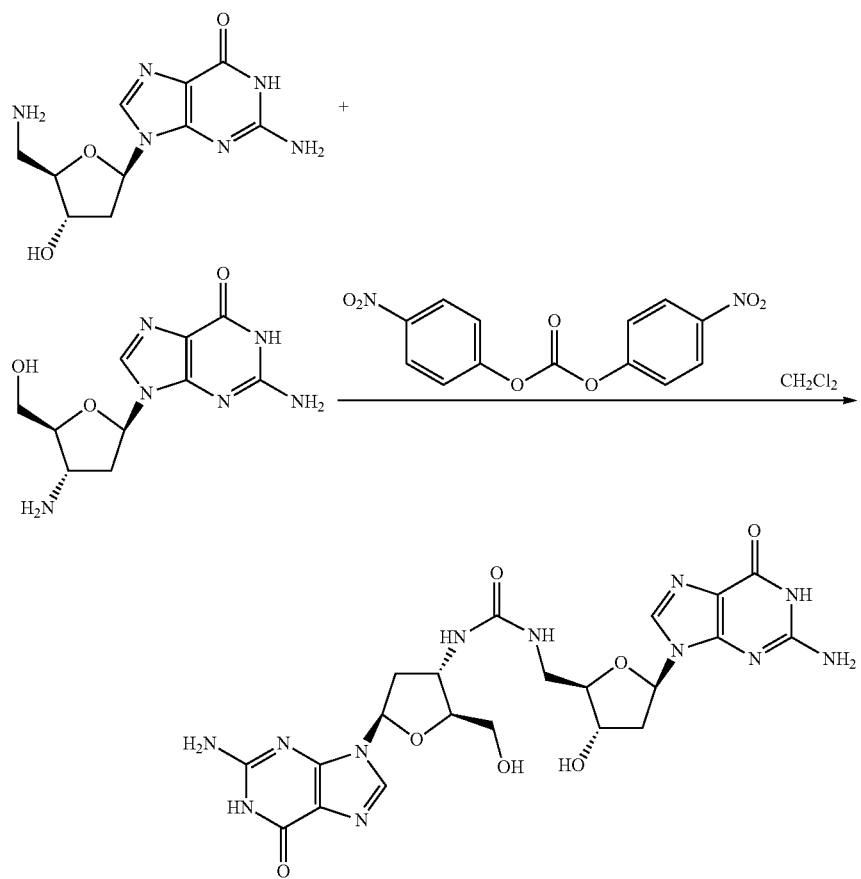
Example 37
2-Amino-9-((2R,3R,4S,5S)-4-(4-(((2R,3S,4R,5R)-5-(2-amino-6-oxo-1H-purin-9(6H)-yl)-3,4-dihydroxytetrahydrofuran-2-yl)methyl)-1H-1,2,3-triazol-1-yl)-3-hydroxy-5-(hydroxymethyl)tetrahydrofuran-2-yl)-1H-purin-6(9H)-one
The title compound is prepared according to General Procedure 1 as follows:
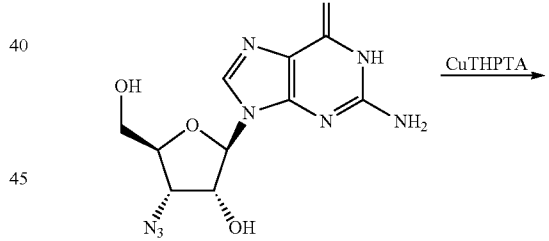
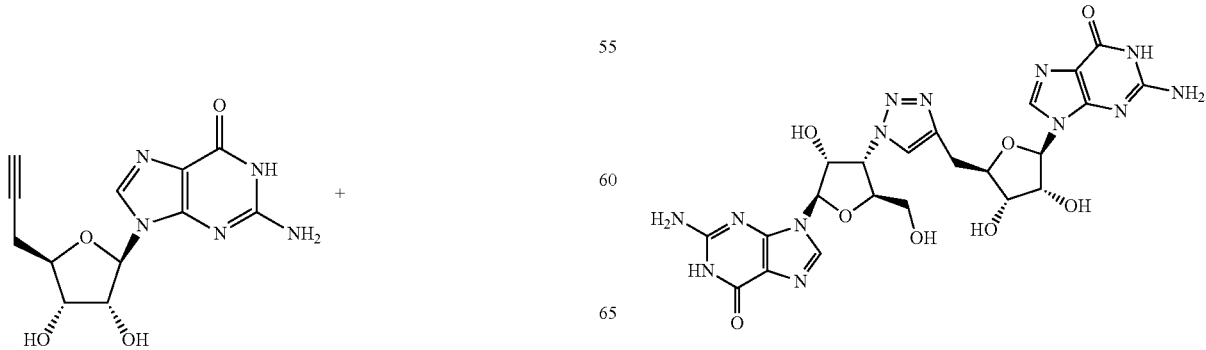

Example 38

2-Amino-9-((2R,3R,4S,5S)-4-(4-((2R,3S,4R,5R)-5-(2-amino-6-oxo-1H-purin-9(6H)-yl)-3,4-dihydroxytetrahydrofuran-2-yl)-1H-1,2,3-triazol-1-yl)-3-hydroxy-5-(hydroxymethyl)tetrahydrofuran-2-yl)-1H-purin-6(9H)-one The title compound is prepared according to General Procedure 1 as follows:

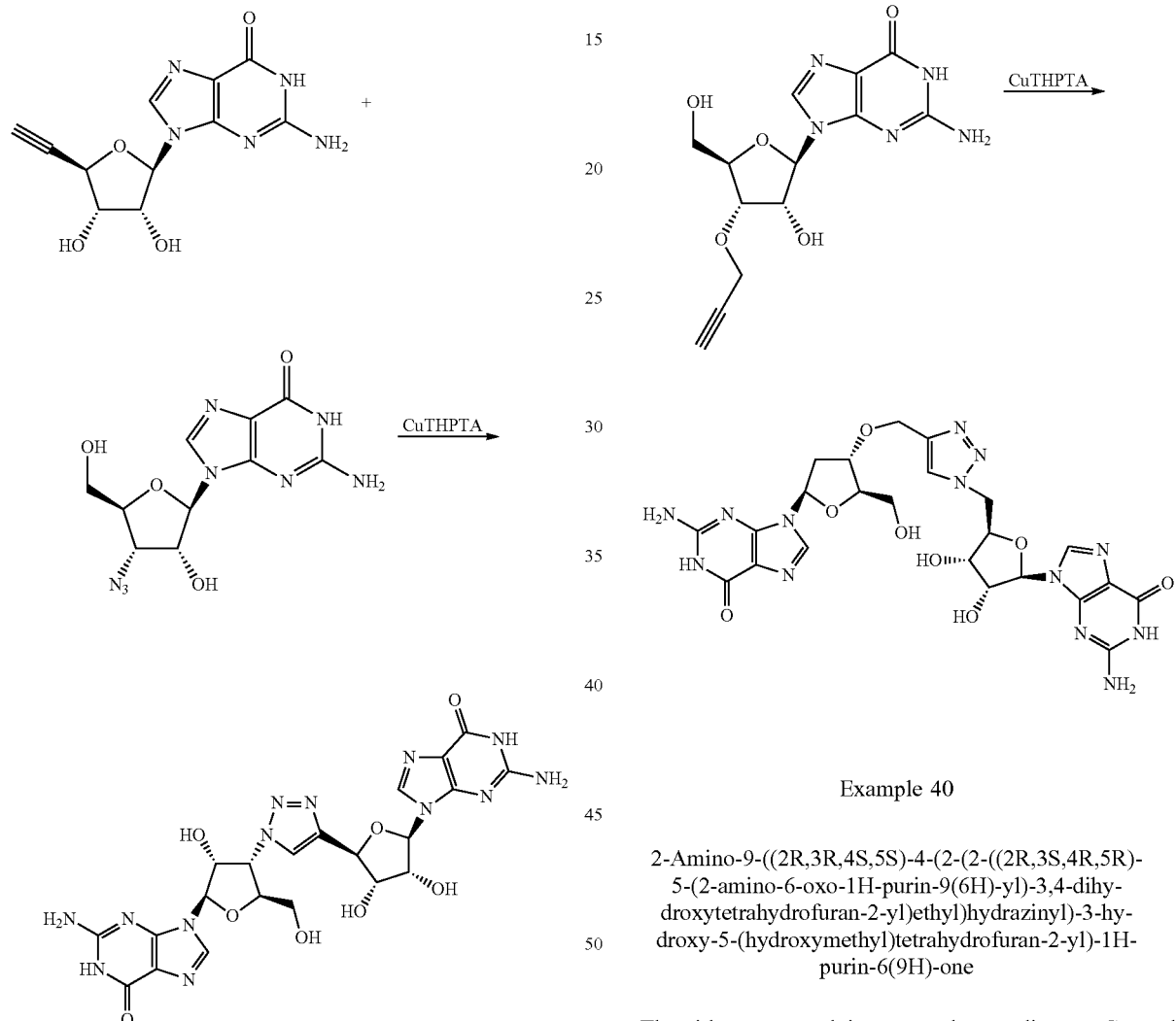

Example 39

2-Amino-9-((2R,3R,4S,5R)-5-((4-((((2R,3S,5R)-5-(2-amino-6-oxo-1H-purin-9(6H)-yl)-2-(hydroxymethyl)tetrahydrofuran-3-yl)oxy)methyl)-1H-1,2,3-triazol-1-yl)methyl)-3,4-dihydroxytetrahydrofuran-2-yl)-1H-purin-6(9H)-one The title compound is prepared according to General Procedure 1 as follows:

Example 40

2-Amino-9-((2R,3R,4S,5S)-4-(2-(2-((2R,3S,4R,5R)-5-(2-amino-6-oxo-1H-purin-9(6H)-yl)-3,4-dihydroxytetrahydrofuran-2-yl)ethyl)hydrazinyl)-3-hydroxy-5-(hydroxymethyl)tetrahydrofuran-2-yl)-1H-purin-6(9H)-one The title compound is prepared according to General Procedure 2 as follows:

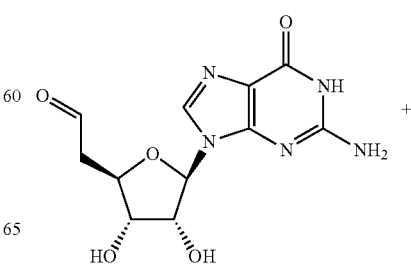

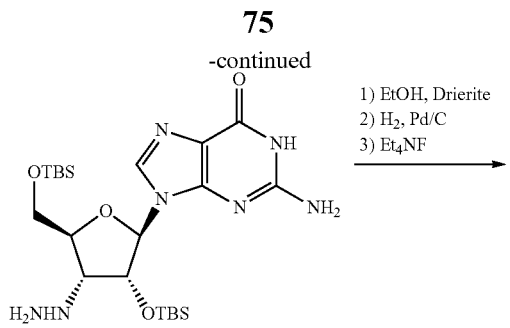

1) EtOH, Drierite
2) H₂, Pd/C
3) Et₄NF

Example 41

2-Amino-9-((2R,3R,4S,5R)-4-(((2-((2R,3S,4R,5R)-5-(2-amino-6-oxo-1H-purin-9(6H)-yl)-3,4-dihydroxytetrahydrofuran-2-yl)ethyl)amino)oxy)-3-hydroxy-5-(hydroxymethyl)tetrahydrofuran-2-yl)-1H-purin-6(9H)-one The title compound is prepared according to General Procedure 3 as follows:

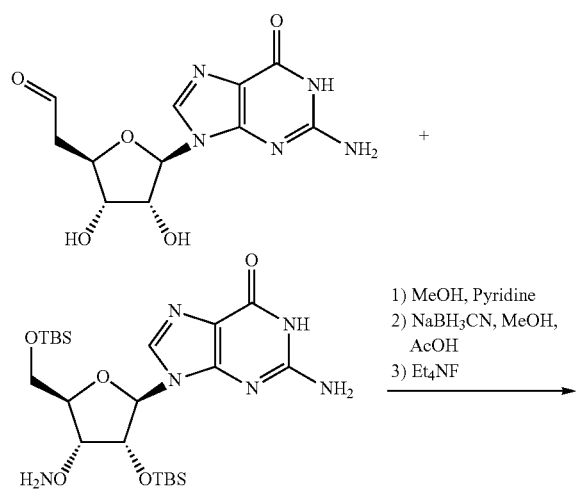

1) MeOH, Pyridine
2) NaBH₃CN, MeOH, AcOH
3) Et₄NF

Example 42

2-Amino-9-((2R,3R,4S,5S)-4-(2-(((2R,3S,4R,5R)-5-(2-amino-6-oxo-1H-purin-9(6H)-yl)-3,4-dihydroxytetrahydrofuran-2-yl)methyl)hydrazinyl)-3-hydroxy-5-(hydroxymethyl)tetrahydrofuran-2-yl)-1H-purin-6(9H)-one The title compound is prepared according to General Procedure 2 as follows:

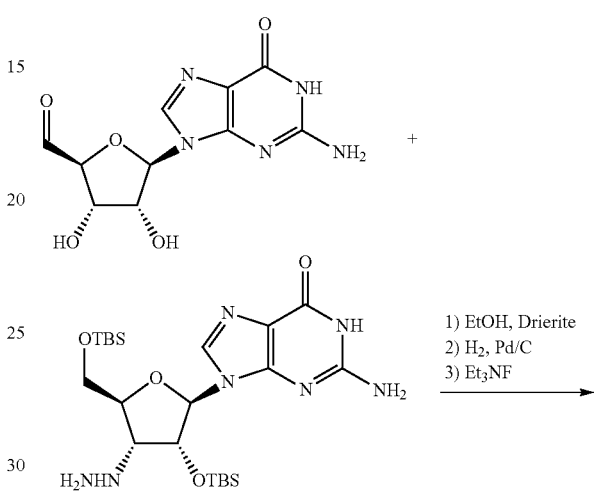

1) EtOH, Drierite
2) H₂, Pd/C
3) Et₃NF

Example 43

3-((((2R,3S,4R,5R)-5-(2-amino-6-oxo-1H-purin-9(6H)-yl)-3,4-dihydroxytetrahydrofuran-2-yl)methyl)amino)-4-(((2S,3S,4R,5R)-5-(2-amino-6-oxo-1H-purin-9(6H)-yl)-4-hydroxy-2-(hydroxymethyl)tetrahydrofuran-3-yl)amino)cyclobut-3-ene-1,2-dione The title compound is prepared according to General Procedure 5 as follows:

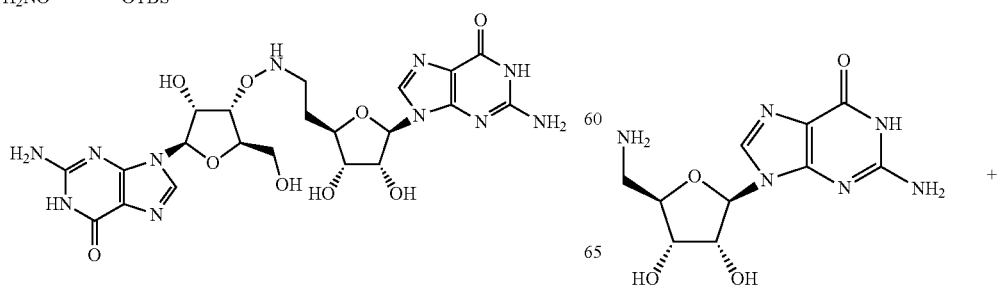

-continued

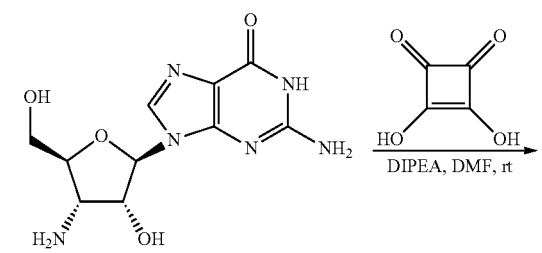

Example 44

2-Amino-9-((2R,3R,4S,5S)-4-((2-((((2R,3S,4R,5R)-5-(2-amino-6-oxo-1H-purin-9(6H)-yl)-3,4-dihydroxytetrahydrofuran-2-yl)methyl)amino)propan-2-yl)amino)-3-hydroxy-5-(hydroxymethyl)tetrahydrofuran-2-yl)-1H-purin-6(9H)-one The title compound is prepared according to General Procedure 6 as follows:

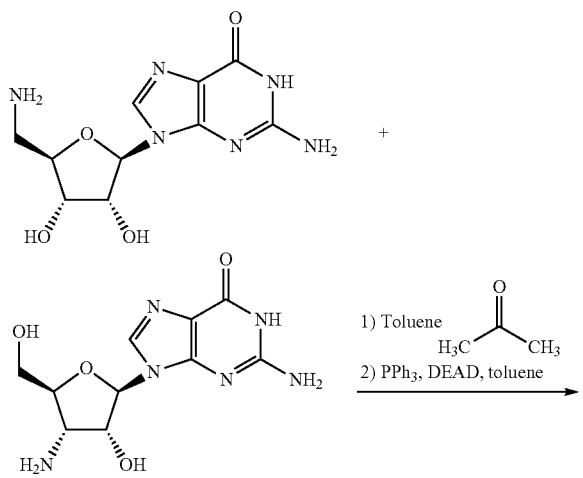

Example 45

2-Amino-9-((2R,3R,4S,5S)-4-((2-((((2R,3S,4R,5R)-5-(2-amino-6-oxo-1H-purin-9(6H)-yl)-3,4-dihydroxytetrahydrofuran-2-yl)methyl)amino)-1,1,1,3,3,3-hexafluoropropan-2-yl)amino)-3-hydroxy-5-(hydroxymethyl)tetrahydrofuran-2-yl)-1H-purin-6(9H)-one The title compound is prepared according to General Procedure 7 as follows:

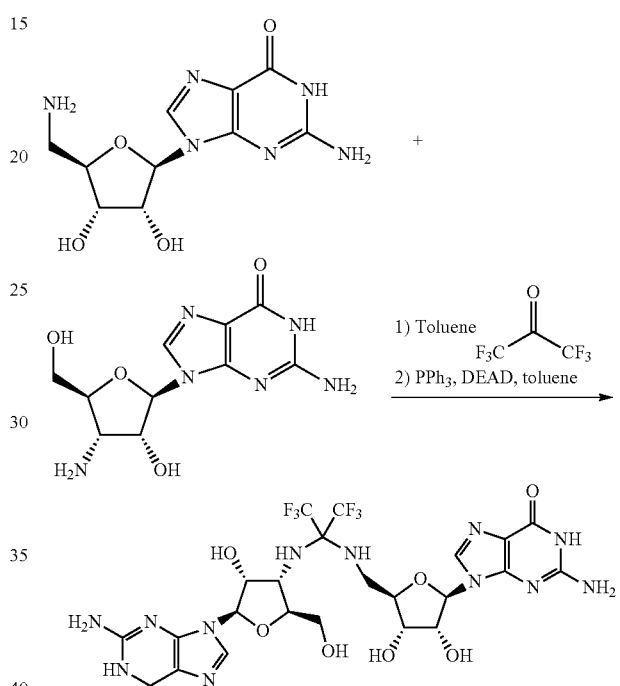

Example 46

2-Amino-9-((2R,3R,4S,5S)-4-((((((2R,3S,4R,5R)-5-(2-amino-6-oxo-1H-purin-9(6H)-yl)-3,4-dihydroxytetrahydrofuran-2-yl)methyl)amino)dimethylsilyl)amino)-3-hydroxy-5-(hydroxymethyl)tetrahydrofuran-2-yl)-1H-purin-6(9H)-one The title compound is prepared according to General Procedure 8 as follows:

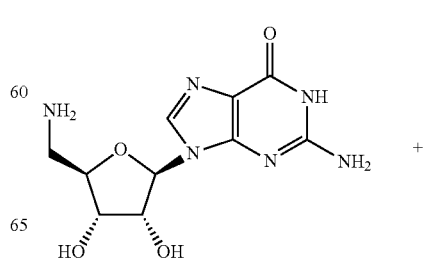

-continued

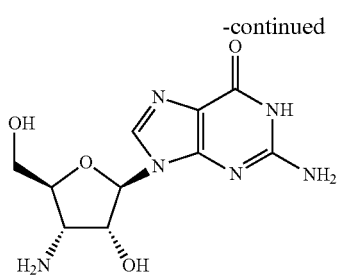 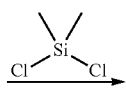

Example 48

2-amino-9-((2R,3R,4S,5R)-5-(((((2S,3S,5R)-5-(2-amino-6-oxo-1H-purin-9(6H)-yl)-2-(hydroxymethyl)tetrahydrofuran-3-yl)sulfamide)methyl)-3,4-dihydroxytetrahydrofuran-2-yl)-1H-purin-6(9H)-one The title compound is prepared according to General Procedure 4 as follows:

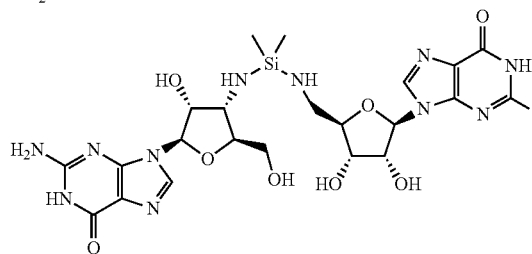

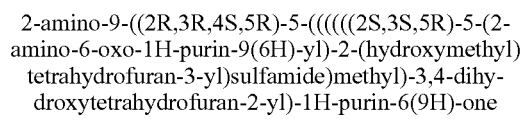

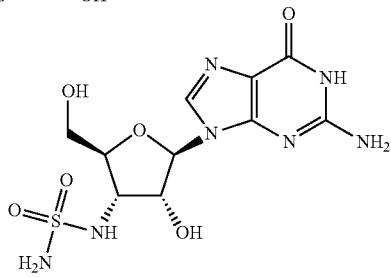

Example 47

1-(((2R,3S,4R,5R)-5-(2-amino-6-oxo-1H-purin-9(6H)-yl)-3,4-dihydroxytetrahydrofuran-2-yl)methyl)-3-((2S,3S,4R,5R)-5-(2-amino-6-oxo-1H-purin-9(6H)-yl)-4-hydroxy-2-(hydroxymethyl)tetrahydrofuran-3-yl)urea The title compound is prepared according to General Procedure 9 as follows:

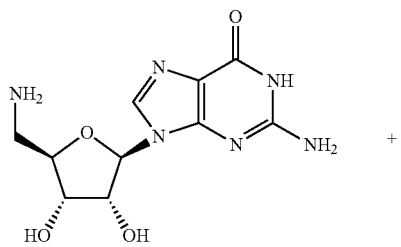

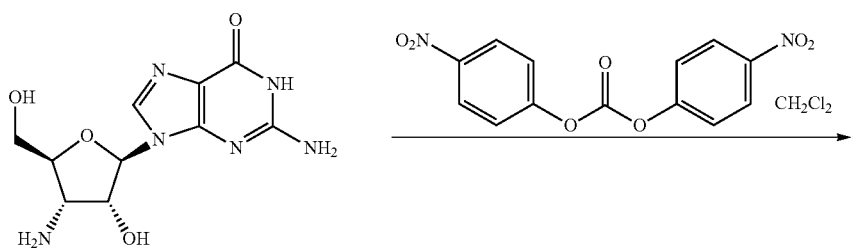

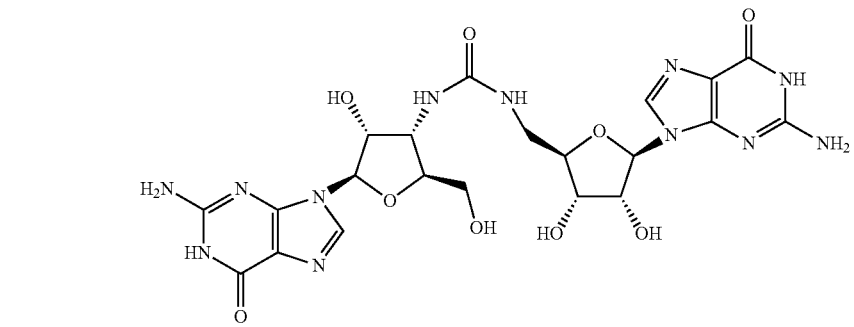

81

-continued

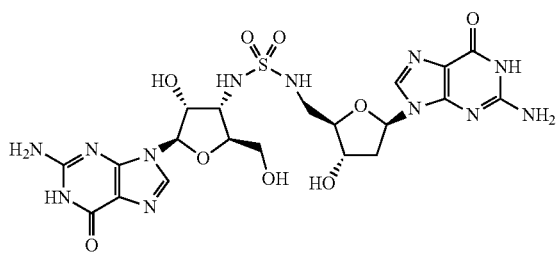

Example 49

2-amino-9-((2R,3R,4S,5R)-5-((((((2S,3S,5R)-5-(2-amino-6-oxo-1H-purin-9(6H)-yl)-2-(hydroxymethyl)tetrahydrofuran-3-yl)sulfamide)methyl)-3,4-dihydroxytetrahydrofuran-2-yl)-1H-purin-6(9H)-one The title compound is prepared according to General Procedure 4 as follows:

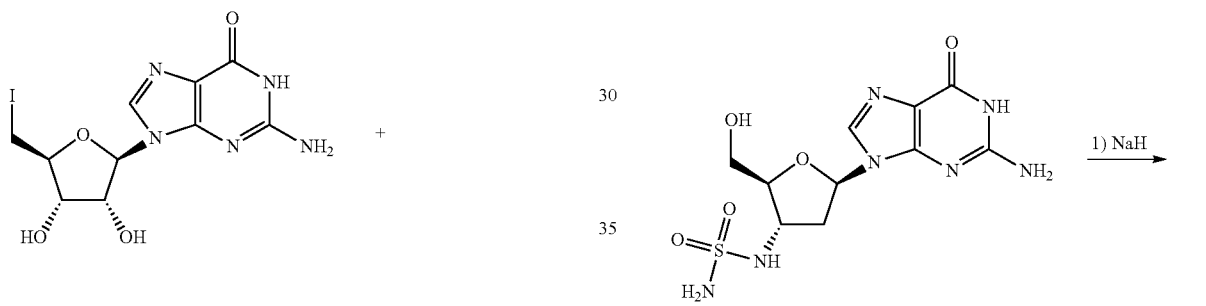

Example 50

2-amino-9-((2R,4S,5R)-5-((((((2S,3S,5R)-5-(2-amino-6-oxo-1H-purin-9(6H)-yl)-2-(hydroxymethyl)tetrahydrofuran-3-yl)sulfamide)methyl)-4-hydroxytetrahydrofuran-2-yl)-1H-purin-6(9H)-one The title compound is prepared according to General Procedure 4 as follows:

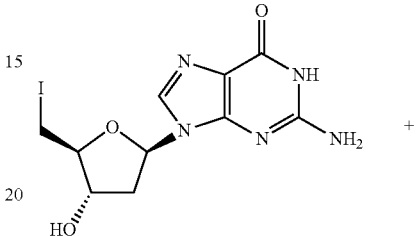

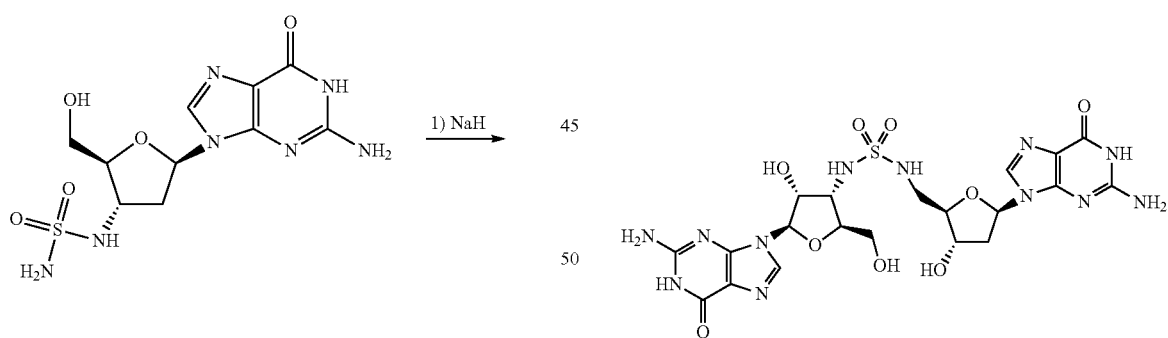

Example 51

2-amino-9-((2R,3R,4S,5S)-4-((((((2R,3S,4R,5R)-5-(2-amino-6-oxo-1H-purin-9(6H)-yl)-3,4-dihydroxytetrahydrofuran-2-yl)methyl)sulfamide)-3-hydroxy-5-(hydroxymethyl)tetrahydrofuran-2-yl)-1H-purin-6(9H)-one The title compound is prepared according to General Procedure 4 as follows:

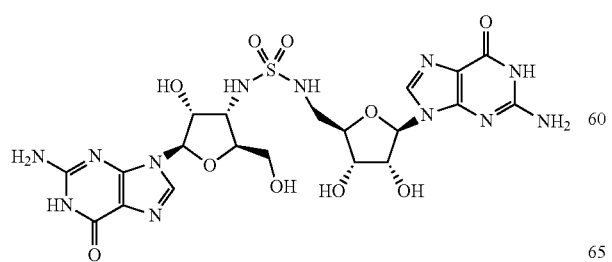

83
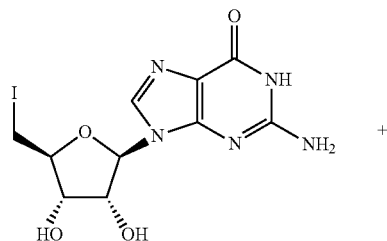
+
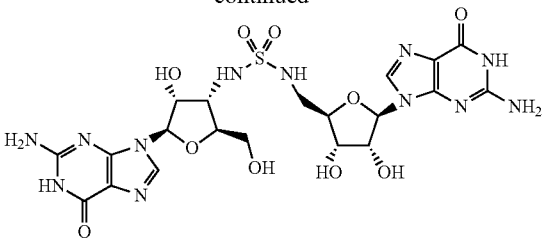
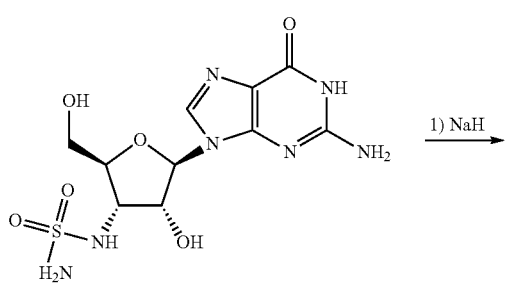
1) NaH →
84
-continued
Example 52
((2S,3S,4R,5R)-5-(2-amino-6-oxo-1H-purin-9(6H)-yl)-3-(4-(((2R,3S,4R,5R)-5-(2-amino-6-oxo-1H-purin-9(6H)-yl)-3,4-dihydroxytetrahydrofuran-2-yl)methyl)-1H-1,2,3-triazol-1-yl)-4-hydroxytetrahydrofuran-2-yl)methyl 5-((3aS,4S,6aR)-2-oxohexahydro-1H-thieno[3,4]imidazol-4-yl)pentanoate
The title compound is prepared as follows, generally according to the related reaction procedures of Wulff, J. JACS, 2007, 129, 4898:
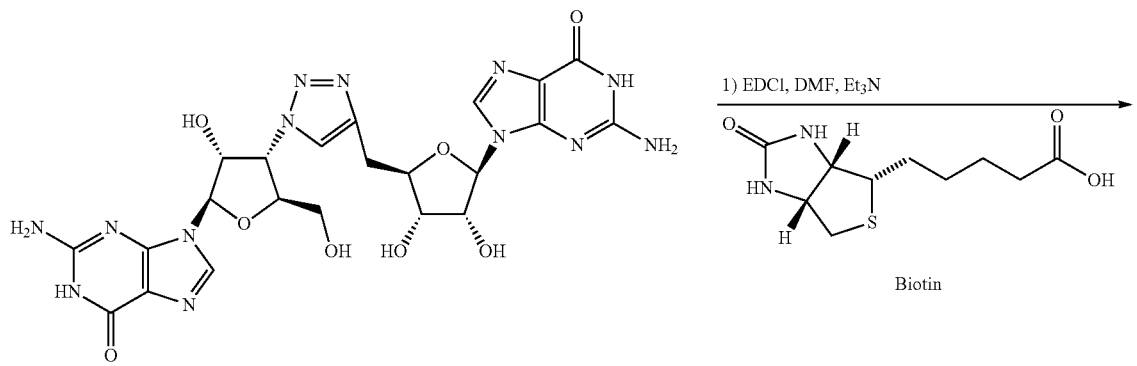
1) EDCl, DMF, Et$_3$N →
Biotin
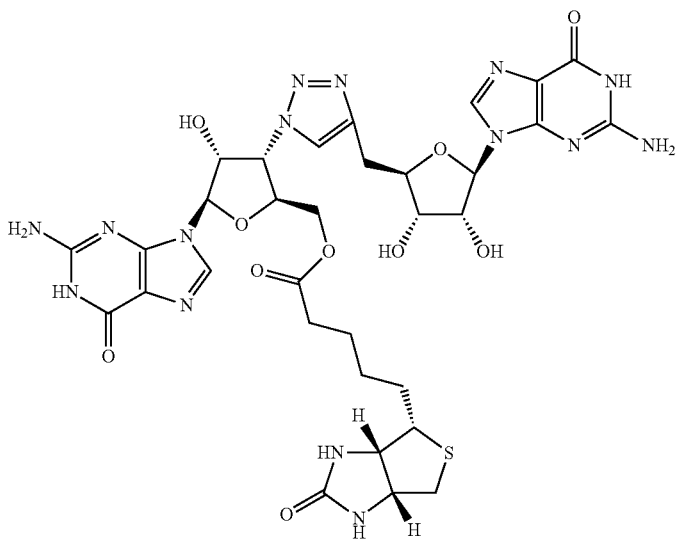

Example 53

(2R,3S,4R,5R)-5-(2-amino-6-oxo-1H-purin-9(6H)-yl)-2-((1-((2S,3S,4R,5R)-5-(2-amino-6-oxo-1H-purin-9(6H)-yl)-4-hydroxy-2-(hydroxymethyl)tetrahydrofuran-3-yl)-1H-1,2,3-triazol-4-yl)methyl)-4-hydroxytetrahydrofuran-3-yl 5-((3aS,4S,6aR)-2-oxohexahydro-1H-thieno[3,4]imidazol-4-yl)pentanoate The title compound is prepared as follows:

Example 54

2-amino-9-((2R,3R,4S,5R)-5-((1-((2S,3S,4R,5R)-5-(2-amino-6-oxo-1H-purin-9(6H)-yl)-2-((((4R)-4-(3-chlorophenyl)-2-oxido-1,3,2-dioxaphosphinan-2-yl)oxy)methyl)-4-hydroxytetrahydrofuran-3-yl)-1H-1,2,3-triazol-4-yl)methyl)-3,4-dihydroxytetrahydrofuran-2-yl)-1H-purin-6(9H)-one The title compound is prepared as follows, generally according to the related reaction procedures of Das, A. et al., *J. Med Chem.* 2010, 53, 471:

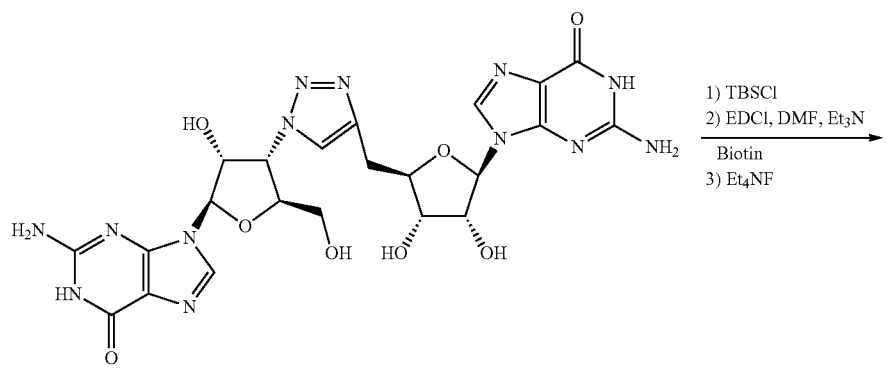

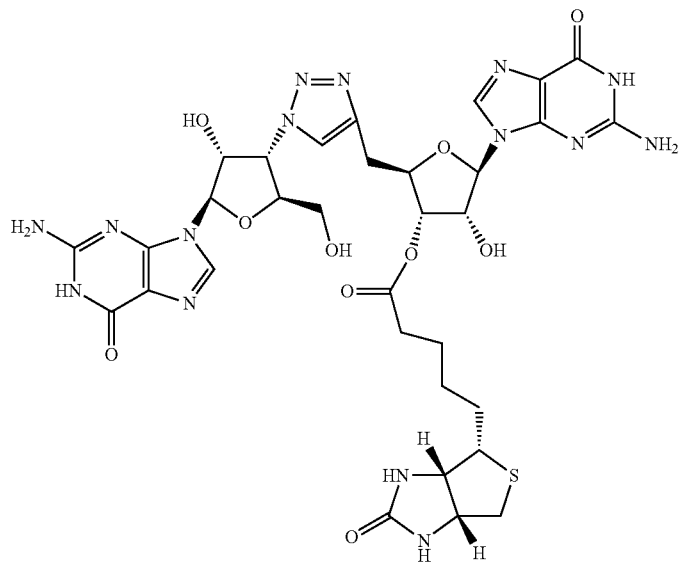

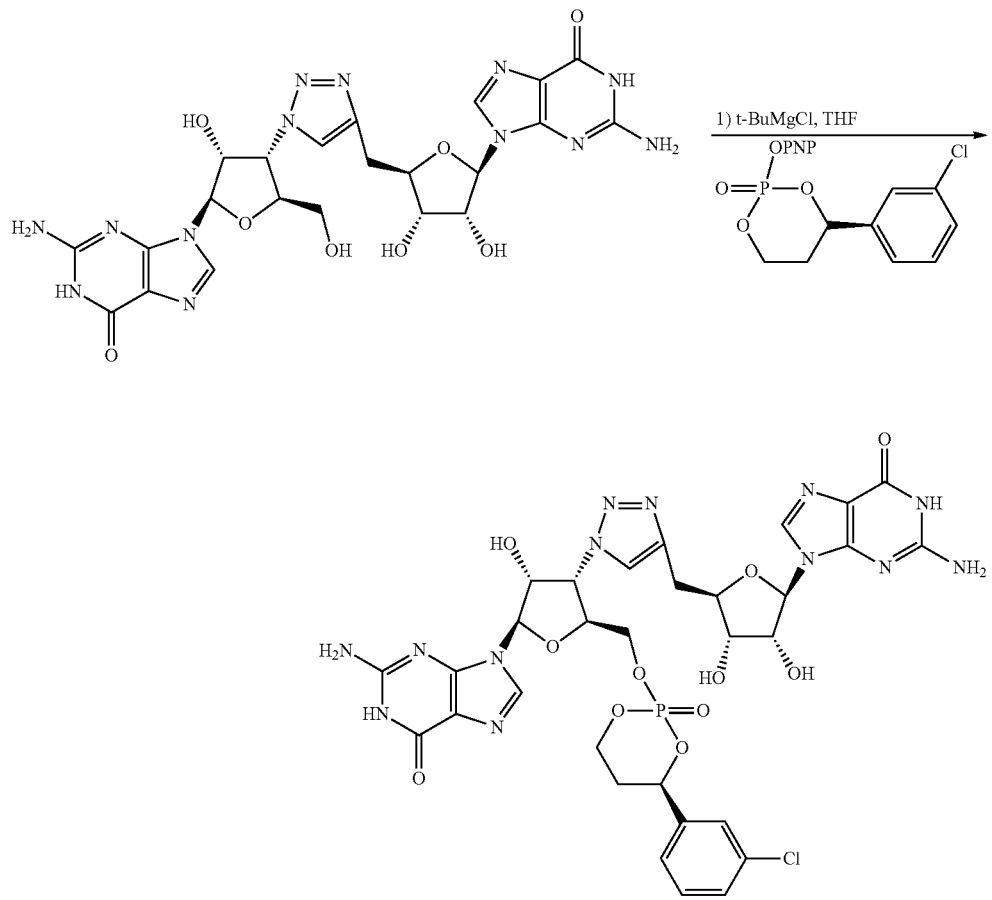
where "PNP" means p-nitrophenol.
Example 55
((2S,3S,4R,5R)-5-(2-amino-6-oxo-1H-purin-9(6H)-yl)-3-(4-(((2R,3S,4R,5R)-5-(2-amino-6-oxo-1H-purin-9(6H)-yl)-3,4-dihydroxytetrahydrofuran-2-yl)methyl)-1H-1,2,3-triazol-1-yl)-4-hydroxytetrahydrofuran-2-yl)methyl dihydrogen phosphate
The title compound is prepared as follows, generally according to the related reaction procedures of Das, A. et al., *J. Med Chem.* 2010, 53, 471:
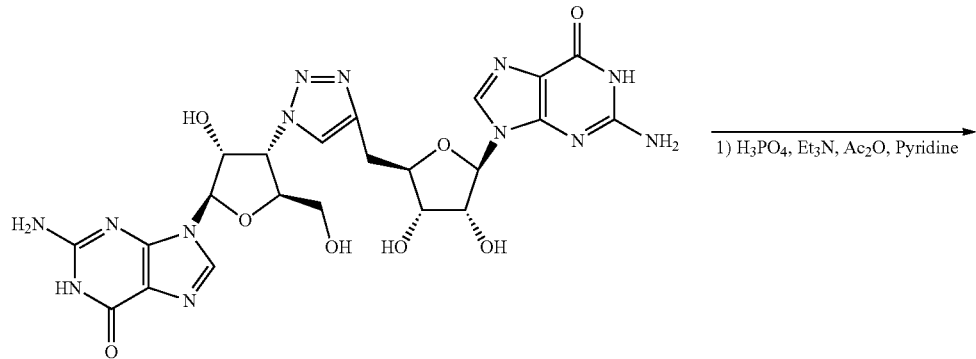

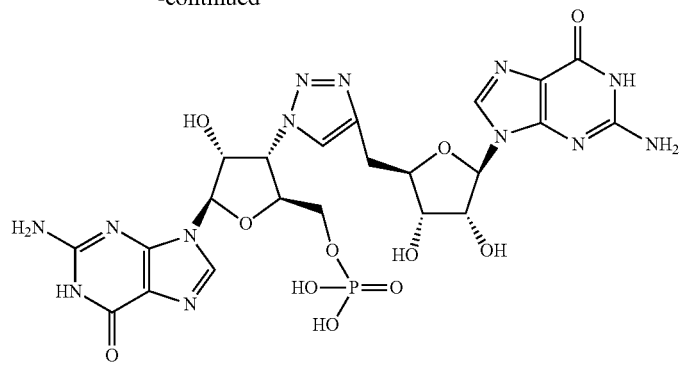

Example 56

The biofilm-formation inhibitory concentration of a compound can be determined as follows, according to the method of O'Toole et al., *Mol. Microbiol.* 1998, 28, 449. A known concentration of compound is added independently to a 96-well polyvinylchloride plastic microtitre dish containing planktonic *P. aeruginosa* cells suspended in M63 media with 0.2% glucose, 1 mM $MgSO_4$, 0.5% casamino acids, 0.4% citric acid, and 0.4% glutamic acid. The plates are incubated at room temperature for 15 min, rinsed thoroughly and repeatedly with water and scored for the formation of biofilm.

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indication the scope of the invention.

What is claimed is:

1. A compound of Formula I or a salt thereof:

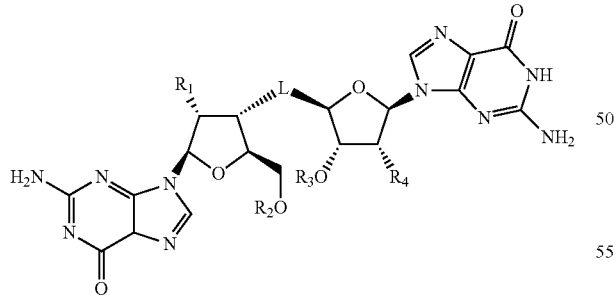

wherein:

L is selected from the group consisting of:

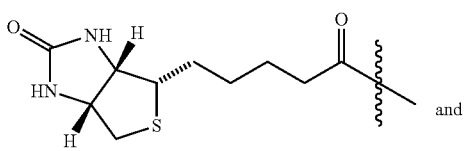

$R_1$ is selected from the group consisting of hydrogen, hydroxyl, $(C_1-C_6)$alkyl, $(C_1-C_6)$alkyloxy and $-OPO_3H_2$;

$R_2$ is selected from the group consisting of:
hydrogen,
$-PO_3H_2$,

-continued

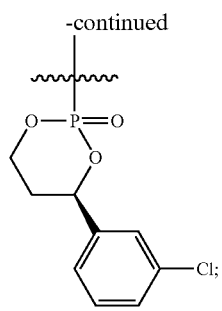

$R_3$ is selected from the group consisting of:
hydrogen,
—$PO_3H_2$,

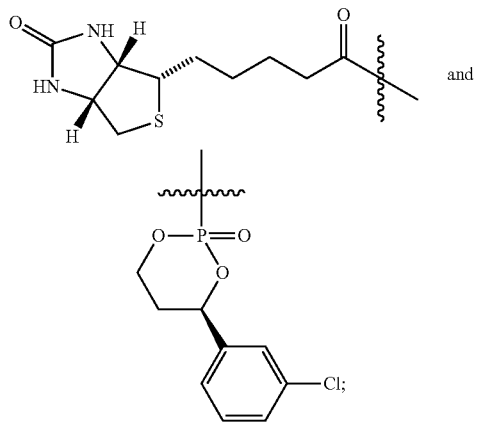

$R_4$ is selected from the group consisting of hydrogen, hydroxyl, ($C_1$-$C_6$)alkyl, ($C_1$-$C_6$)alkyloxy and —$OPO_3H_2$.

2. A compound according to claim 1, or a salt thereof, wherein at least one of $R_1$, $R_2$, $R_3$, and $R_4$ is hydrogen.

3. A compound according to claim 2 or a salt thereof, wherein at least one of $R_1$ and $R_4$ is hydrogen.

4. A compound according to claim 2, wherein L is:

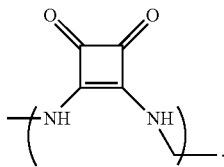

5. A compound according to claim 1, or a salt thereof, selected from the group consisting of:
2-amino-9-((2R,3R,4S,5S)-4-(4-(((2R,3S,5R)-5-(2-amino-6-oxo-1H-purin-9(6H)-yl)-3-hydroxytetrahydrofuran-2-yl)methyl)-1H-1,2,3-triazol-1-yl)-3-hydroxy-5-(hydroxymethyl)tetrahydrofuran-2-yl)-1H-purin-6(9H)-one;
2-amino-9-((2R,3R,4S,5S)-4-(4-((2R,3S,5R)-5-(2-amino-6-oxo-1H-purin-9(6H)-yl)-3-hydroxytetrahydrofuran-2-yl)-1H-1,2,3-triazol-1-yl)-3-hydroxy-5-(hydroxymethyl)tetrahydrofuran-2-yl)-1H-purin-6(9H)-one;
2-amino-9-((2R,3R,4S,5R)-4-((1-((2S,3S,5R)-5-(2-amino-6-oxo-1H-purin-9(6H)-yl)-3-hydroxytetrahydrofuran-2-yl)-1H-1,2,3-triazol-4-yl)methoxy)-3-hydroxy-5-(hydroxymethyl)tetrahydrofuran-2-yl)-1H-purin-6(9H)-one;
2-amino-9-((2R,3R,4S,5S)-4-(2-(2-((2R,3S,5R)-5-(2-amino-6-oxo-1H-purin-9(6H)-yl)-3-hydroxytetrahydrofuran-2-yl)ethyl)hydrazinyl)-3-hydroxy-5-(hydroxymethyl)tetrahydrofuran-2-yl)-1H-purin-6(9H)-one;
2-amino-9-((2R,3R,4S,5R)-4-(((2-((2R,3S,5R)-5-(2-amino-6-oxo-1H-purin-9(6H)-yl)-3-hydroxytetrahydrofuran-2-yl)ethyl)amino)oxy)-3-hydroxy-5-(hydroxymethyl)tetrahydrofuran-2-yl)-1H-purin-6(9H)-one;
2-amino-9-((2R,3R,4S,5S)-4-(2-(((2R,3S,5R)-5-(2-amino-6-oxo-1H-purin-9(6H)-yl)-3-hydroxytetrahydrofuran-2-yl)methyl)hydrazinyl)-3-hydroxy-5-(hydroxymethyl)tetrahydrofuran-2-yl)-1H-purin-6(9H)-one;
2-amino-9-((2R,3R,4S,5R)-4-(((((2R,3S,5R)-5-(2-amino-6-oxo-1H-purin-9(6H)-yl)-3-hydroxytetrahydrofuran-2-yl)methyl)amino)oxy)-3-hydroxy-5-(hydroxymethyl)tetrahydrofuran-2-yl)-1H-purin-6(9H)-one;
3-((((2R,3S,5R)-5-(2-amino-6-oxo-1H-purin-9(6H)-yl)-3-hydroxytetrahydrofuran-2-yl)methyl)amino)-4-(((2S,3S,4R,5R)-5-(2-amino-6-oxo-1H-purin-9(6H)-yl)-4-hydroxy-2-(hydroxymethyl)tetrahydrofuran-3-ylamino)cyclobut-3-ene-1,2-dione;
2-amino-9-((2R,3R,4S,5S)-4-((2-((((2R,3S,5R)-5-(2-amino-6-oxo-1H-purin-9(6H)-yl)-3-hydroxytetrahydrofuran-2-yl)methyl)amino)propan-2-yl)amino)-3-hydroxy-5-(hydroxymethyl)tetrahydrofuran-2-yl)-1H-purin-6(9H)-one;
2-amino-9-((2R,3R,4S,5S)-4-((2-(((((2R,3S,5R)-5-(2-amino-6-oxo-1H-purin-9(6H)-yl)-3-hydroxytetrahydrofuran-2-yl)methyl)amino)-1,1,1,3,3,3-hexafluoropropan-2-yl)amino)-3-hydroxy-5-(hydroxymethyl)tetrahydrofuran-2-yl)-1H-purin-6(9H)-one;
2-amino-9-((2R,3R,4S,5S)-4-((((((2R,3S,5R)-5-(2-amino-6-oxo-1H-purin-9(6H)-yl)-3-hydroxytetrahydrofuran-2-yl)methyl)amino)dimethylsilyl)amino)-3-hydroxy-5-(hydroxymethyl)tetrahydrofuran-2-yl)-1H-purin-6(9H)-one;
1-(((2R,3S,5R)-5-(2-amino-6-oxo-1H-purin-9(6H)-yl)-3-hydroxytetrahydrofuran-2-yl)methyl)-3-((2S,3S,4R,5R)-5-(2-amino-6-oxo-1H-purin-9(6H)-yl)-4-hydroxy-2-(hydroxymethyl)tetrahydrofuran-3-yl)urea;
2-amino-9-((2R,3R,4S,5R)-5-((1-((2S,3S,5R)-5-(2-amino-6-oxo-1H-purin-9(6H)-yl)-2-(hydroxymethyl)tetrahydrofuran-3-yl)-1H-1,2,3-triazol-4-yl)methyl)-3,4-dihydroxytetrahydrofuran-2-yl)-1H-purin-6(9H)-one;
2-amino-9-((2R,3R,4S,5R)-5-(1-((2S,3S,5R)-5-(2-amino-6-oxo-1H-purin-9(6H)-yl)-2-(hydroxymethyl)tetrahydrofuran-3-yl)-1H-1,2,3-triazol-4-yl)-3,4-dihydroxytetrahydrofuran-2-yl)-1H-purin-6(9H)-one;
2-amino-9-((2R,3R,4S,5S)-5-(4-((((2R,3S,5R)-5-(2-amino-6-oxo-1H-purin-9(6H)-yl)-2-(hydroxymethyl)tetrahydrofuran-3-yl)oxy)methyl)-1H-1,2,3-triazol-1-yl)-3,4-dihydroxytetrahydrofuran-2-yl)-1H-purin-6(9H)-one;
2-amino-9-((2R,3R,4S,5R)-5-(2-(2-((2S,3S,5R)-5-(2-amino-6-oxo-1H-purin-9(6H)-yl)-2-(hydroxymethyl)tetrahydrofuran-3-yl)hydrazinyl)ethyl)-3,4-dihydroxytetrahydrofuran-2-yl)-1H-purin-6(9H)-one;
2-amino-9-((2R,3R,4S,5R)-5-(2-((((2R,3S,5R)-5-(2-amino-6-oxo-1H-purin-9(6H)-yl)-2-(hydroxymethyl)

tetrahydrofuran-3-yl)oxy)amino)ethyl)-3,4-dihydroxytetrahydrofuran-2-yl)-1H-purin-6(9H)-one;

2-amino-9-((2R,3R,4S,5R)-5-((2-((2S,3S,5R)-5-(2-amino-6-oxo-1H-purin-9(6H)-yl)-2-(hydroxymethyl)tetrahydrofuran-3-yl)hydrazinyl)methyl)-3,4-dihydroxytetrahydrofuran-2-yl)-1H-purin-6(9H)-one;

2-amino-9-((2R,3R,4S,5R)-5-(((((2R,3S,5R)-5-(2-amino-6-oxo-1H-purin-9(6H)-yl)-2-(hydroxymethyl)tetrahydrofuran-3-yl)oxy)amino)methyl)-3,4-dihydroxytetrahydrofuran-2-yl)-1H-purin-6(9H)-one;

3-(((2S,3S,5R)-5-(2-amino-6-oxo-1H-purin-9(6H)-yl)-2-(hydroxymethyl)tetrahydrofuran-3-yl)amino)-4-((((2R,3S,4R,5R)-5-(2-amino-6-oxo-1H-purin-9(6H)-yl)-3,4-dihydroxytetrahydrofuran-2-yl)methyl)amino)cyclobut-3-ene-1,2-dione;

2-amino-9-((2R,3R,4S,5R)-5-(((2-(((2S,3S,5R)-5-(2-amino-6-oxo-1H-purin-9(6H)-yl)-2-(hydroxymethyl)tetrahydrofuran-3-yl)amino)propan-2-yl)amino)methyl)-3,4-dihydroxytetrahydrofuran-2-yl)-1H-purin-6(9H)-one;

2-amino-9-((2R,3R,4S,5R)-5-(((2-(((2S,3S,5R)-5-(2-amino-6-oxo-1H-purin-9(6H)-yl)-2-(hydroxymethyl)tetrahydrofuran-3-yl)amino)-1,1,1,3,3,3-hexafluoropropan-2-yl)amino)methyl)-3,4-dihydroxytetrahydrofuran-2-yl)-1H-purin-6(9H)-one;

2-amino-9-((2R,3R,4S,5R)-5-((((((2S,3S,5R)-5-(2-amino-6-oxo-1H-purin-9(6H)-yl)-2-(hydroxymethyl)tetrahydrofuran-3-yl)amino)dimethylsilyl)amino)methyl)-3,4-dihydroxytetrahydrofuran-2-yl)-1H-purin-6(9H)-one;

1-((2S,3S,5R)-5-(2-amino-6-oxo-1H-purin-9(6H)-yl)-2-(hydroxymethyl)tetrahydrofuran-3-yl)-3-(((2R,3S,4R,5R)-5-(2-amino-6-oxo-1H-purin-9(6H)-yl)-3,4-dihydroxytetrahydrofuran-2-yl)methyl)urea;

2-amino-9-((2R,4S,5R)-5-((1-((2S,3S,5R)-5-(2-amino-6-oxo-1H-purin-9(6H)-yl)-2-(hydroxymethyl)tetrahydrofuran-3-yl)-1H-1,2,3-triazol-4-yl)methyl)-4-hydroxytetrahydrofuran-2-yl)-1H-purin-6(9H)-one;

2-amino-9-((2R,4S,5R)-5-(1-((2S,3S,5R)-5-(2-amino-6-oxo-1H-purin-9(6H)-yl)-2-(hydroxymethyl)tetrahydrofuran-3-yl)-1H-1,2,3-triazol-4-yl)-4-hydroxytetrahydrofuran-2-yl)-1H-purin-6(9H)-one;

2-amino-9-((2R,4S,5R)-5-((4-((((2R,3S,5R)-5-(2-amino-6-oxo-1H-purin-9(6H)-yl)-2-(hydroxymethyl)tetrahydrofuran-3-yl)oxy)methyl)-1H-1,2,3-triazol-1-yl)methyl)-4-hydroxytetrahydrofuran-2-yl)-1H-purin-6(9H)-one;

2-amino-9-((2R,4S,5R)-5-(2-(2-((2S,3S,5R)-5-(2-amino-6-oxo-1H-purin-9(6H)-yl)-2-(hydroxymethyl)tetrahydrofuran-3-yl)hydrazinyl)ethyl)-4-hydroxytetrahydrofuran-2-yl)-1H-purin-6(9H)-one;

2-amino-9-((2R,4S,5R)-5-(2-((((2R,3S,5R)-5-(2-amino-6-oxo-1H-purin-9(6H)-yl)-2-(hydroxymethyl)tetrahydrofuran-3-yl)oxy)amino)ethyl)-4-hydroxytetrahydrofuran-2-yl)-1H-purin-6(9H)-one;

3-(((2S,3S,5R)-5-(2-amino-6-oxo-1H-purin-9(6H)-yl)-2-(hydroxymethyl)tetrahydrofuran-3-yl)amino)-4-((((2R,3S,5R)-5-(2-amino-6-oxo-1H-purin-9(6H)-yl)-3-hydroxytetrahydrofuran-2-ylmethyl)amino)cyclobut-3-ene-1,2-dione;

2-amino-9-((2R,4S,5R)-5-(((((2R,3S,5R)-5-(2-amino-6-oxo-1H-purin-9(6H)-yl)-2-(hydroxymethyl)tetrahydrofuran-3-yl)oxy)amino)methyl)-4-hydroxytetrahydrofuran-2-yl)-1H-purin-6(9H)-one;

2-amino-9-((2R,4S,5R)-5-(((2-(((2S,3S,5R)-5-(2-amino-6-oxo-1H-purin-9(6H)-yl)-2-(hydroxymethyl)tetrahydrofuran-3-yl)amino)propan-2-yl)amino)methyl)-4-hydroxytetrahydrofuran-2-yl)-1H-purin-6(9H)-one;

2-amino-9-((2R,4S,5R)-5-(((2-(((2S,3S,5R)-5-(2-amino-6-oxo-1H-purin-9(6H)-yl)-2-(hydroxymethyl)tetrahydrofuran-3-yl)amino)-1,1,1,3,3,3-hexafluoropropan-2-yl)amino)methyl)-4-hydroxytetrahydrofuran-2-yl)-1H-purin-6(9H)-one;

2-amino-9-((2R,4S,5R)-5-((((((2S,3S,5R)-5-(2-amino-6-oxo-1H-purin-9(6H)-yl)-2-(hydroxymethyl)tetrahydrofuran-3-yl)amino)dimethylsilyl)amino)methyl)-4-hydroxytetrahydrofuran-2-yl)-1H-purin-6(9H)-one;

1-((2S,3S,5R)-5-(2-amino-6-oxo-1H-purin-9(6H)-yl)-2-(hydroxymethyl)tetrahydrofuran-3-yl)-3-(((2R,3S,5R)-5-(2-amino-6-oxo-1H-purin-9(6H)-yl)-3-hydroxytetrahydrofuran-2-yl)methyl)urea;

2-amino-9-((2R,3R,4S,5S)-4-(4-(((2R,3S,4R,5R)-5-(2-amino-6-oxo-1H-purin-9(6H)-yl)-3,4-dihydroxytetrahydrofuran-2-yl)methyl)-1H-1,2,3-triazol-1-yl)-3-hydroxy-5-(hydroxymethyl)tetrahydrofuran-2-yl)-1H-purin-6(9H)-one;

2-amino-9-((2R,3R,4S,5S)-4-(4-((2R,3S,4R,5R)-5-(2-amino-6-oxo-1H-purin-9(6H)-yl)-3,4-dihydroxytetrahydrofuran-2-yl)-1H-1,2,3-triazol-1-yl)-3-hydroxy-5-(hydroxymethyl)tetrahydrofuran-2-yl)-1H-purin-6(9H)-one;

2-amino-9-((2R,3R,4S,5R)-5-((4-((((2R,3S,5R)-5-(2-amino-6-oxo-1H-purin-9(6H)-yl)-2-(hydroxymethyl)tetrahydrofuran-3-yl)oxy)methyl)-1H-1,2,3-triazol-1-yl)methyl)-3,4-dihydroxytetrahydrofuran-2-yl)-1H-purin-6(9H)-one;

2-amino-9-((2R,3R,4S,5S)-4-(2-(2-((2R,3S,4R,5R)-5-(2-amino-6-oxo-1H-purin-9(6H)-yl)-3,4-dihydroxytetrahydrofuran-2-yl)ethyl)hydrazinyl)-3-hydroxy-5-(hydroxymethyl)tetrahydrofuran-2-yl)-1H-purin-6(9H)-one;

2-amino-9-((2R,3R,4S,5R)-4-(((2-((2R,3S,4R,5R)-5-(2-amino-6-oxo-1H-purin-9(6H)-yl)-3,4-dihydroxytetrahydrofuran-2-yl)ethyl)amino)oxy)-3-hydroxy-5-(hydroxymethyl)tetrahydrofuran-2-yl)-1H-purin-6(9H)-one;

2-amino-9-((2R,3R,4S,5S)-4-(2-(((2R,3S,4R,5R)-5-(2-amino-6-oxo-1H-purin-9(6H)-yl)-3,4-dihydroxytetrahydrofuran-2-yl)methyl)hydrazinyl)-3-hydroxy-5-(hydroxymethyl)tetrahydrofuran-2-yl)-1H-purin-6(9H)-one;

3-((((2R,3S,4R,5R)-5-(2-amino-6-oxo-1H-purin-9(6H)-yl)-3,4-dihydroxytetrahydrofuran-2-yl)methyl)amino)-4-(((2S,3S,4R,5R)-5-(2-amino-6-oxo-1H-purin-9(6H)-yl)-4-hydroxy-2-(hydroxymethyl)tetrahydrofuran-3-yl)amino)cyclobut-3-ene-1,2-dione;

2-amino-9-((2R,3R,4S,5S)-4-((2-((((2R,3S,4R,5R)-5-(2-amino-6-oxo-1H-purin-9(6H)-yl)-3,4-dihydroxytetrahydrofuran-2-yl)methyl)amino)propan-2-yl)amino)-3-hydroxy-5-(hydroxymethyl)tetrahydrofuran-2-yl)-1H-purin-6(9H)-one;

2-amino-9-((2R,3R,4S,5S)-4-(2-((((2R,3S,4R,5R)-5-(2-amino-6-oxo-1H-purin-9(6H)-yl)-3,4-dihydroxytetrahydrofuran-2-yl)methyl)amino)-1,1,1,3,3,3-hexafluoropropan-2-yl)amino)-3-hydroxy-5-(hydroxymethyl)tetrahydrofuran-2-yl)-1H-purin-6(9H)-one;

2-amino-9-((2R,3R,4S,5S)-4-((((((2R,3S,4R,5R)-5-(2-amino-6-oxo-1H-purin-9(6H)-yl)-3,4-dihydroxytetrahydrofuran-2-yl)methyl)amino)dimethylsilyl)amino)-3-hydroxy-5-(hydroxymethyl)tetrahydrofuran-2-yl)-1H-purin-6(9H)-one;

1-(((2R,3S,4R,5R)-5-(2-amino-6-oxo-1H-purin-9(6H)-yl)-3,4-dihydroxytetrahydrofuran-2-yl)methyl)-3-((2S, 3S,4R,5R)-5-(2-amino-6-oxo-1H-purin-9(6H)-yl)-4-hydroxy-2-(hydroxymethyl)tetrahydrofuran-3-yl)urea;

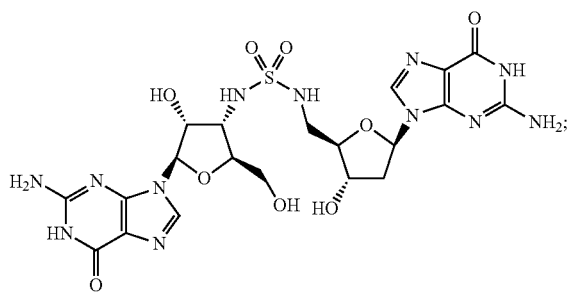

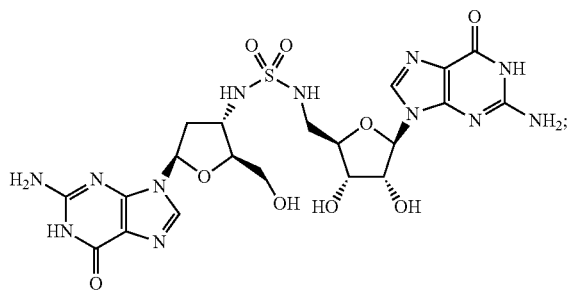

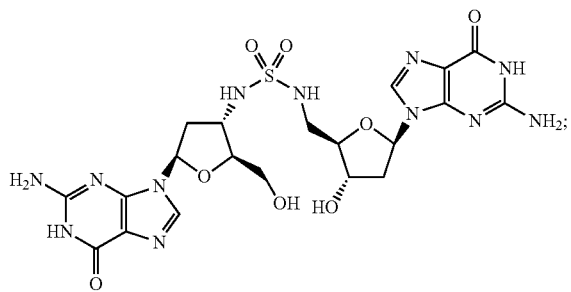

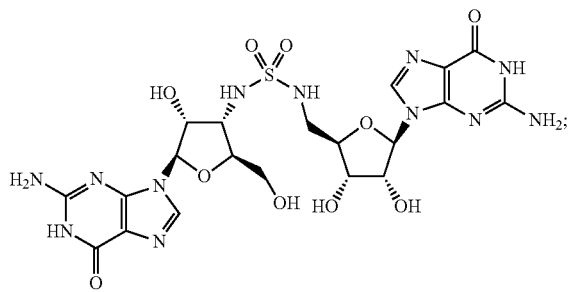

((2S,3S,4R,5R)-5-(2-amino-6-oxo-1H-purin-9(6H)-yl)-3-(4-(((2R,3S,4R,5R)-5-(2-amino-6-oxo-1H-purin-9(6H)-yl)-3,4-dihydroxytetrahydrofuran-2-yl)methyl)-1H-1,2,3-triazol-1-yl)-4-hydroxytetrahydrofuran-2-yl) methyl 5-((3aS,4S,6aR)-2-oxohexahydro-1H-thieno[3,4-d]imidazol-4-yl)pentanoate;

(2R,3S,4R,5R)-5-(2-amino-6-oxo-1H-purin-9(6H)-yl)-2-((1-((2S,3S,4R,5R)-5-(2-amino-6-oxo-1H-purin-9(6H)-yl)-4-hydroxy-2-(hydroxymethyl)tetrahydrofuran-3-yl)-1H-1,2,3-triazol-4-yl)methyl)-4-hydroxytetrahydrofuran-3-yl 5-((3aS,4S,6aR)-2-oxohexahydro-1H-thieno[3,4-d]imidazol-4-yl)pentanoate;

2-amino-9-((2R,3R,4S,5R)-5-((1-((2S,3S,4R,5R)-5-(2-amino-6-oxo-1H-purin-9(6H)-yl)-2-(((((4R)-4-(3-chlo-rophenyl)-2-oxido-1,3,2-dioxaphosphinan-2-yl)oxy) methyl)-4-hydroxytetrahydrofuran-3-yl)-1H-1,2,3-triazol-4-yl)methyl)-3,4-dihydroxytetrahydrofuran-2-yl)-1H-purin-6(9H)-one; and ((2S,3S,4R,5R)-5-(2-amino-6-oxo-1H-purin-9(6H)-yl)-3-(4-(((2R,3S,4R,5R)-5-(2-amino-6-oxo-1H-purin-9(6H)-yl)-3,4-dihydroxytetrahydrofuran-2-yl)methyl)-1H-1,2,3-triazol-1-yl)-4-hydroxytetrahydrofuran-2-yl) methyl dihydrogen phosphate.

6. A compound according to claim 5, selected from the group consisting of:

3-((((2R,3S,5R)-5-(2-amino-6-oxo-1H-purin-9(6H)-yl)-3-hydroxytetrahydrofuran-2-yl)methyl)amino)-4-(((2S,3S,4R,5R)-5-(2-amino-6-oxo-1H-purin-9(6H)-yl)-4-hydroxy-2-(hydroxymethyl)tetrahydrofuran-3-yl)amino)cyclobut-3-ene-1,2-dione;

3-((((2R,3S,4R,5R)-5-(2-amino-6-oxo-1H-purin-9(6H)-yl)-3,4-dihydroxytetrahydrofuran-2-yl)methyl)amino)-4-(((2S,3S,4R,5R)-5-(2-amino-6-oxo-1H-purin-9(6H)-yl)-4-hydroxy-2-(hydroxymethyl)tetrahydrofuran-3-yl)amino)cyclobut-3-ene-1,2-dione, and a salt thereof.

7. A process for preparing a compound of Formula I according to claim 1, said process comprising:

reacting a compound of Formula Ib with an ester or phosphoester:

Ib

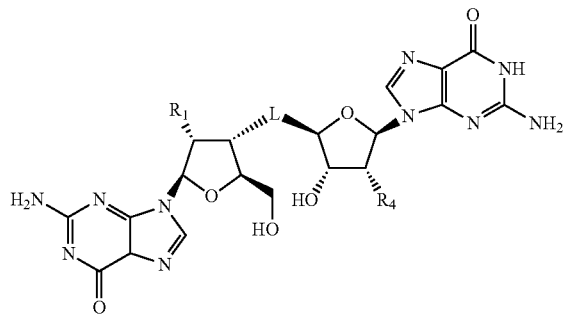

to from a compound of Formula I:

I

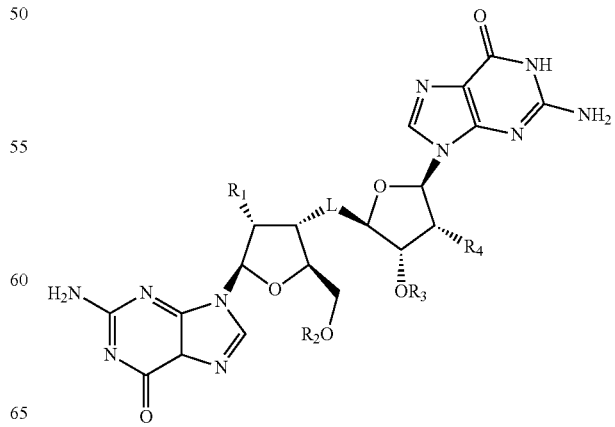

wherein:

L is selected from the group consisting of:

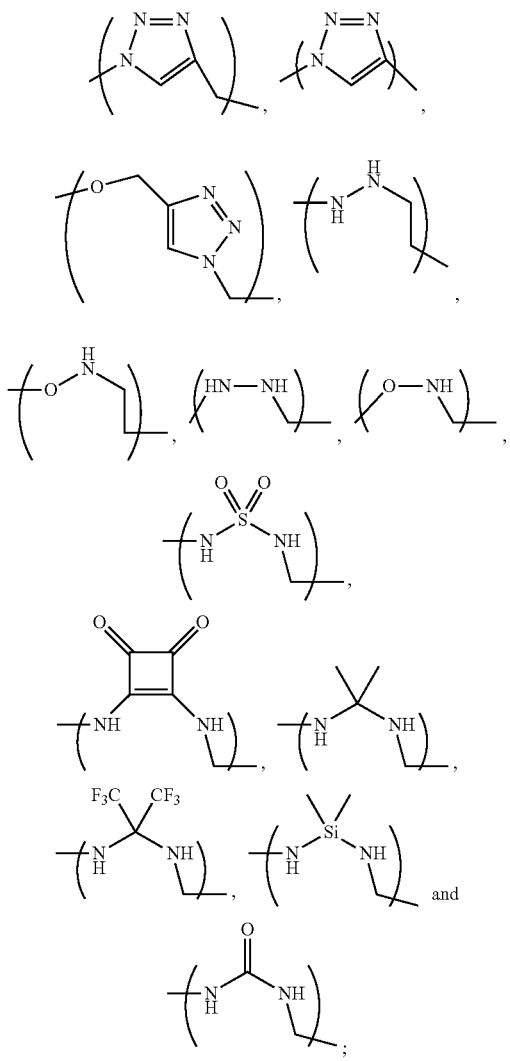

$R_1$ is selected from the group consisting of hydrogen, hydroxyl, $(C_1$-$C_6)$alkyl, $(C_1$-$C_6)$alkyloxy and —OPO$_3$H$_2$;

$R_2$ is selected from the group consisting of:
hydrogen,
—PO$_3$H$_2$,

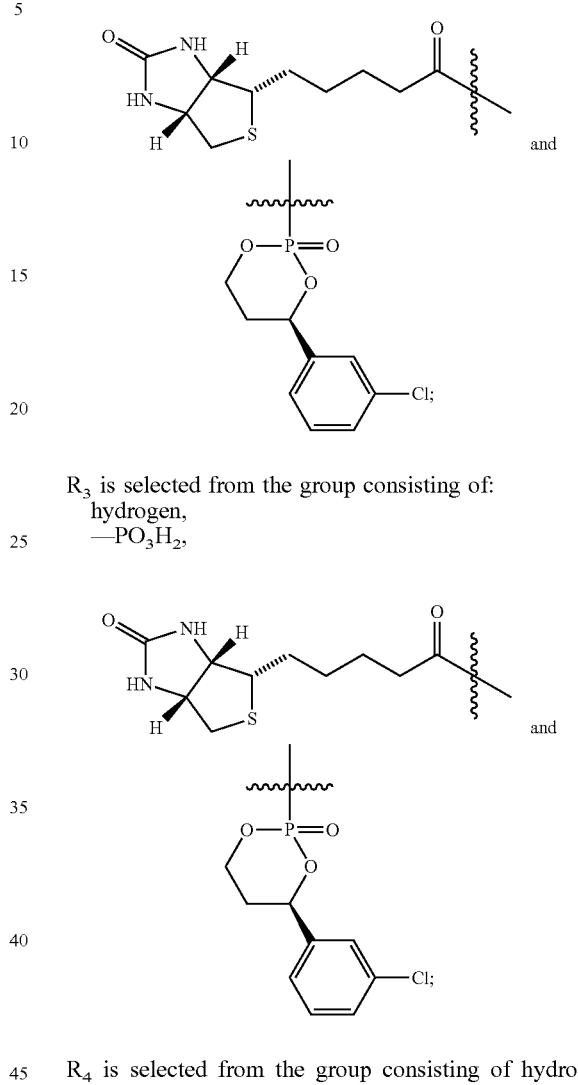

$R_3$ is selected from the group consisting of:
hydrogen,
—PO$_3$H$_2$, and $R_4$ is selected from the group consisting of hydrogen, hydroxyl, $(C_1$-$C_6)$alkyl, $(C_1$-$C_6)$alkyloxy and —OPO$_3$H$_2$;

provided at least one of $R_2$ or $R_3$ is other than hydrogen.

* * * * *